(12) United States Patent
Umeno et al.

(10) Patent No.: US 9,963,731 B2
(45) Date of Patent: May 8, 2018

(54) METHOD FOR PRODUCING CAROTENOIDS EACH HAVING 50 CARBON ATOMS

(71) Applicant: National University Corporation Chiba University, Chiba (JP)

(72) Inventors: Daisuke Umeno, Chiba (JP); Maiko Furubayashi, Chiba (JP); Norihiko Misawa, Ishikawa (JP); Shinichi Takaichi, Kanagawa (JP)

(73) Assignee: National University Corporation Chiba University, Chiba (JP)

( * ) Notice: Subject to any disclaimer, the term of this patent is extended or adjusted under 35 U.S.C. 154(b) by 0 days. days.

(21) Appl. No.: 15/384,420

(22) Filed: Dec. 20, 2016

(65) Prior Publication Data

US 2017/0191103 A1     Jul. 6, 2017

Related U.S. Application Data

(63) Continuation of application No. 14/124,256, filed as application No. PCT/JP2012/064817 on Jun. 8, 2012, now Pat. No. 9,562,220.

(30) Foreign Application Priority Data

Jun. 10, 2011     (JP) ................ 2011-130326

(51) Int. Cl.
| | | |
|---|---|---|
| *C12P 23/00* | (2006.01) | |
| *C12N 1/20* | (2006.01) | |
| *C12N 1/00* | (2006.01) | |
| *C12N 15/00* | (2006.01) | |
| *C12P 21/06* | (2006.01) | |
| *C12P 19/34* | (2006.01) | |
| *C12N 9/06* | (2006.01) | |
| *C07H 21/04* | (2006.01) | |
| *C07K 1/00* | (2006.01) | |
| *C12N 15/52* | (2006.01) | |

(52) U.S. Cl.
CPC .............. *C12P 23/00* (2013.01); *C12N 15/52* (2013.01); *C12Y 205/0101* (2013.01); *C12Y 205/01096* (2013.01)

(58) Field of Classification Search
CPC . C12P 23/00; C12N 15/52; C12Y 205/01096; C12Y 205/0101
USPC ..... 435/67, 252.3, 254.11, 320.1, 69.1, 91.1, 435/191; 536/23.1, 23.2; 530/350
See application file for complete search history.

(56) References Cited

U.S. PATENT DOCUMENTS

| | | |
|---|---|---|
| 7,288,387 B2 | 10/2007 | Cheng et al. |
| 2005/0260699 A1 | 11/2005 | Desouza et al. |
| 2014/0170700 A1 | 6/2014 | Umeno et al. |

OTHER PUBLICATIONS

Office Action issued in corresponding Japanese Patent Application No. 2016-121343 dated Mar. 30, 2017 with English translation (6 pages).
Umeno, Daisuke, "Evolutional Engineering of Metabolic Pathway and Its Gene Control Circuit," Summary of the Lectures, Japanese Society of Enzyme Engineering, Nov. 19, 2010, pp. 14-20 (24 pages) with English translation.
Umeno, Daisuke, "Evolved Activity of Non-natural Carotenoid Synthetic Pathway," Summary of the Lectures, Japan Society for Bioscience, Biotechnology, and Argochemistry Kanto branch, 2010, pp. 25 (7 pages) with English translation.
Office Action issued in corresponding Japanese Patent Application No. 2013-519547 dated Apr. 21, 2016 with English translation (11 pages).
Tobias et al., "Biosynthesis of novel carotenoid families based on unnatural carbon backbones: a model for diversification of natural product pathways," Biochimica et Biophysica Acta, 2006, vol. 1761, Issue 2, pp. 235-246.
Umeno, D., "Construction of Artificial Metabolic Networks," Experimental Medicine, 2011, vol. 29, No. 7, pp. 61-67 (25 pages) with English translation.
Stickforth et al., "Kinetic variations determine the product pattern of phytoene desaturase from Rubrivivax gelatinosus," Archives of Biochemistry and Biophysics, 2007, vol. 461, No. 2, pp. 235-241.
Wang et al., "Alteration of Product Specificity of Rhodobacter sphaeroides Phytoene Desaturase by Directed Evolution," The Journal of Biological Chemistry, 2001, vol. 276, No. 44, pp. 41161-41164.
Stickforth et al., "Structural and kinetics properties of a mutated phytoene desaturase from Rubrivivax gelatinosus with modified product specificity," Archives of Biochemistry and Biophysics, 2011, vol. 505, No. 1, pp. 118-122.
Broun et al., "Catalytic Plasticity of Fatty Acid Modification Enzymes Underlying Chemical Diversity of Plant Lipids," Science, 1998, vol. 282, pp. 1315-1317.
Devos et al., "Practical Limits of Function Prediction," Proteins: Structure, Function, and Genetics, 2000, vol. 41, pp. 98-107.
Seffernick et al., "Melamine Deaminase and Atrazine Chlorohydrolase: 98 Percent Identical but Functionally Different," Journal of Bacteriology, 2001, vol. 183, No. 8, pp. 2405-2410.
Whisstock et al., "Prediction of protein function from protein sequence and structure," Quarterly Reviews of Biophysics, 2003, vol. 36 (3), pp. 307-340.
Witkowski et al., "Conversion of B-Ketoacyl Synthase to a Malonyl Decarboxylase by Replacement of the Active-Site Cysteine with Glutamine," Biochemistry, 1999, vol. 38, pp. 11643-11650.

*Primary Examiner* — Ganapathirama Raghu
(74) *Attorney, Agent, or Firm* — Kilyk & Bowersox, P.L.L.C.

(57) ABSTRACT

The present invention provides a method of producing a carotenoid having 50 carbon atoms which comprises culturing, in a medium, a cell transformed with a mutant phytoene desaturase gene and obtaining the carotenoid having 50 carbon atoms from the culture. The mutant phytoene desaturase gene has an introduced mutation to encode a mutant phytoene desaturase having an enhanced activity to desaturate a carotenoid backbone compound of 50 carbon atoms.

2 Claims, 20 Drawing Sheets

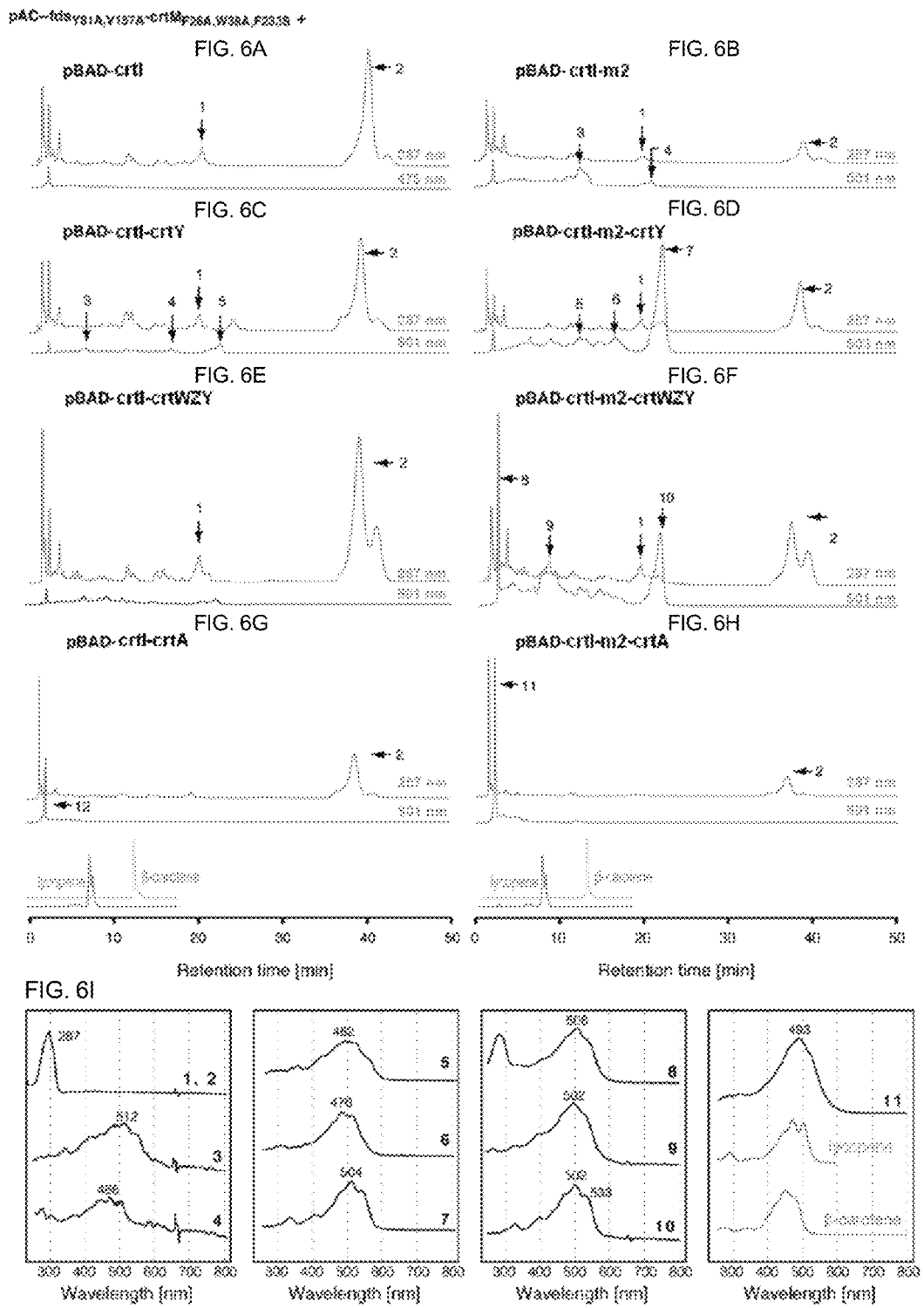

Crtl* = Crtl-m2

```
                        SEQUENCE LISTING

<160> NUMBER OF SEQ ID NOS: 28

<210> SEQ ID NO 1
<211> LENGTH: 492
<212> TYPE: PRT
<213> ORGANISM: Pantoea ananatis

<400> SEQUENCE: 1

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Glu Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
```

```
                115                 120                 125
Arg Ala Val Phe Lys Glu Gly Tyr Leu Lys Leu Gly Thr Val Pro Phe
130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
            195                 200                 205

Arg Glu Trp Gly Val Trp Phe Pro Arg Gly Gly Thr Gly Ala Leu Val
        210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Asn
290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
            420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Thr Asn Leu Tyr Leu Val Gly
450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 2
<211> LENGTH: 1479
<212> TYPE: DNA
<213> ORGANISM: Pantoea ananatis

<400> SEQUENCE: 2
```

```
atgaaaccaa ctacggtaat tggtgcaggc ttcggtggcc tggcactggc aattcgtcta      60
caagctgcgg ggatccccgt cttactgctt gaacaacgtg ataaacccgg cggtcgggct     120
tatgtctacg aggatcaggg gtttaccttt gatgcaggcc cgacggttat caccgatccc     180
agtgccattg aagaactgtt tgcactggca ggaaaacagt taaagagta tgtcgaactg      240 ctgccggtta cgccgtttta ccgcctgtgt tgggagtcag ggaaggtctt taattacgat     300
aacgatcaaa cccggctcga agcgcagatt cagcagttta atccccgcga tgtcgaaggt     360
tatcgtcagt ttctggacta ttcacgcgcg gtgtttaaag aaggctatct aaagctcggt     420
actgtcccct tttatcgtt cagagacatg cttcgcgccg cacctcaact ggcgaaactg      480
caggcatgga gaagcgttta cagtaaggtt gccagttaca tcgaagatga acatctgcgc     540
caggcgtttt cttccactc gctgttggtg ggcggcaatc ccttcgccac ctcatccatt      600
tatacgttga tacacgcgct ggagcgtgag tgggcgtct ggtttccgcg tggcggcacc      660
ggcgcattag ttcaggggat gataaagctg tttcaggatc tgggtggcga agtcgtgtta     720
aacgccagag tcagccatat ggaaacgaca ggaaacaaga ttgaagccgt gcatttagag     780
gacggtcgca ggttcctgac gcaagccgtc gcgtcaaatg cagatgtggt tcatacctat     840
cgcgacctgt taagccagca ccctgccgcg gttaagcagt ccaacaaact gcagactaag     900
cgcatgagta actctctgtt tgtgctctat tttggtttga atcaccatca tgatcagctc     960
gcgcatcaca cggttttgttt cggcccgcgt taccgcgagc tgattgacga aattttaat    1020 catgatggcc tcgcagagga cttctcactt tatctgcacg cgccctgtgt cacggattcg    1080
tcactggcgc ctgaaggttg cggcagttac tatgtgttgg cgccggtgcc acatttaggc    1140
accgcgaacc tcgactggac ggttgagggg ccaaaactac gcgaccgtat ttttgcgtac    1200
cttgagcagc attacatgcc tggcttacgg agtcagctgg tcacgcaccg gatgtttacg    1260
ccgtttgatt ttcgcgacca gcttaatgcc tatcatggct cagccttttc tgtggagccc    1320
gttcttaccc agagcgcctg gtttcggccg cataaccgcg ataaaaccat tactaatctc    1380
tacctggtcg gcgcaggcac gcatcccggc gcaggcattc ctggcgtcat cggctcggca    1440
aaagcgacag caggtttgat gctggaggat ctgatttga                           1479
```

<210> SEQ ID NO 3
<211> LENGTH: 1479
<212> TYPE: DNA
<213> ORGANISM: Artificial Sequence
<220> FEATURE:
<223> OTHER INFORMATION: Pantoea ananatis crtI mutant (N304S)

<400> SEQUENCE: 3

```
atgaaaccaa ctacggtaat tggtgcaggc ttcggtggcc tggcactggc aattcgtcta      60
caagctgcgg ggatccccgt cttactgctt gaacaacgtg ataaacccgg cggtcgggct     120
tatgtctacg aggatcaggg gtttaccttt gatgcaggcc cgacggttat caccgatccc     180
agtgccattg aagaactgtt tgcactggca ggaaaacagt taaagagta tgtcgaactg      240 ctgccggtta cgccgtttta ccgcctgtgt tgggagtcag ggaaggtctt taattacgat     300
aacgatcaaa cccggctcga agcgcagatt cagcagttta atccccgcga tgtcgaaggt     360
tatcgtcagt ttctggacta ttcacgcgcg gtgtttaaag aaggctatct aaagctcggt     420
actgtcccct tttatcgtt cagagacatg cttcgcgccg cacctcaact ggcgaaactg      480
caggcatgga gaagcgttta cagtaaggtt gccagttaca tcgaagatga acatctgcgc     540
caggcgtttt cttccactc gctgttggtg ggcggcaatc ccttcgccac ctcatccatt      600
```

```
tatacgttga tacacgcgct ggagcgtgag tggggcgtct ggtttccgcg tggcggcacc    660
ggcgcattag ttcaggggat gataaagctg tttcaggatc tgggtggcga agtcgtgtta    720
aacgccagag tcagccatat ggaaacgaca ggaaacaaga ttgaagccgt gcatttagag    780
gacggtcgca ggttcctgac gcaagccgtc gcgtcaaatg cagatgtggt tcatacctat    840
cgcgacctgt taagccagca ccctgccgcg gttaagcagt ccaacaaact gcagactaag    900
cgcatgagta gctctctgtt tgtgctctat tttggtttga atcaccatca tgatcagctc    960
gcgcatcaca cggtttgttt cggcccgcgt taccgcgagc tgattgacga aattttaat   1020 catgatggcc tcgcagagga cttctcactt tatctgcacg cgccctgtgt cacggattcg   1080
tcactggcgc ctgaaggttg cggcagttac tatgtgttgg cgccggtgcc acatttaggc   1140
accgcgaacc tcgactggac ggttgagggg ccaaaactac gcgaccgtat ttttgcgtac   1200
cttgagcagc attacatgcc tggcttacgg agtcagctgg tcacgcaccg atgtttacg    1260 ccgtttgatt tcgcgacca gcttaatgcc tatcatggct cagccttttc tgtggagccc    1320
gttcttaccc agagcgcctg gtttcggccg cataaccgcg ataaaaccat tactaatctc   1380
tacctggtcg gcgcaggcac gcatcccggc gcaggcattc ctggcgtcat cggctcggca   1440
aaagcgacag caggtttgat gctggaggat ctgatttga                          1479

<210> SEQ ID NO 4
<211> LENGTH: 894
<212> TYPE: DNA
<213> ORGANISM: Artificial Sequence
<220> FEATURE:
<223> OTHER INFORMATION: Geobacillus stearothermophillus fds mutant
      (Y81A, V157A)

<400> SEQUENCE: 4
atggcgcagc tttcagttga acagtttctc aacgagcaaa acaggcggt ggaaacagcg     60 ctctcccgtt atatagagcg cttagaaggg ccggcgaagc tgaaaaaggc gatggcgtac   120
tcattggagg ccggcggcaa acgaatccgt ccgttgctgc ttctgtccac cgttcgggcg   180
ctcggcaaag acccggcggt cggattgccc gtcgcctgcg cgattgaaat gatccatacg   240
gcatctttga tccatgatga tttgccgagc atggacaacg atgatttgcg gcgcggcaag   300
ccgacgaacc ataaagtgtt cggcgaggcg atggccatct ggcgggggga cgggttgttg   360
acgtacgcgt ttcaattgat caccgaaatc gacgatgagc gcatccctcc ttccgtccgg   420
cttcggctca tcgaacggct ggcgaaagcg gccggtccgg aagggatggc ggccggtcag   480
gcagccgata tggaaggaga ggggaaaacg ctgacgcttt cggagctcga atacattcat   540
cggcataaaa ccgggaaaat gctgcaatac agcgtgcacg ccggcgcctt gatcggcggc   600
gctgatgccc ggcaaacgcg ggagcttgac gaattcgccg cccatctagg ccttgccttt   660
caaattcgcg atgatattct cgatattgaa ggggcagaag aaaaaatcgg caagccggtc   720
ggcagcgacc aaagcaacaa caaagcgacg tatccagcgt tgctgtcgct tgccggcgcg   780
aaggaaaagt tggcgttcca tatcgaggcg gcgcagcgcc atttacggaa cgctgacgtt   840
gacggcgccg cgctcgccta tatttgcgaa ctggtcgccg cccgcgacca ttaa          894

<210> SEQ ID NO 5
<211> LENGTH: 864
<212> TYPE: DNA
<213> ORGANISM: Artificial Sequence
<220> FEATURE:
<223> OTHER INFORMATION: Staphylococcus aureus crtM mutant (F26A, W38A,
```

F233S)

<400> SEQUENCE: 5

| | | | | | |
|---|---|---|---|---|---|
| atgacaatga | tgaatatgaa | ttttaaatat | tgtcataaaa | tcatgaagaa | acattcaaaa | 60
| agcttttctt | acgctgcgga | cttgttacca | gaagatcaaa | gaaaagcggt | tgcggcaatt | 120
| tatgctgtgt | gtcgtaaaat | tgatgacagt | atagatgttt | atggcgatat | tcaattttta | 180
| aatcaaataa | aagaagatat | acaatctatt | gaaaaatacc | catatgaaca | tcatcacttt | 240
| caaagtgatc | gtagaatcat | gatggcgctt | cagcatgttg | cacaacataa | aaatatcgcc | 300
| tttcaatctt | tttataatct | cattgatact | gtatataaag | atcaacattt | tacaatgttt | 360
| gaaacggacg | ctgaattatt | cggatattgt | tatggtgttg | ctggtacagt | aggtgaagta | 420
| ttgacgccga | ttttaagtga | tcatgaaaca | catcagacat | acgatgtcgc | aagaagactt | 480
| ggtgaatcgt | tgcaattgat | taatatatta | agagatgtcg | gtgaagattt | tgacaatgaa | 540
| cggatatatt | ttagtaagca | acgattaaag | caatatgaag | ttgatattgc | tgaagtgtac | 600
| caaaatggtg | ttaataatca | ttatattgac | ttatgggaat | attatgcagc | tatcgcagaa | 660
| aaagattttc | aagatgttat | ggatcaaatc | aaagtatcta | gtattgaagc | acaaccaatc | 720
| atagaattag | cagcacgtat | atatattgaa | atactggacg | aagtgagaca | ggctaactat | 780
| acattacatg | aacgtgtttt | tgtggataag | aggaaaaagg | caaagttgtt | tcatgaaata | 840
| aatagtaaat | atcatagaat | atag | | | | 864

<210> SEQ ID NO 6
<211> LENGTH: 2503
<212> TYPE: DNA
<213> ORGANISM: Artificial Sequence
<220> FEATURE:
<223> OTHER INFORMATION: crtZWY gene derived from Paracoccus sp., N81106 strain

<400> SEQUENCE: 6

| | | | | | |
|---|---|---|---|---|---|
| ggcgaccttg | cggcgctgcg | ccgcgcgcct | ttgctggtgc | ctgggccggg | tggccaatgg | 60
| tcgcaagcaa | cggggatgga | aaccggcgat | gcgggactgt | agtctgcgcg | atcgccggt | 120
| ccgggggaca | agatgagcgc | acatgccctg | cccaaggcag | atctgaccgc | caccagcctg | 180
| atcgtctcgg | gcggcatcat | cgccgcttgg | ctggccctgc | atgtgcatgc | gctgtggttt | 240
| ctggacgcag | cggcgcatcc | catcctggcg | atcgcaaatt | tcctggggct | gacctggctg | 300
| tcggtcggat | tgttcatcat | cgcgcatgac | gcgatgcacg | ggtcggtggt | gccggggcgt | 360
| ccgcgcgcca | atgcggcgat | gggccagctt | gtcctgtggc | tgtatgccgg | attttcgtgg | 420
| cgcaagatga | tcgtcaagca | catggcccat | caccgccatg | ccggaaccga | cgacgacccc | 480
| gatttcgacc | atggcggccc | ggtccgctgg | tacgcccgct | tcatcggcac | ctatttcggc | 540
| tggcgcgagg | ggctgctgct | gcccgtcatc | gtgacggtct | atgcgctgat | ccttggggat | 600
| cgctggatgt | acgtggtctt | ctggccgctg | ccgtcgatcc | tggcgtcgat | ccagctgttc | 660
| gtgttcggca | cctggctgcc | gcaccgcccc | ggccacgacg | cgttcccgga | ccgccacaat | 720
| gcgcggtcgt | cgcggatcag | cgaccccgtg | tcgctgctga | cctgctttca | ctttggcggt | 780
| tatcatcacg | aacaccacct | gcaccgacg | gtgccgtggg | ggcgcctgcc | cagcacccgc | 840
| accaaggggg | acaccgcatg | accaatttcc | tgatcgtcgt | cgccaccgtg | ctggtgatgg | 900
| agttgacggc | ctattccgtc | caccgctgga | tcatgcacgg | cccctgggc | tggggctggc | 960
| acaagtccca | ccacgaggaa | cacgaccacg | cgctggaaaa | gaacgacctg | tacggcctgg | 1020

```
tctttgcggt gatcgccacg gtgctgttca cggtgggctg gatctgggcg ccggtcctgt    1080
ggtggatcgc cttgggcatg actgtctatg ggctgatcta tttcgtcctg catgacgggc    1140
tggtgcatca gcgctggccg ttccgttata tcccgcgcaa gggctatgcc agacgcctgt    1200
atcaggccca ccgcctgcac catgcggtcg aggggcgcga ccattgcgtc agcttcggct    1260
tcatctatgc gcccccggtc gacaagctga agcaggacct gaagatgtcg ggcgtgctgc    1320
gggccgaggc gcaggagcgc acgtgaccca tgacgtgctg ctggcagggg cgggccttgc    1380
caacgggctg atcgccctgg cgctgcgcgc ggcgcggccc gacctgcgcg tgctgctgct    1440
ggaccatgcc gcaggaccgt cagacggcca cacctggtcc tgccacgacc ccgacctgtc    1500
gccggactgg ctggcgcggc tgaagcccct cgccgcgcc aactggcccg accaggaggt    1560
gcgctttccc cgccatgccc ggcggctggc caccggttac gggtcgctgg acggggcggc    1620
gctggcggat gcggtggtcc ggtcgggcgc cgagatccgc tgggacagcg acatcgccct    1680
gctggatgcg caggggcgga cgctgtcctg cggcacccgg atcgaggcgg cgcggtcct    1740
ggacgggcgg ggcgcgcagc cgtcgcggca tctgaccgtg ggtttccaga aattcgtggg    1800
tgtcgagatc gagaccgacc gcccccacgg cgtgccccgc ccgatgatca tggacgcgac    1860
cgtcacccag caggacgggt accgcttcat ctatctgctg cccttctctc cgacgcgcat    1920
cctgatcgag gacacgcgct attccgatgg cggcgatctg gacgacgacg cgctggcggc    1980
ggcgtcccac gactatgccc gccagcaggg ctggaccggg gccgaggtcc ggcgcgaacg    2040
cggcatcctt cccatcgcgc tggcccatga tgcggcgggc ttctgggccg atcacgcggc    2100
ggggcctgtt cccgtgggac tgcgcgcggg gttctttcat ccggtcaccg gctattcgct    2160
gccctatgcg gcacaggtgg cggacgtggt ggcgggtctg tccgggccgc ccggcaccga    2220
cgcgctgcgc ggcgccatcc gcgattacgc gatcgaccgg gcgcgccgcg accgcttct    2280
gcgccttttg aaccggatgc tgttccgcgg ctgcgcgccc gaccggcgct ataccctgct    2340
gcagcggttc taccgcatgc cgcatggact gatcgaacgg ttctatgccg gccggctgag    2400
cgtggcggat cagctgcgca tcgtgaccgg caagcctccc attcccctttg gcacggccat    2460
ccgctgcctg cccgaacgtc ccctgctgaa ggaaaacgca tga                      2503
```

<210> SEQ ID NO 7
<211> LENGTH: 726
<212> TYPE: DNA
<213> ORGANISM: Rhodobacter capsulatus

<400> SEQUENCE: 7

```
atgccagtcg ccagccttag cttattcaga tttgatggca ccagctccct gccgtgggtg     60
attagccaaa tgatcttgtc tcgtcgtcca ctgaacgacg aaccgcgtgt gaagttctat    120
aagctgtgcg gcagcggcac gggtgagggc ttcaccccga aaccgaattg gcgtgtttgg    180
gcaattatgg cggcgttcga caccgaggcg atgcacgcg atgtcacggc aaaccatccg    240
gtttggaaac gttggcgtgc acacgcggca gaaaccctgg tgctgcattt gcagcctctg    300
tcggcccgtg gcacctgggg cggtgtgaat ccgttcctgc ggagcaggt ggcggagccg    360
agcccggacg agcggtcgt tgcgctgacc cgtgcggcga ttaaaccgca caaagcgaat    420
gcttttttgga gccgcgtgcc gaagattagc gagaaagttg gtgaagatca gaacctgatg    480
tttaagatcg gtatcggtga gattccgctg tttcaccaag ttacgttttc catctggcct    540
gatgtcgcga aaatgaacgc cttcgcccgt ggtgacaccc gcacggtaa ggcaatccgc    600
gctgcccgcg aagagggttg gttcacggaa gaactgtacg ctcgctttcg cctgctgggc    660
```

```
accgagggta gctggatggg taaagacccg ctggcgagca aggttctgga acgtgagact    720
gcgtaa                                                               726

<210> SEQ ID NO 8
<211> LENGTH: 5425
<212> TYPE: DNA
<213> ORGANISM: Artificial Sequence
<220> FEATURE:
<223> OTHER INFORMATION: Designed plasmid DNA, pAC-crtMF26A,W38A,F233S

<400> SEQUENCE: 8
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc    360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttcaaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcgtcca ttccgacagc atcgccagtc actatggcgt gctgctagcg ctatatgcgt   1740
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatcccgtgg aggtttcccg actggaaagc gggcagtgag cgcaacgcaa   1920
```

```
ttaatgtgag ttagctcact cattaggcac cccaggcttt acactttatg cttccggctc   1980
gtatgttgtg tggaattgtg agcggataac aatttcacac aggaaacaca tatggaattc   2040
tctagaagga ggattacaaa atgacaatga tgaatatgaa ttttaaatat tgtcataaaa   2100
tcatgaagaa acattcaaaa agcttttctt acgctgcgga cttgttacca gaagatcaaa   2160
gaaaagcggt tgcggcaatt tatgctgtgt gtcgtaaaat tgatgacagt atagatgttt   2220
atggcgatat tcaatttta aatcaaataa aagaagatat acaatctatt gaaaaatacc   2280
catatgaaca tcatcacttt caaagtgatc gtagaatcat gatggcgctt cagcatgttg   2340
cacaacataa aaatatcgcc tttcaatctt tttataatct cattgatact gtatataaag   2400
atcaacattt tacaatgttt gaaacggacg ctgaattatt cggatattgt tatggtgttg   2460
ctggtacagt aggtgaagta ttgacgccga ttttaagtga tcatgaaaca catcagacat   2520
acgatgtcgc aagaagactt ggtgaatcgt tgcaattgat taatatatta agagatgtcg   2580
gtgaagattt tgacaatgaa cggatatatt ttagtaagca acgattaaag caatatgaag   2640
ttgatattgc tgaagtgtac caaaatggtg ttaataatca ttatattgac ttatgggaat   2700
attatgcagc tatcgcagaa aaagattttc aagatgttat ggatcaaatc aaagtatcta   2760
gtattgaagc acaaccaatc atagaattag cagcacgtat atatattgaa atactggacg   2820
aagtgagaca ggctaactat acattacatg aacgtgtttt tgtggataag aggaaaaagg   2880
caaagttgtt tcatgaaata aatagtaaat atcatagaat atagctcgag gggcccggcg   2940
cctgatgcgg tattttctcc ttacgcatct gtgcggtatt tcacgtgcgc tcgaggggcc   3000
cggcgcctga tgcggtattt tctccttacg catctgtgcg gtatttcacg gatcctctac   3060
gccggacgca tcgtggccgg catcaccggc gccacaggtg cggttgctgg cgcctatatc   3120
gccgacatca ccgatgggga agatcgggct cgccacttcg gctcatgagc gcttgtttc    3180 ggcgtgggta tggtggcagg ccccgtggcc gggggactgt tgggcgccat ctccttgcat   3240
gcaccattcc ttgcggcggc ggtgctcaac ggcctcaacc tactactggg ctgcttccta   3300
atgcaggagt cgcataaggg agagcgtcga ccgatgccct tgagagcctt caacccagtc   3360
agctccttcc ggtgggcgcg gggcatgact atcgtcgccg cacttatgac tgtcttcttt   3420
atcatgcaac tcgtaggaca ggtgccggca gcgctctggg tcattttcgg cgaggaccgc   3480
tttcgctgga gcgcgacgat gatcggcctg tcgcttgcgg tattcggaat cttgcacgcc   3540
ctcgctcaag ccttcgtcac tggtcccgcc accaaacgtt tcggcgagaa gcaggccatt   3600
atcgccggca tggcggccga cgcgctgggc tacgtcttgc tggcgttcgc gacgcgaggc   3660
tggatggcct tccccattat gattcttctc gcttccggcg gcatcgggat gcccgcgttg   3720
caggccatgc tgtccaggca ggtagatgac gaccatcagg gacagcttca aggatcgctc   3780
gcggctctta ccagcctaac ttcgatcact ggaccgctga tcgtcacggc gatttatgcc   3840
gcctcggcga gcacatggaa cgggttggca tggattgtag gcgccgccct ataccttgtc   3900
tgcctccccg cgttgcgtcg cggtgcatgg agccgggcca cctcgacctg aatggaagcc   3960
ggcggcacct cgctaacgga ttcaccactc caagaattgg agccaatcaa ttcttgcgga   4020
gaactgtgaa tgcgcaaacc aacccttggc agaacatatc catcgcgtcc gccatctcca   4080
gcagccgcac gcggcgcatc tcgggcagcg ttgggtcctg gccacgggtg cgcatgatcg   4140
tgctcctgtc gttgaggacc cggctaggct ggcggggttg ccttactggt tagcagaatg   4200
aatcaccgat acgcgagcga acgtgaagcg actgctgctg caaaacgtct gcgacctgag   4260
caacaacatg aatggtcttc ggtttccgtg tttcgtaaag tctggaaacg cggaagtccc   4320
```

-continued

```
ctacgtgctg ctgaagttgc ccgcaacaga gagtggaacc aaccggtgat accacgatac    4380
tatgactgag agtcaacgcc atgagcggcc tcatttctta ttctgagtta caacagtccg    4440
caccgctgtc cggtagctcc ttccggtggg cgcggggcat gactatcgtc gccgcactta    4500
tgactgtctt ctttatcatg caactcgtag gacaggtgcc ggcagcgccc aacagtcccc    4560
cggccacggg gcctgccacc atacccacgc cgaaacaagc gccctgcacc attatgttcc    4620
ggatctgcat cgcaggatgc tgctggctac cctgtggaac acctacatct gtattaacga    4680
agcgctaacc gttttttatca ggctctggga ggcagaataa atgatcatat cgtcaattat    4740
tacctccacg gggagagcct gagcaaactg gcctcaggca tttgagaagc acacggtcac    4800
actgcttccg gtagtcaata aaccggtaaa ccagcaatag acataagcgg ctatttaacg    4860
accctgccct gaaccgacga ccgggtcgaa tttgctttcg aatttctgcc attcatccgc    4920
ttattatcac ttattcaggc gtagcaccag gcgtttaagg gcaccaataa ctgccttaaa    4980
aaaattacgc cccgccctgc cactcatcgc agtactgttg taattcatta agcattctgc    5040
cgacatggaa gccatcacag acggcatgat gaacctgaat cgccagcggc atcagcacct    5100
tgtcgccttg cgtataatat ttgcccatgg tgaaaacggg ggcgaagaag ttgtccatat    5160
tggccacgtt taaatcaaaa ctggtgaaac tcacccaggg attggctgag acgaaaaaca    5220
tattctcaat aaaccccttta gggaaatagg ccaggttttc accgtaacac gccacatctt    5280
gcgaatatat gtgtagaaac tgccggaaat cgtcgtggta ttcactccag agcgatgaaa    5340
acgtttcagt ttgctcatgg aaaacggtgt aacaagggtg aacactatcc catatcacca    5400
gctcaccgtc tttcattgcc atacg                                          5425
```

<210> SEQ ID NO 9
<211> LENGTH: 3394
<212> TYPE: DNA
<213> ORGANISM: Artificial Sequence
<220> FEATURE:
<223> OTHER INFORMATION: Designed plasmid DNA, pUC-fdsY81A, V157A

<400> SEQUENCE: 9

```
gcgcccaata cgcaaaccgc ctctcccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cacatatgga attctctaga aggaggagta     240
agcgatggcg cagcttttcag ttgaacagtt tctcaacgag caaaaacagg cggtggaaac     300
agcgctctcc cgttatatag agcgcttaga agggccggcg aagctgaaaa aggcgatggc     360
gtactcattg gaggccggcg gcaaacgaat ccgtccgttg ctgcttctgt ccaccgttcg     420
ggcgctcggc aaagacccgg cggtcggatt gcccgtcgcc tgcgcgattg aaatgatcca     480
tacggcatct ttgatccatg atgatttgcc gagcatggac aacgatgatt tgcggcgcgg     540
caagccgacg aaccataaag tgttcggcga ggcgatggcc atcttggcgg gggacgggtt     600
gttgacgtac gcgtttcaat tgatcaccga aatcgacgat gagcgcatcc ctccttccgt     660
ccggcttcgg ctcatcgaac ggctggcgaa agcggccggt ccggaaggga tggcggccgg     720
tcaggcagcc gatatggaag gagagggggaa aacgctgacg cttttcggagc tcgaatacat     780 tcatcggcat aaaaccggga aaatgctgca atacagcgtg cacgccggcg ccttgatcgg     840
cggcgctgat gcccggcaaa cgcgggagct tgacgaattc gccgcccatc taggccttgc     900
```

```
ctttcaaatt cgcgatgata ttctcgatat tgaaggggca gaagaaaaaa tcggcaagcc    960
ggtcggcagc gaccaaagca acaacaaagc gacgtatcca gcgttgctgt cgcttgccgg   1020
cgcgaaggaa aagttggcgt tccatatcga ggcggcgcag cgccatttac ggaacgctga   1080
cgttgacggc gccgcgctcg cctatatttg cgaactggtc gccgcccgcg accattaact   1140
cgaggggccc ggcgcctgat gcggtatttt ctccttacgc atctgtgcgg tatttcacac   1200
cgcatatatg gtgcactctc agtacaatct gctctgatgc cgcatagtta agccagcccc   1260
gacacccgcc aacacccgct gacgcgccct gacgggcttg tctgctcccg gcatccgctt   1320
acagacaagc tgtgaccgtc tccgggagct gcatgtgtca gaggttttca ccgtcatcac   1380
cgaaacgcgc gagacgaaag ggcctcgtga tacgcctatt tttataggtt aatgtcatga   1440
taataatggt ttcttagacg tcaggtggca cttttcgggg aaatgtgcgc ggaaccccta   1500
tttgtttatt tttctaaata cattcaaata tgtatccgct catgagacaa taaccctgat   1560
aaatgcttca ataatattga aaaggaaga gtatgagtat tcaacatttc cgtgtcgccc   1620
ttattcccctt ttttgcggca ttttgccttc ctgttttgc tcacccagaa acgctggtga   1680
aagtaaaaga tgctgaagat cagttgggtg cacgagtggg ttacatcgaa ctggatctca   1740
acagcggtaa gatccttgag agttttcgcc ccgaagaacg ttttccaatg atgagcactt   1800
ttaaagttct gctatgtggc gcggtattat cccgtattga cgccgggcaa gagcaactcg   1860
gtcgccgcat acactattct cagaatgact tggttgagta ctcaccagtc acagaaaagc   1920
atcttacgga tggcatgaca gtaagagaat tatgcagtgc tgccataacc atgagtgata   1980
acactgcggc caacttactt ctgacaacga tcggaggacc gaaggagcta accgcttttt   2040
tgcacaacat gggggatcat gtaactcgcc ttgatcgttg ggaaccggag ctgaatgaag   2100
ccataccaaa cgacgagcgt gacaccacga tgcctgtagc aatggcaaca acgttgcgca   2160
aactattaac tggcgaacta cttactctag cttcccggca acaattaata gactggatgg   2220
aggcggataa agttgcagga ccacttctgc gctcggccct tccggctggc tggtttattg   2280
ctgataaatc tggagccggt gagcgtgggt ctcgcggtat cattgcagca ctggggccag   2340
atggtaagcc ctcccgtatc gtagttatct acacgacggg gagtcaggca actatggatg   2400
aacgaaatag acagatcgct gagataggtg cctcactgat taagcattgg taactgtcag   2460
accaagttta ctcatatata ctttagattg atttaaaact tcattttaa tttaaaagga   2520
tctaggtgaa gatccttttt gataatctca tgaccaaaat cccttaacgt gagttttcgt   2580
tccactgagc gtcagacccc gtagaaaaga tcaaaggatc ttcttgagat cctttttttc   2640
tgcgcgtaat ctgctgcttg caaacaaaaa aaccaccgct accagcggtg gtttgtttgc   2700
cggatcaaga gctaccaact cttttttccga aggtaactgg cttcagcaga gcgcagatac   2760
caaatactgt ccttctagtg tagccgtagt taggccacca cttcaagaac tctgtagcac   2820
cgcctacata cctcgctctg ctaatcctgt taccagtggc tgctgccagt ggcgataagt   2880
cgtgtcttac cgggttggac tcaagacgat agttaccgga taaggcgcag cggtcgggct   2940
gaacgggggg ttcgtgcaca gcccagctt ggagcgaac gacctacacc gaactgagat    3000
acctacagcg tgagctatga gaaagcgcca cgcttcccga aggagaaag gcggacaggt   3060
atccggtaag cggcagggtc ggaacaggag agcgcacgag ggagcttcca gggggaaacg   3120
cctggtatct ttatagtcct gtcgggtttc gccacctctg acttgagcgt cgatttttgt   3180
gatgctcgtc aggggggcgg agcctatgga aaaacgccag caacgcggcc ttttacggtt   3240
cctggccttt tgctggcctt ttgctcaca tgttctttcc tgcgttatcc cctgattctg   3300
```

```
tggataaccg tattaccgcc tttgagtgag ctgataccgc tcgccgcagc cgaacgaccg    3360
agcgcagcga gtcagtgagc gaggaagcgg aaga                                3394

<210> SEQ ID NO 10
<211> LENGTH: 6220
<212> TYPE: DNA
<213> ORGANISM: Artificial Sequence
<220> FEATURE:
<223> OTHER INFORMATION: Designed plasmid DNA,
      pAC-crtMF26A,W38A,F233S-idi

<400> SEQUENCE: 10
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa agttggccc  agggcttccc     360 ggtatcaaca gggacaccag gatttattta ttctgcgaag tgatcttccg tcacaggtat     420
ttattcggcg caaagtgcgt cgggtgatgc tgccaactta ctgatttagt gtatgatggt     480 gttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg ccgcggcaa     840 agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttcaaga tttcagtgca    1440
atttatctct tcaaatgtag cacctgaagt cagccccata cgatataagt tgtaattctc    1500
atgtttgaca gcttatcgtg aggttcccg actggaaagc gggcagtgag cgcaacgcaa    1560
ttaatgtgag ttagctcact cattaggcac cccaggcttt acactttatg cttccggctc    1620
gtatgttgtg tggaattgtg agcggataac aatttcacac aggaaacaca tatgaattc    1680 tctagaagga ggattacaaa atgcaaacgg aacacgtcat tttattgaat gcacagggag    1740
ttccacgggg tacgctggaa agtatgccgc acacacggc agacaccgc ttacatctcg    1800 cgttctccag ttggctgttt aatgccaaag gacaattatt agttacccgc cgcgcactga    1860
gcaaaaaagc atggcctggc gtgtggacta actcggtttg tgggcaccca caactgggag    1920
```

```
aaagcaacga agacgcagtg atccgccgtt gccgttatga gcttggcgtg gaaattacgc    1980
ctcctgaatc tatctatcct gactttcgct accgcgccac cgatccgagt ggcattgtgg    2040
aaaatgaagt gtgtccggta tttgccgcac gcaccactag tgcgttacag atcaatgatg    2100
atgaagtgat ggattatcaa tggtgtgatt tagcagatgt attacacggt attgatgcca    2160
cgccgtgggc gttcagtccg tggatggtga tgcaggcgac aaatcgcgaa gccagaaaac    2220
gattatctgc atttacccag cttaaataac tcgaggggcc cggcgcctga tgcggtattt    2280
tctccttacg catctgtgcg gtatttcact gcatcgataa gctttaatgc ggtagtttat    2340
cacagttaaa ttgctaacgc agtcaggcac cgtgtatgaa atctaacaat gcgctcatcg    2400
tcatcctcgg caccgtcacc ctggatgctg taggcatagg cttggttatg ccggtactgc    2460
cgggcctctt gcgggatatc gtccattccg acagcatcgc cagtcactat ggcgtgctgc    2520
tagcgctata tgcgttgatg caatttctat gcgcacccgt tctcggagca ctgtccgacc    2580
gctttggccg ccgcccagtc ctgctcgctt cgctacttgg agccactatc gactacgcga    2640
tcatggcgac cacacccgtc ctgtggatcc cgtggaggtt tcccgactgg aaagcgggca    2700
gtgagcgcaa cgcaattaat gtgagttagc tcactcatta ggcacccag gctttacact    2760 ttatgcttcc ggctcgtatg ttgtgtggaa ttgtgagcgg ataacaattt cacacaggaa    2820
acacatatgg aattctctag aaggaggatt acaaaatgac aatgatgaat atgaatttta    2880
aatattgtca taaaatcatg aagaaacatt caaaaagctt ttcttacgct gcggacttgt    2940
taccagaaga tcaaagaaaa gcggttgcgg caatttatgc tgtgtgtcgt aaaattgatg    3000
acagtataga tgtttatggc gatattcaat ttttaaatca aataaaagaa gatatacaat    3060
ctattgaaaa atacccatat gaacatcatc actttcaaag tgatcgtaga atcatgatgg    3120
cgcttcagca tgttgcacaa cataaaaata tcgcctttca atctttttat aatctcattg    3180
atactgtata taaagatcaa catttttacaa tgtttgaaac ggacgctgaa ttattcggat    3240
attgttatgg tgttgctggt acagtaggtg aagtattgac gccgatttta agtgatcatg    3300
aaacacatca gacatacgat gtcgcaagaa gacttggtga atcgttgcaa ttgattaata    3360
tattaagaga tgtcggtgaa gattttgaca atgaacggat atattttagt aagcaacgat    3420
taaagcaata tgaagttgat attgctgaag tgtaccaaaa tggtgttaat aatcattata    3480
ttgacttatg ggaatattat gcagctatcg cagaaaaaga ttttcaagat gttatggatc    3540
aaatcaaagt attttagtatt gaagcacaac caatcataga attagcagca cgtatatata    3600
ttgaaatact ggacgaagtg agacaggcta actatacatt acatgaacgt gtttttgtgg    3660
ataagaggaa aaaggcaaag ttgtttcatg aaataaatag taaatatcat agaatatagc    3720
tcgaggggcc cggcgcctga tgcggtattt tctccttacg catctgtgcg gtatttcacg    3780
tgcgctcgag gggcccggcg cctgatgcgg tattttctcc ttacgcatct gtgcggtatt    3840
tcacggatcc tctacgccgg acgcatcgtg gccggcatca ccggcgccac aggtgcggtt    3900
gctggcgcct atatcgccga catcaccgat ggggaagatc gggctcgcca cttcgggctc    3960
atgagcgctt gtttcggcgt gggtatggtg gcaggccccg tggccggggg actgttgggc    4020
gccatctcct tgcatgcacc attccttgcg gcggcggtgc tcaacggcct caacctacta    4080
ctgggctgct tcctaatgca ggagtcgcat aagggagagc gtcgaccgat gcccttgaga    4140
gccttcaacc cagtcagctc cttccggtgg gcgcggggca tgactatcgt cgccgcactt    4200
atgactgtct tctttatcat gcaactcgta ggacaggtgc cggcagcgct ctgggtcatt    4260
```

```
ttcggcgagg accgctttcg ctggagcgcg acgatgatcg gcctgtcgct tgcggtattc    4320
ggaatcttgc acgccctcgc tcaagccttc gtcactggtc ccgccaccaa acgtttcggc    4380
gagaagcagg ccattatcgc cggcatggcg gccgacgcgc tgggctacgt cttgctggcg    4440
ttcgcgacgc gaggctggat ggccttcccc attatgattc ttctcgcttc cggcggcatc    4500
gggatgcccg cgttgcaggc catgctgtcc aggcaggtag atgacgacca tcagggacag    4560
cttcaaggat cgctcgcggc tcttaccagc ctaacttcga tcactggacc gctgatcgtc    4620
acggcgattt atgccgcctc ggcgagcaca tggaacgggt tggcatggat tgtaggcgcc    4680
gccctatacc ttgtctgcct ccccgcgttg cgtcgcggtg catggagccg gccaccctcg    4740
acctgaatgg aagccggcgg cacctcgcta acggattcac cactccaaga attggagcca    4800
atcaattctt gcggagaact gtgaatgcgc aaaccaaccc ttggcagaac atatccatcg    4860
cgtccgccat ctccagcagc cgcacgcggc gcatctcggg cagcgttggg tcctggccac    4920
gggtgcgcat gatcgtgctc ctgtcgttga ggacccggct aggctggcgg ggttgcctta    4980
ctggttagca gaatgaatca ccgatacgcg agcgaacgtg aagcgactgc tgctgcaaaa    5040
cgtctgcgac ctgagcaaca acatgaatgg tcttcggttt ccgtgtttcg taaagtctgg    5100
aaacgcggaa gtcccctacg tgctgctgaa gttgcccgca acagagagtg gaaccaaccg    5160
gtgataccac gatactatga ctgagagtca acgccatgag cggcctcatt tcttattctg    5220
agttacaaca gtccgcaccg ctgtccggta gctccttccg gtgggcgcgg ggcatgacta    5280
tcgtcgccgc acttatgact gtcttcttta tcatgcaact cgtaggacag gtgccggcag    5340
cgcccaacag tcccccggcc acggggcctg ccaccatacc cacgccgaaa caagcgccct    5400
gcaccattat gttccggatc tgcatcgcag gatgctgctg gctaccctgt ggaacaccta    5460
catctgtatt aacgaagcgc taaccgtttt tatcaggctc tgggaggcag aataaatgat    5520
catatcgtca attattacct ccacggggag agcctgagca aactggcctc aggcatttga    5580
gaagcacacg gtcacactgc ttccggtagt caataaaccg gtaaaccagc aatagacata    5640
agcggctatt taacgaccct gccctgaacc gacgaccggg tcgaatttgc tttcgaattt    5700
ctgccattca tccgcttatt atcacttatt caggcgtagc accaggcgtt taagggcacc    5760
aataactgcc ttaaaaaaat tacgccccgc cctgccactc atcgcagtac tgttgtaatt    5820
cattaagcat tctgccgaca tggaagccat cacagacggc atgatgaacc tgaatcgcca    5880
gcggcatcag caccttgtcg ccttgcgtat aatatttgcc catggtgaaa acggggcga    5940
agaagttgtc catattggcc acgtttaaat caaaactggt gaaactcacc cagggattgg    6000
ctgagacgaa aaacatattc tcaataaacc ctttagggaa ataggccagg ttttcaccgt    6060
aacacgccac atcttgcgaa tatatgtgta gaaactgccg gaaatcgtcg tggtattcac    6120
tccagagcga tgaaaacgtt tcagtttgct catggaaaac ggtgtaacaa gggtgaacac    6180
tatcccatat caccagctca ccgtctttca ttgccatacg                          6220
```

<210> SEQ ID NO 11
<211> LENGTH: 6565
<212> TYPE: DNA
<213> ORGANISM: Artificial Sequence
<220> FEATURE:
<223> OTHER INFORMATION: Designed plasmid DNA, pAC-fdsY81A,
      V157A-crtMF26A,W38A,F233S

<400> SEQUENCE: 11

```
gaattccgga tgagcattca tcaggcgggc aagaatgtga ataaaggccg gataaaactt      60
```

-continued

| | |
|---|---|
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa aagttggccc agggcttccc | 360 |
| ggtatcaaca gggacaccag gatttatttta ttctgcgaag tgatcttccg tcacaggtat | 420 |
| ttattcggcg caaagtgcgt cgggtgatgc tgccaactta ctgatttagt gtatgatggt | 480 |
| gttttgagg tgctccagtg gcttctgttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacaggg aagtgagagg gccgcggcaa | 840 |
| agccgttttt ccataggctc cgccccctg acaagcatca cgaaatctga cgctcaaatc | 900 |
| agtggtggcg aaacccgaca ggactataaa gataccaggc gtttccccct ggcggctccc | 960 |
| tcgtgcgctc tcctgttcct gcctttcggt ttaccggtgt cattccgctg ttatggccgc | 1020 |
| gtttgtctca ttccacgcct gacactcagt tccgggtagg cagttcgctc caagctggac | 1080 |
| tgtatgcacg aaccccccgt tcagtccgac cgctgcgcct tatccggtaa ctatcgtctt | 1140 |
| gagtccaacc cggaaagaca tgcaaaagca ccactggcag cagccactgg taattgattt | 1200 |
| agaggagtta gtcttgaagt catgcgccgg ttaaggctaa actgaaagga caagttttgg | 1260 |
| tgactgcgct cctccaagcc agttacctcg gttcaaagag ttggtagctc agagaaccttt | 1320 |
| cgaaaaccg ccctgcaagg cggttttttc gttttcagag caagagatta gcgcagacc | 1380 |
| aaaacgatct caagaagatc atcttattaa tcagataaaa tatttcaaga tttcagtgca | 1440 |
| atttatctct tcaaatgtag cacctgaagt cagccccata cgatataagt tgtaattctc | 1500 |
| atgtttgaca gcttatcgtg aggtttcccg actggaaagc gggcagtgag cgcaacgcaa | 1560 |
| ttaatgtgag ttagctcact cattaggcac cccaggcttt acactttatg cttccggctc | 1620 |
| gtatgttgtg tggaattgtg agcggataac aatttcacac aggaaacaca tatgaaattc | 1680 |
| tctagaagga ggagtaagcg atggcgcagc tttcagttga acagtttctc aacgagcaaa | 1740 |
| aacaggcggt ggaaacagcg ctctcccgtt atatagagcg cttagaaggg ccggcgaagc | 1800 |
| tgaaaaaggc gatggcgtac tcattggagg ccggcggcaa acgaatccgt ccgttgctgc | 1860 |
| ttctgtccac cgttcgggcg ctcggcaaag acccggcggt cggattgccc gtcgcctgcg | 1920 |
| cgattgaaat gatccatacg gcatctttga tccatgatga tttgccgagc atggacaacg | 1980 |
| atgatttgcg gcgcggcaag ccgacgaacc ataaagtgtt cggcgaggcg atggccatct | 2040 |
| tggcgggga cgggttgttg acgtacgcgt ttcaattgat caccgaaatc gacgatgagc | 2100 |
| gcatccctcc ttccgtccgg cttcggctca tcgaacggct ggcgaaagcg gccggtccgg | 2160 |
| aagggatggc ggccggtcag gcagccgata tggaaggaga gggaaaaacg ctgacgcttt | 2220 |
| cggagctcga atacattcat cggcataaaa ccgggaaaat gctgcaatac agcgtgcacg | 2280 |
| ccggcgcctt gatcggcggc gctgatgccc ggcaaacgcg ggagcttgac gaattcgccg | 2340 |
| cccatctagg ccttgccttt caaattcgcg atgatattct cgatattgaa ggggcagaag | 2400 |
| aaaaaatcgg caagccggtc ggcagcgacc aaagcaacaa caaagcgacg tatccagcgt | 2460 |

```
tgctgtcgct tgccggcgcg aaggaaaagt tggcgttcca tatcgaggcg gcgcagcgcc    2520
atttacggaa cgctgacgtt gacggcgccg cgctcgccta tatttgcgaa ctggtcgccg    2580
cccgcgacca ttaactcgag gggcccggcg cctgatgcgg tattttctcc ttacgcatct    2640
gtgcggtatt tcactgcatc gataagcttt aatgcggtag tttatcacag ttaaattgct    2700
aacgcagtca ggcaccgtgt atgaaatcta acaatgcgct catcgtcatc ctcggcaccg    2760
tcaccctgga tgctgtaggc ataggcttgg ttatgccggt actgccgggc ctcttgcggg    2820
atatcgtcca ttccgacagc atcgccagtc actatggcgt gctgctagcg ctatatgcgt    2880
tgatgcaatt tctatgcgca cccgttctcg gagcactgtc cgaccgcttt ggccgccgcc    2940
cagtcctgct cgcttcgcta cttggagcca ctatcgacta cgcgatcatg gcgaccacac    3000
ccgtcctgtg gatcccgtgg aggtttcccg actggaaagc gggcagtgag cgcaacgcaa    3060
ttaatgtgag ttagctcact cattaggcac cccaggcttt acactttatg cttccggctc    3120
gtatgttgtg tggaattgtg agcggataac aatttcacac aggaaacaca tatggaattc    3180
tctagaagga ggattacaaa atgacaatga tgaatatgaa ttttaaatat tgtcataaaa    3240
tcatgaagaa acattcaaaa agcttttctt acgctgcgga cttgttacca gaagatcaaa    3300
gaaaagcggt tgcggcaatt tatgctgtgt gtcgtaaaat tgatgacagt atagatgttt    3360
atggcgatat tcaattttta aatcaaataa aagaagatat acaatctatt gaaaaatacc    3420
catatgaaca tcatcacttt caaagtgatc gtagaatcat gatggcgctt cagcatgttg    3480
cacaacataa aaatatcgcc tttcaatctt tttataatct cattgatact gtatataaag    3540
atcaacattt tacaatgttt gaaacggacg ctgaattatt cggatattgt tatggtgttg    3600
ctggtacagt aggtgaagta ttgacgccga ttttaagtga tcatgaaaca catcagacat    3660
acgatgtcgc aagaagactt ggtgaatcgt tgcaattgat taatatatta agagatgtcg    3720
gtgaagattt tgacaatgaa cggatatatt ttagtaagca acgattaaag caatatgaag    3780
ttgatattgc tgaagtgtac caaaatggtg ttaataatca ttatattgac ttatgggaat    3840
attatgcagc tatcgcagaa aaagattttc aagatgttat ggatcaaatc aaagtatcta    3900
gtattgaagc acaaccaatc atagaattag cagcacgtat atatattgaa atactggacg    3960
aagtgagaca ggctaactat acattacatg aacgtgtttt tgtggataag aggaaaaagg    4020
caaagttgtt tcatgaaata aatagtaaat atcatagaat atagctcgag gggcccggcg    4080
cctgatgcgg tattttctcc ttacgcatct gtgcggtatt tcacgtgcgc tcgaggggcc    4140
cggcgcctga tgcggtattt tctccttacg catctgtgcg gtatttcacg gatcctctac    4200
gccggacgca tcgtggccgg catcaccggc gccacaggtg cggttgctgg cgcctatatc    4260
gccgacatca ccgatgggga agatcgggct cgccacttcg gctcatgagc gcttgtttc    4320 ggcgtgggta tggtggcagg ccccgtggcc gggggactgt tgggcgccat ctccttgcat    4380
gcaccattcc ttgcggcggc ggtgctcaac ggcctcaacc tactactggg ctgcttccta    4440
atgcaggagt cgcataaggg agagcgtcga ccgatgccct tgagagcctt caacccagtc    4500
agctccttcc ggtgggcgcg gggcatgact atcgtcgccg cacttatgac tgtcttcttt    4560
atcatgcaac tcgtaggaca ggtgccggca gcgctctggg tcattttcgg cgaggaccgc    4620
tttcgctgga gcgcgacgat gatcggcctg tcgcttgcgg tattcggaat cttgcacgcc    4680
ctcgctcaag ccttcgtcac tggtcccgcc accaaacgtt tcggcgagaa gcaggccatt    4740
atcgccggca tggcggccga cgcgctgggc tacgtcttgc tggcgttcgc gacgcgaggc    4800
```

```
tggatggcct tccccattat gattcttctc gcttccggcg gcatcgggat gcccgcgttg    4860
caggccatgc tgtccaggca ggtagatgac gaccatcagg gacagcttca aggatcgctc    4920
gcggctctta ccagcctaac ttcgatcact ggaccgctga tcgtcacggc gatttatgcc    4980
gcctcggcga gcacatggaa cgggttggca tggattgtag gcgccgccct ataccttgtc    5040
tgcctccccg cgttgcgtcg cggtgcatgg agccgggcca cctcgacctg aatggaagcc    5100
ggcggcacct cgctaacgga ttcaccactc caagaattgg agccaatcaa ttcttgcgga    5160
gaactgtgaa tgcgcaaacc aaccctttggc agaacatatc catcgcgtcc gccatctcca    5220
gcagccgcac gcggcgcatc tcgggcagcg ttgggtcctg gccacgggtg cgcatgatcg    5280
tgctcctgtc gttgaggacc cggctaggct ggcggggttg ccttactggt tagcagaatg    5340
aatcaccgat acgcgagcga acgtgaagcg actgctgctg caaaacgtct gcgacctgag    5400
caacaacatg aatggtcttc ggtttccgtg tttcgtaaag tctggaaacg cggaagtccc    5460
ctacgtgctg ctgaagttgc ccgcaacaga gagtggaacc aaccggtgat accacgatac    5520
tatgactgag agtcaacgcc atgagcggcc tcatttctta ttctgagtta caacagtccg    5580
caccgctgtc cggtagctcc ttccggtggg cgcggggcat gactatcgtc gccgcactta    5640
tgactgtctt ctttatcatg caactcgtag gacaggtgcc ggcagcgccc aacagtcccc    5700
cggccacggg gcctgccacc atacccacgc cgaaacaagc gccctgcacc attatgttcc    5760
ggatctgcat cgcaggatgc tgctggctac cctgtggaac acctacatct gtattaacga    5820
agcgctaacc gtttttatca ggctctggga ggcagaataa atgatcatat cgtcaattat    5880
tacctccacg gggagagcct gagcaaactg gcctcaggca tttgagaagc acacggtcac    5940
actgcttccg gtagtcaata accggtaaa ccagcaatag acataagcgg ctatttaacg    6000
accctgccct gaaccgacga ccgggtcgaa tttgctttcg aatttctgcc attcatccgc    6060
ttattatcac ttattcaggc gtagcaccag gcgtttaagg gcaccaataa ctgccttaaa    6120
aaaattacgc cccgccctgc cactcatcgc agtactgttg taattcatta agcattctgc    6180
cgacatggaa gccatcacag acggcatgat gaacctgaat cgccagcggc atcagcacct    6240
tgtcgccttg cgtataatat ttgcccatgt gaaaacgggg ggcgaagaag ttgtccatat    6300
tggccacgtt taaatcaaaa ctggtgaaac tcacccaggg attggctgag acgaaaaaca    6360
tattctcaat aaaccctttta gggaaatagg ccaggttttc accgtaacac gccacatctt    6420
gcgaatatat gtgtagaaac tgccggaaat cgtcgtggta ttcactccag agcgatgaaa    6480
acgtttcagt ttgctcatgg aaaacggtgt aacaagggtg aacactatcc catatcacca    6540
gctcaccgtc tttcattgcc atacg                                          6565
```

<210> SEQ ID NO 12
<211> LENGTH: 5044
<212> TYPE: DNA
<213> ORGANISM: Artificial Sequence
<220> FEATURE:
<223> OTHER INFORMATION: Designed plasmid DNA, pUC-pBAD-CrtI-m2

<400> SEQUENCE: 12

```
gcgcccaata cgcaaaccgc ctctccccgc gcgttggccg attcattaat gcagctggca     60
cgacaggttt cccgactgga aagcgccatg gttatgacaa cttgacggct acatcattca    120 cttttttcttc acaaccggca cggaactcgc tcgggctggc cccggtgcat ttttttaaata    180 cccgcgagaa atagagttga tcgtcaaaac caacattgcg accgacggtg gcgataggca    240
tccgggtggt gctcaaaagc agcttcgcct ggctgatacg ttggtcctcg cgccagctta    300
```

```
agacgctaat ccctaactgc tggcggaaaa gatgtgacag acgcgacggc gacaagcaaa      360
catgctgtgc gacgctggcg atatcaaaat tgctgtctgc caggtgatcg ctgatgtact      420
gacaagcctc gcgtacccga ttatccatcg gtggatggag cgactcgtta atcgcttcca      480
tgcgccgcag taacaattgc tcaagcagat ttatcgccag cagctccgaa tagcgccctt      540
ccccttgccc ggcgttaatg atttgcccaa acaggtcgct gaaatgcggc tggtgcgctt      600
catccgggcg aaagaacccc gtattggcaa atattgacgg ccagttaagc cattcatgcc      660
agtaggcgcg cggacgaaag taaacccact ggtgatacca ttcgcgagcc tccggatgac      720
gaccgtagtg atgaatctct cctggcggga acagcaaaat atcacccggt cggcaaacaa      780
attctcgtcc ctgatttttc accaccccct gaccgcgaat ggtgagattg agaatataac      840
ctttcattcc cagcggtcgg tcgataaaaa aatcgagata accgttggcc tcaatcggcg      900
ttaaacccgc caccagatgg gcattaaacg agtatcccgg cagcagggga tcattttgcg      960
cttcagccat acttttcata ctcccgccat tcagagaaga aaccaattgt ccatattgca     1020
tcagacattg ccgtcactgc gtcttttact ggctcttctc gctaaccaaa ccggtaaccc     1080
cgcttattaa aagcattctg taacaaagcg ggaccaaagc catgacaaaa acgcgtaaca     1140
aaagtgtcta taatcacggc agaaaagtcc acattgatta tttgcacggc gtcacacttt     1200
gctatgccat agcattttta tccataagat tagcggatcc tacctgacgc ttttatcgc     1260 aactctctac tgtttctcca tacccgtttg aattctctag actcgagagg aggattacaa     1320
aatgaaacca actacggtaa ttggtgcagg cttcggtggc ctggcactgg caattcgtct     1380
acaagctgcg gggatccccg tcttactgct tgaacaacgt gataaacccg gcggtcgggc     1440
ttatgtctac gaggatcagg ggtttacctt tgatgcaggc ccgacggtta tcaccgatcc     1500
cagtgccatt gaagaactgt ttgcactggc aggaaaacag ttaaagagt atgtcgaact     1560 gctgccggtt acgccgtttt accgcctgtg ttgggagtca gggaaggtct ttaattacga     1620
taacgatcaa acccggctcg aagcgcagat tcagcagttt aatccccgcg atgtcgaagg     1680
ttatcgtcag tttctggact attcacgcgc ggtgttaaa gaaggctatc taaagctcgg     1740
tactgtccct ttttttatcgt tcagagacat gcttcgcgcc gcacctcaac tggcgaaact     1800
gcaggcatgg agaagcgttt acagtaaggt tgccagttac atcgaagatg aacatctgcg     1860
ccaggcgttt tctttccact cgctgttggt gggcggcaat cccttcgcca cctcatccat     1920
ttatacgttg atacacgcgc tggagcgtga gtgggcgtc tggtttccgc gtggcggcac     1980
cggcgcatta gttcagggga tgataaagct gtttcaggat ctgggtggcg aagtcgtgtt     2040
aaacgccaga gtcagccata tggaaacgac aggaaacaag attgaagccg tgcatttaga     2100
ggacggtcgc aggttcctga cgcaagccgt cgcgtcaaat gcagatgtgg ttcatacccta     2160 tcgcgacctg ttaagccagc accctgccgc ggttaagcag tccaacaaac tgcagactaa     2220
gcgcatgagt agctctctgt ttgtgctcta ttttggtttg aatcaccatc atgatcagct     2280
cgcgcatcac acggtttgtt tcggcccgcg ttaccgcgag ctgattgacg aaattttttaa     2340 tcatgatggc ctcgcagagg acttctcact ttatctgcac gcgccctgtg tcacggattc     2400
gtcactggcg cctgaaggtt gcggcagtta ctatgtgttg gcgccggtgc cacatttagg     2460
caccgcgaac ctcgactgga cggttgaggg gccaaaacta cgcgaccgta tttttgcgta     2520
ccttgagcag cattacatgc ctggcttacg gagtcagctg gtcacgcacc ggatgtttac     2580
gccgtttgat tttcgcgacc agcttaatgc ctatcatggc tcagccttttt ctgtggagcc     2640
```

```
cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggccctgat gcggtatttt    2820
ctccttacgc atctgtgcgg tatttcacac cgcatatatg gtgcactctc agtacaatct    2880
gctctgatgc cgcatagtta agccagcccc gacacccgcc aacacccgct gacgcgccct    2940
gacgggcttg tctgctcccg gcatccgctt acagacaagc tgtgaccgtc tccgggagct    3000
gcatgtgtca gaggttttca ccgtcatcac cgaaacgcgc gagacgaaag gcctcgtga    3060 tacgcctatt tttataggtt aatgtcatga taataatggt ttcttagacg tcaggtggca    3120
cttttcgggg aaatgtgcgc ggaaccccta tttgtttatt tttctaaata cattcaaata    3180
tgtatccgct catgagacaa taaccctgat aaatgcttca ataatattga aaaggaaga    3240 gtatgagtat tcaacatttc cgtgtcgccc ttattccctt ttttgcggca ttttgccttc    3300 ctgttttgc tcacccagaa acgctggtga agtaaaaga tgctgaagat cagttgggtg    3360
cacgagtggg ttacatcgaa ctggatctca acagcggtaa gatccttgag agttttcgcc    3420
ccgaagaacg ttttccaatg atgagcactt taaagttct gctatgtggc gcggtattat    3480
cccgtattga cgccgggcaa gagcaactcg gtcgccgcat acactattct cagaatgact    3540
tggttgagta ctcaccagtc acagaaaagc atcttacgga tggcatgaca gtaagagaat    3600
tatgcagtgc tgccataacc atgagtgata acactgcggc caacttactt ctgacaacga    3660
tcggaggacc gaaggagcta accgcttttt tgcacaacat gggggatcat gtaactcgcc    3720
ttgatcgttg ggaaccggag ctgaatgaag ccataccaaa cgacgagcgt gacaccacga    3780
tgcctgtagc aatggcaaca acgttgcgca aactattaac tggcgaacta cttactctag    3840
cttcccggca acaattaata gactggatgg aggcggataa agttgcagga ccacttctgc    3900
gctcggccct tccggctggc tggtttattg ctgataaatc tggagccggt gagcgtgggt    3960
ctcgcggtat cattgcagca ctggggccag atggtaagcc ctcccgtatc gtagttatct    4020
acacgacggg gagtcaggca actatggatg aacgaaatag acagatcgct gagataggtg    4080
cctcactgat taagcattgg taactgtcag accaagttta ctcatatata ctttagattg    4140
atttaaaact tcatttttaa tttaaaagga tctaggtgaa gatcctttt gataatctca    4200 tgaccaaaat cccttaacgt gagttttcgt tccactgagc gtcagacccc gtagaaaaga    4260
tcaaaggatc ttcttgagat cctttttttc tgcgcgtaat ctgctgcttg caaacaaaaa    4320
aaccaccgct accagcggtg gtttgtttgc cggatcaaga gctaccaact cttttccga    4380 aggtaactgg cttcagcaga gcgcagatac caaatactgt ccttctagtg tagccgtagt    4440
taggccacca cttcaagaac tctgtagcac cgcctacata cctcgctctg ctaatcctgt    4500
taccagtggc tgctgccagt ggcgataagt cgtgtcttac cgggttggac tcaagacgat    4560
agttaccgga taaggcgcag cggtcgggct gaacgggggg ttcgtgcaca cagcccagct    4620
tggagcgaac gacctacacc gaactgagat acctacagcg tgagctatga aaagcgcca    4680 cgcttcccga agggagaaag gcggacaggt atccggtaag cggcagggtc ggaacaggag    4740
agcgcacgag ggagcttcca gggggaaacg cctggtatct ttatagtcct gtcgggtttc    4800
gccacctctg acttgagcgt cgatttttgt gatgctcgtc aggggggcgg agcctatgga    4860
aaaacgccag caacgcggcc tttttacggt tcctggcctt ttgctggcct tttgctcaca    4920 tgttcttttcc tgcgttatcc cctgattctg tggataaccg tattaccgcc tttgagtgag    4980
ctgataccgc tcgccgcagc cgaacgaccg agcgcagcga gtcagtgagc gaggaagcgg    5040
``` aaga                                                                  5044

<210> SEQ ID NO 13
<211> LENGTH: 6220
<212> TYPE: DNA
<213> ORGANISM: Artificial Sequence
<220> FEATURE:
<223> OTHER INFORMATION: Designed plasmid DNA, pUC-pBAD-CrtI-m2-crtY

<400> SEQUENCE: 13

```
gcgcccaata cgcaaaccgc ctctccccgc gcgttggccg attcattaat gcagctggca      60
cgacaggttt cccgactgga aagcgccatg gttatgacaa cttgacggct acatcattca     120
cttttttcttc acaaccggca cggaactcgc tcgggctggc cccgtgcat tttttaaata    180
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
cccttgccc ggcgttaatg atttgcccaa acaggtcgct gaaatgcggc tggtgcgctt     600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac      840
cttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat actttttcata ctcccgccat tcagagaaga aaccaattgt ccatattgca   1020
tcagacattg ccgtcactgc gtcttttact ggctcttctc gctaaccaaa ccggtaaccc    1080
cgcttattaa aagcattctg taacaaagcg ggaccaaagc catgacaaaa acgcgtaaca    1140
aaagtgtcta taatcacggc agaaaagtcc acattgatta tttgcacggc gtcacacttt    1200
gctatgccat agcattttta tccataagat tagcggatcc tacctgacgc tttttatcgc    1260
aactctctac tgtttctcca tacccgtttg aattctctag actcgagagg aggattacaa    1320
aatgaaacca actacggtaa ttggtgcagg cttcggtggc ctggcactgg caattcgtct    1380
acaagctgcg gggatccccg tcttactgct tgaacaacgt gataaacccg cggtcgggc     1440
ttatgtctac gaggatcagg ggtttacctt tgatgcaggc ccgacggtta tcaccgatcc    1500
cagtgccatt gaagaactgt ttgcactggc aggaaaacag ttaaaagagt atgtcgaact    1560
gctgccggtt acgccgtttt accgcctgtg ttgggagtca gggaaggtct ttaattacga    1620
taacgatcaa acccggctcg aagcgcagat tcagcagttt aatccccgcg atgtcgaagg    1680
ttatcgtcag tttctggact attcacgcgc ggtgtttaaa gaaggctatc taaagctcgg    1740
tactgtccct ttttatcgt tcagagacat gcttcgcgcc gcacctcaac tggcgaaact     1800
gcaggcatgg agaagcgttt acagtaaggt tgccagttac atcgaagatg aacatctgcg    1860
ccaggcgttt ctttccact cgctgttggt gggcggcaat ccttcgcca cctcatccat      1920
ttatacgttg atacacgcgc tggagcgtga gtgggggcgtc tggtttccgc gtggcggcac    1980
```

-continued

```
cggcgcatta gttcagggga tgataaagct gtttcaggat ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcataccta    2160
tcgcgacctg ttaagccagc accctgccgc ggttaagcag tccaacaaac tgcagactaa    2220
gcgcatgagt agctctctgt ttgtgctcta ttttggtttg aatcaccatc atgatcagct    2280
cgcgcatcac acggtttgtt tcggcccgcg ttaccgcgag ctgattgacg aaattttaa     2340 tcatgatggc ctcgcagagg acttctcact ttatctgcac gcgccctgtg tcacggattc    2400
gtcactggcg cctgaaggtt gcggcagtta ctatgtgttg gcgccggtgc cacatttagg    2460
caccgcgaac ctcgactgga cggttgaggg gccaaaacta cgcgaccgta tttttgcgta    2520
ccttgagcag cattacatgc ctggcttacg gagtcagctg gtcacgcacc ggatgtttac    2580
gccgtttgat tttcgcgacc agcttaatgc ctatcatggc tcagcctttt ctgtggagcc    2640
cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcaa ccgcattatg atctgattct cgtgggggct ggactcgcga atggccttat    2880
cgccctgcgt cttcagcagc agcaacctga tatgcgtatt ttgcttatcg acgccgcacc    2940
ccaggcgggg gggaatcata cgtggtcatt tcaccacgat gatttgactg agagccaaca    3000
tcgttggata gctccgctgg tggttcatca ctggcccgac tatcaggtac gctttcccac    3060
acgccgtcgt aagctgaaca gcggctactt ttgtattact tctcagcgtt cgctgaggt     3120 tttacagcga cagtttggcc cgcacttgtg gatggatacc gcggtcgcag aggttaatgc    3180
ggaatctgtt cggttgaaaa agggtcaggt tatcggtgcc cgcgcggtga ttgacgggcg    3240
gggttatgcg gcaaattcag cactgagcgt gggcttccag gcgtttattg ccaggaatg     3300 gcgattgagc caccccgcatg gtttatcgtc tcccattatc atggatgcca cggtcgatca    3360
gcaaaatggt tatcgcttcg tgtacagcct gccgctctcg ccgaccagat tgttaattga    3420
agacacgcac tatattgata tgcgacatt agatcctgaa tgcgcgcggc aaaatattg      3480 cgactatgcc gcgcaacagg gttggcagct tcagacactg ctgcgagaag aacagggcgc    3540
cttacccatt actctgtcgg gcaatgccga cgcattctgg cagcagcgcc ccctggcctg    3600
tagtggatta cgtgccggtc tgttccatcc taccaccggc tattcactgc cgctggcggt    3660
tgccgtggcc gaccgcctga gtgcacttga tgtctttacg tcggcctcaa ttcaccatgc    3720
cattacgcat tttgcccgcg agcgctggca gcagcagggc ttttttccgca tgctgaatcg    3780 catgctgttt ttagccggac ccgccgattc acgctggcgg gttatgcagc gttttatgg     3840 tttacctgaa gatttaattg cccgttttta tgcgggaaaa ctcacgctga ccgatcggct    3900
acgtattctg agcggcaagc cgcctgttcc ggtattagca gcattgcaag ccattatgac    3960
gactcatcgt taaactagtt gctgatgcgg tattttctcc ttacgcatct gtgcggtatt    4020
tcacaccgca tatatggtgc actctcagta caatctgctc tgatgccgca tagttaagcc    4080
agccccgaca cccgccaaca cccgctgacg cgccctgacg ggcttgtctg ctcccggcat    4140
ccgcttacag acaagctgtg accgtctccg ggagctgcat gtgtcagagg ttttcaccgt    4200
catcaccgaa acgcgcgaga cgaaagggcc tcgtgatacg cctatttttta taggttaatg    4260 tcatgataat aatggtttct tagacgtcag gtggcacttt tcggggaaat gtgcgcggaa    4320
cccctatttg tttattttc taaatacatt caaatatgta tccgctcatg agacaataac    4380
```

```
cctgataaat gcttcaataa tattgaaaaa ggaagagtat gagtattcaa catttccgtg    4440
tcgcccttat tcccttttt gcggcattt gccttcctgt tttgctcac ccagaaacgc      4500 tggtgaaagt aaaagatgct gaagatcagt tgggtgcacg agtgggttac atcgaactgg   4560
atctcaacag cggtaagatc cttgagagtt ttcgccccga agaacgtttt ccaatgatga   4620
gcacttttaa agttctgcta tgtggcgcgg tattatcccg tattgacgcc gggcaagagc   4680
aactcggtcg ccgcatacac tattctcaga atgacttggt tgagtactca ccagtcacag   4740
aaaagcatct tacggatggc atgacagtaa gagaattatg cagtgctgcc ataaccatga   4800
gtgataacac tgcggccaac ttacttctga acgatcgg aggaccgaag gagctaaccg    4860
cttttttgca caacatgggg gatcatgtaa ctcgccttga tcgttgggaa ccggagctga   4920
atgaagccat accaaacgac gagcgtgaca ccacgatgcc tgtagcaatg caacaacgt    4980 tgcgcaaact attaactggc gaactactta ctctagcttc ccggcaacaa ttaatagact   5040
ggatggaggc ggataaagtt gcaggaccac ttctgcgctc ggcccttccg gctggctggt   5100
ttattgctga taaatctgga gccggtgagc gtgggtctcg cggtatcatt gcagcactgg   5160
ggccagatgg taagccctcc cgtatcgtag ttatctacac gacggggagt caggcaacta   5220
tggatgaacg aaatagacag atcgctgaga taggtgcctc actgattaag cattggtaac   5280
tgtcagacca agtttactca tatatacttt agattgattt aaaacttcat ttttaattta   5340
aaaggatcta ggtgaagatc cttttgata atctcatgac caaaatccct aacgtgagt    5400 tttcgttcca ctgagcgtca gaccccgtag aaaagatcaa aggatcttct tgagatcctt   5460
tttttctgcg cgtaatctgc tgcttgcaaa caaaaaaacc accgctacca gcggtggttt   5520
gtttgccgga tcaagagcta ccaactcttt ttccgaaggt aactggcttc agcagagcgc   5580
agataccaaa tactgtcctt ctagtgtagc cgtagttagg ccaccacttc aagaactctg   5640
tagcaccgcc tacataccct gctctgctaa tcctgttacc agtggctgct gccagtggcg   5700
ataagtcgtg tcttaccggg ttggactcaa gacgatagtt accggataag gcgcagcggt   5760
cgggctgaac ggggggttcg tgcacacagc ccagcttgga gcaacgacc tacaccgaac     5820 tgagatacct acagcgtgag ctatgagaaa gcgccacgct tcccgaaggg agaaaggcgg   5880
acaggtatcc ggtaagcggc agggtcggaa caggagagcg cacgagggag cttccagggg   5940
gaaacgcctg gtatctttat agtcctgtcg ggtttcgcca cctctgactt gagcgtcgat   6000
ttttgtgatg ctcgtcaggg gggcggagcc tatggaaaaa cgccagcaac gcggcctttt   6060
tacggttcct ggccttttgc tggccttttg ctcacatgtt ctttcctgcg ttatcccctg   6120
attctgtgga taaccgtatt accgcctttg agtgagctga taccgctcgc cgcagccgaa   6180
cgaccgagcg cagcgagtca gtgagcgagg aagcggaaga                         6220
```

<210> SEQ ID NO 14  
<211> LENGTH: 7553  
<212> TYPE: DNA  
<213> ORGANISM: Artificial Sequence  
<220> FEATURE:  
<223> OTHER INFORMATION: Designed plasmid DNA, pUC-pBAD-CrtI-m2-crtWZY

<400> SEQUENCE: 14

```
gcgcccaata cgcaaaccgc ctctccccgc gcgttggccg attcattaat gcagctggca      60
cgacaggttt cccgactgga aagcgccatg gttatgacaa cttgacggct acatcattca    120
cttttttctc acaaccggca cggaactcgc tcgggctggc cccggtgcat ttttaaata    180
```

```
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcatttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt ttgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tcttttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaattttaa    2340
tcatgatggc ctcgcagagg acttctcact ttatctgcac gcgccctgtg tcacggattc   2400
gtcactggcg cctgaaggtt gcggcagtta ctatgtgttg gcgccggtgc cacatttagg   2460
caccgcgaac ctcgactgga cggttgaggg gccaaaacta cgcgaccgta tttttgcgta   2520
ccttgagcag cattacatgc ctggcttacg gagtcagctg gtcacgcacc ggatgtttac   2580
```

-continued

```
gccgtttgat tttcgcgacc agcttaatgc ctatcatggc tcagccttt  ctgtggagcc    2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccggcg accttgcggc    2820
gctgcgccgc gcgcctttgc tggtgcctgg gccgggtggc caatggtcgc aagcaacggg    2880
gatggaaacc ggcgatgcgg gactgtagtc tgcgcggatc gccggtccgg gggacaagat    2940
gagcgcacat gccctgccca aggcagatct gaccgccacc agcctgatcg tctcgggcgg    3000
catcatcgcc gcttggctgg ccctgcatgt gcatgcgctg tggtttctgg acgcagcggc    3060
gcatcccatc ctggcgatcg caaatttcct ggggctgacc tggctgtcgg tcggattgtt    3120
catcatcgcg catgacgcga tgcacgggtc ggtggtgccg gggcgtccgc gcgccaatgc    3180
ggcgatgggc cagcttgtcc tgtggctgta tgccggattt tcgtggcgca agatgatcgt    3240
caagcacatg gcccatcacc gccatgccgg aaccgacgac gaccccgatt tcgaccatgg    3300
cggcccggtc cgctggtacg cccgcttcat cggcacctat ttcggctggc gcgaggggct    3360
gctgctgccc gtcatcgtga cggtctatgc gctgatcctt ggggatcgct ggatgtacgt    3420
ggtcttctgg ccgctgccgt cgatcctggc gtcgatccag ctgttcgtgt tcggcacctg    3480
gctgccgcac cgccccggcc acgacgcgtt cccggaccgc cacaatgcgc ggtcgtcgcg    3540
gatcagcgac cccgtgtcgc tgctgacctg ctttcacttt ggcggttatc atcacgaaca    3600
ccacctgcac ccgacggtgc cgtggtggcg cctgcccagc acccgcacca aggggggacac    3660 cgcatgacca atttcctgat cgtcgtcgcc accgtgctgg tgatggagtt gacggcctat    3720
tccgtccacc gctggatcat gcacggcccc ctgggctggg gctggcacaa gtcccaccac    3780
gaggaacacg accacgcgct ggaaaagaac gacctgtacg gcctggtctt tgcggtgatc    3840
gccacggtgc tgttcacggt gggctggatc tgggcgccgg tcctgtggtg gatcgccttg    3900
ggcatgactg tctatgggct gatctatttc gtcctgcatg acgggctggt gcatcagcgc    3960
tggccgttcc gttatatccc gcgcaagggc tatgccagac gcctgtatca ggcccaccgc    4020
ctgcaccatg cggtcgaggg gcgcgaccat tgcgtcagct tcggcttcat ctatgcgccc    4080
ccggtcgaca agctgaagca ggacctgaag atgtcgggcg tgctgcgggc cgaggcgcag    4140
gagcgcacgt gacccatgac gtgctgctgg caggggcggg ccttgccaac gggctgatcg    4200
ccctggcgct gcgcgcggcg cggcccgacc tgcgcgtgct gctgctggac catgccgcag    4260
gaccgtcaga cggccacacc tggtcctgcc acgaccccga cctgtcgccg gactggctgg    4320
cgcggctgaa gccctgcgc cgcgccaact ggcccgacca ggaggtgcgc tttccccgcc    4380
atgcccggcg gctggccacc ggttacgggt cgctggacgg ggcggcgctg gcggatgcgg    4440
tggtccggtc gggcgccgag atccgctggg acagcgacat cgccctgctg gatgcgcagg    4500
gggcgacgcg gtcctgcggc acccggatcg aggcgggcgc ggtcctggac gggcggggcg    4560
cgcagccgtc gcggcatctg accgtggggtt tccagaaatt cgtgggtgtc gagatcgaga    4620
ccgaccgccc ccacgcgtg ccccgcccga tgatcatgga cgcgaccgtc acccagcagg    4680
acgggtaccg cttcatctat ctgctgccct tctctccgac gcgcatcctg atcgaggaca    4740
cgcgctattc cgatggcggc gatctggacg acgacgcgct ggcggcggcg tcccacgact    4800
atgcccgcca gcagggctgg accggggccg aggtccggcg cgaacgcggc atccttccca    4860
tcgcgctggc ccatgatgcg gcgggcttct gggccgatca cgcggcgggg cctgttcccg    4920
```

```
tgggactgcg cgcggggttc tttcatccgg tcaccggcta ttcgctgccc tatgcggcac    4980
aggtggcgga cgtggtggcg ggtctgtccg ggccgcccgg caccgacgcg ctgcgcggcg    5040
ccatccgcga ttacgcgatc gaccgggcgc gccgcgaccg ctttctgcgc cttttgaacc    5100
ggatgctgtt ccgcggctgc gcgcccgacc ggcgctatac cctgctgcag cggttctacc    5160
gcatgccgca tggactgatc gaacggttct atgccggccg gctgagcgtg gcggatcagc    5220
tgcgcatcgt gaccggcaag cctcccattc cccttggcac ggccatccgc tgcctgcccg    5280
aacgtcccct gctgaaggaa aacgcatgaa ctagttgatg cggtatttc tccttacgca    5340 tctgtgcggt atttcacacc gcatatatgg tgcactctca gtacaatctg ctctgatgcc    5400
gcatagttaa gccagccccg acacccgcca acacccgctg acgcgccctg acgggcttgt    5460
ctgctcccgg catccgctta cagacaagct gtgaccgtct ccgggagctg catgtgtcag    5520
aggttttcac cgtcatcacc gaaacgcgcg agacgaaagg gcctcgtgat acgcctattt    5580
ttataggtta atgtcatgat aataatggtt tcttagacgt caggtggcac ttttcgggga    5640
aatgtgcgcg gaacccctat ttgtttattt ttctaaatac attcaaatat gtatccgctc    5700
atgagacaat aaccctgata aatgcttcaa taatattgaa aaaggaagag tatgagtatt    5760
caacatttcc gtgtcgccct tattccctt tttgcggcat tttgccttcc tgttttgct    5820 cacccagaaa cgctggtgaa agtaaaagat gctgaagatc agttgggtgc acgagtgggt    5880
tacatcgaac tggatctcaa cagcggtaag atccttgaga gttttcgccc cgaagaacgt    5940
tttccaatga tgagcacttt taaagttctg ctatgtggcg cggtattatc ccgtattgac    6000
gccgggcaag agcaactcgg tcgccgcata cactattctc agaatgactt ggttgagtac    6060
tcaccagtca cagaaaagca tcttacggat ggcatgacag taagagaatt atgcagtgct    6120
gccataacca tgagtgataa cactgcggcc aacttacttc tgacaacgat cggaggaccg    6180
aaggagctaa ccgcttttt gcacaacatg ggggatcatg taactcgcct tgatcgttgg    6240
gaaccggagc tgaatgaagc cataccaaac gacgagcgtg acaccacgat gcctgtagca    6300
atggcaacaa cgttgcgcaa actattaact ggcgaactac ttactctagc ttcccggcaa    6360
caattaatag actggatgga ggcggataaa gttgcaggac cacttctgcg ctcggccctt    6420
ccggctggct ggtttattgc tgataaatct ggagccggtg agcgtgggtc tcgcggtatc    6480
attgcagcac tggggccaga tggtaagccc tcccgtatcg tagttatcta cacgacgggg    6540
agtcaggcaa ctatggatga acgaaataga cagatcgctg agataggtgc ctcactgatt    6600
aagcattggt aactgtcaga ccaagtttac tcatatatac tttagattga tttaaaactt    6660
catttttaat ttaaaaggat ctaggtgaag atcctttttg ataatctcat gaccaaaatc    6720
ccttaacgtg agttttcgtt ccactgagcg tcagaccccg tagaaaagat caaaggatct    6780
tcttgagatc ctttttttct gcgcgtaatc tgctgcttgc aaacaaaaaa accaccgcta    6840
ccagcggtgg tttgtttgcc ggatcaagag ctaccaactc tttttccgaa ggtaactggc    6900
ttcagcagag cgcagatacc aaatactgtc cttctagtgt agccgtagtt aggccaccac    6960
ttcaagaact ctgtagcacc gcctacatac ctcgctctgc taatcctgtt accagtggct    7020
gctgccagtg gcgataagtc gtgtcttacc gggttggact caagacgata gttaccggat    7080
aaggcgcagc ggtcgggctg aacggggggt tcgtgcacac agcccagctt ggagcgaacg    7140
acctacaccg aactgagata cctacagcgt gagctatgag aaagcgccac gcttcccgaa    7200
gggagaaagg cggacaggta tccggtaagc ggcagggtcg aacaggaga gcgcacgagg    7260 gagcttccag ggggaaacgc ctggtatctt tatagtcctg tcgggtttcg ccacctctga    7320
```

```
cttgagcgtc gattttttgtg atgctcgtca gggggggcgga gcctatggaa aaacgccagc      7380
aacgcggcct ttttacggtt cctggccttt tgctggcctt tgctcacat gttctttcct         7440 gcgttatccc ctgattctgt ggataaccgt attaccgcct ttgagtgagc tgataccgct         7500
cgccgcagcc gaacgaccga gcgcagcgag tcagtgagcg aggaagcgga aga              7553

<210> SEQ ID NO 15
<211> LENGTH: 5797
<212> TYPE: DNA
<213> ORGANISM: Artificial Sequence
<220> FEATURE:
<223> OTHER INFORMATION: Designed plasmid DNA, pUC-pBAD-CrtI-m2-crtA

<400> SEQUENCE: 15
gcgcccaata cgcaaaccgc ctctccccgc gcgttggccg attcattaat gcagctggca          60
cgacaggttt cccgactgga aagcgccatg gttatgacaa cttgacggct acatcattca         120 cttttttcttc acaaccggca cggaactcgc tcgggctggc cccggtgcat tttttaaata        180
cccgcgagaa atagagttga tcgtcaaaac caacattgcg accgacggtg gcgataggca         240
tccgggtggt gctcaaaagc agcttcgcct ggctgatacg ttggtcctcg cgccagctta         300
agacgctaat ccctaactgc tggcggaaaa gatgtgacag acgcgacggc gacaagcaaa         360
catgctgtgc gacgctggcg atatcaaaat tgctgtctgc caggtgatcg ctgatgtact         420
gacaagcctc gcgtacccga ttatccatcg gtggatggag cgactcgtta atcgcttcca         480
tgcgccgcag taacaattgc tcaagcagat ttatcgccag cagctccgaa tagcgccctt         540
ccccttgccc ggcgttaatg atttgcccaa acaggtcgct gaaatgcggc tggtgcgctt         600
catccgggcg aaagaacccc gtattggcaa atattgacgg ccagttaagc cattcatgcc         660
agtaggcgcg cggacgaaag taaacccact ggtgatacca ttcgcgagcc tccggatgac         720
gaccgtagtg atgaatctct cctggcggga acagcaaaat atcacccggt cggcaaacaa         780
attctcgtcc ctgattttttc accaccccct gaccgcgaat ggtgagattg agaatataac         840
ctttcattcc cagcggtcgg tcgataaaaa aatcgagata accgttggcc tcaatcggcg         900
ttaaacccgc caccagatgg gcattaaacg agtatcccgg cagcagggga tcattttgcg         960
cttcagccat acttttcata ctcccgccat tcagagaaga aaccaattgt ccatattgca        1020
tcagacattg ccgtcactgc gtcttttact ggctcttctc gctaaccaaa ccggtaaccc        1080
cgcttattaa aagcattctg taacaaagcg ggaccaaagc catgacaaaa acgcgtaaca        1140
aaagtgtcta taatcacggc agaaaagtcc acattgatta tttgcacggc gtcacacttt        1200
gctatgccat agcattttta tccataagat tagcggatcc tacctgacgc tttttatcgc        1260
aactctctac tgtttctcca tacccgtttg aattctctag actcgagagg aggattacaa        1320
aatgaaacca actacggtaa ttggtgcagg cttcggtggc ctggcactgg caattcgtct        1380
acaagctgcg gggatcccct cttactgct tgaacaacgt gataaaccg cggtcgggc          1440 ttatgtctac gaggatcagg ggtttacctt tgatgcaggc ccgacggtta tcaccgatcc        1500
cagtgccatt gaagaactgt ttgcactggc aggaaaacag ttaaagagt atgtcgaact        1560 gctgccggtt acgccgtttt accgcctgtg ttgggagtca gggaaggtct ttaattacga        1620
taacgatcaa acccggctcg aagcgcagat tcagcagttt aatcccgcg atgtcgaagg        1680 ttatcgtcag tttctggact attcacgcgc ggtgtttaaa gaaggctatc taaagctcgg        1740
tactgtccct tttttatcgt tcagagacat gcttcgcgcc gcacctcaac tggcgaaact        1800
```

```
gcaggcatgg agaagcgttt acagtaaggt tgccagttac atcgaagatg aacatctgcg    1860
ccaggcgttt tctttccact cgctgttggt gggcggcaat cccttcgcca cctcatccat    1920
ttatacgttg atacacgcgc tggagcgtga gtggggcgtc tggtttccgc gtggcggcac    1980
cggcgcatta gttcagggga tgataaagct gtttcaggat ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcatacccta   2160 tcgcgacctg ttaagccagc accctgccgc ggttaagcag tccaacaaac tgcagactaa    2220
gcgcatgagt agctctctgt tgtgctcta ttttggtttg aatcaccatc atgatcagct     2280
cgcgcatcac acggtttgtt tcggcccgcg ttaccgcgag ctgattgacg aaatttttaa    2340
tcatgatggc ctcgcagagg acttctcact ttatctgcac gcgccctgtg tcacggattc    2400
gtcactggcg cctgaaggtt gcggcagtta ctatgtgttg gcgccggtgc cacatttagg    2460
caccgcgaac ctcgactgga cggttgaggg gccaaaacta cgcgaccgta ttttgcgta    2520 ccttgagcag cattacatgc ctggcttacg gagtcagctg gtcacgcacc ggatgtttac    2580
gccgtttgat tttcgcgacc agcttaatgc ctatcatggc tcagccttt ctgtggagcc    2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcca gtcgccagcc ttagcttatt cagatttgat ggcaccagct ccctgccgtg    2880
ggtgattagc caaatgatct tgtctcgtcg tccactgaac gacgaaccgc gtgtgaagtt    2940
ctataagctg tgcggcagcg gcacgggtga gggcttcacc ccgaaaccga attggcgtgt    3000
ttgggcaatt atgcgcggcgt tcgacaccga ggcggatgca cgcgatgtca cggcaaacca    3060
tccggtttgg aaacgttggc gtgcacacgc ggcagaaacc ctggtgctgc atttgcagcc    3120
tctgtcggcc cgtggcacct ggggcggtgt gaatccgttc ctgccggagc aggtggcgga    3180
gccgagcccg gacgagccgg tcgttgcgct gacccgtgcg gcgattaaac cgcacaaagc    3240
gaatgctttt tggagccgcg tgccgaagat tagcgagaaa gttggtgaag atcagaacct    3300
gatgtttaag atcggtatcg gtgagattcc gctgtttcac caagttacgt tttccatctg    3360
gcctgatgtc gcgaaaatga acgccttcgc ccgtggtgac accccgcacg gtaaggcaat    3420
ccgcgctgcc cgcgaagagg gttggttcac ggaagaactg tacgctcgct ttcgcctgct    3480
gggcaccgag ggtagctgga tgggtaaaga cccgctggcg agcaaggttc tggaacgtga    3540
gactgcgtaa actagttgct gatgcggtat tttctcctta cgcatctgtg cggtatttca    3600
caccgcatat atggtgcact ctcagtacaa tctgctctga tgccgcatag ttaagccagc    3660
cccgacaccc gccaacaccc gctgacgcgc cctgacgggc ttgtctgctc ccggcatccg    3720
cttacagaca agctgtgacc gtctccggga gctgcatgtg tcagaggttt tcaccgtcat    3780
caccgaaacg cgcgagacga aagggcctcg tgatacgcct attttatag gttaatgtca     3840 tgataataat ggtttcttag acgtcaggtg gcacttttcg gggaaatgtg cgcggaaccc    3900
ctatttgttt attttctaa atacattcaa atatgtatcc gctcatgaga caataaccct    3960
gataaatgct tcaataatat tgaaaaagga agagtatgag tattcaacat ttccgtgtcg    4020
cccttattcc cttttttgcg gcattttgcc ttcctgtttt tgctcaccca gaaacgctgg    4080
tgaaagtaaa agatgctgaa gatcagttgg gtgcacgagt gggttacatc gaactggatc    4140
tcaacagcgg taagatcctt gagagttttc gccccgaaga acgttttcca atgatgagca    4200
```

```
cttttaaagt tctgctatgt ggcgcggtat tatcccgtat tgacgccggg caagagcaac    4260
tcggtcgccg catacactat tctcagaatg acttggttga gtactcacca gtcacagaaa    4320
agcatcttac ggatggcatg acagtaagag aattatgcag tgctgccata accatgagtg    4380
ataacactgc ggccaactta cttctgacaa cgatcggagg accgaaggag ctaaccgctt    4440
ttttgcacaa catgggggat catgtaactc gccttgatcg ttgggaaccg gagctgaatg    4500
aagccatacc aaacgacgag cgtgacacca cgatgcctgt agcaatggca acaacgttgc    4560
gcaaactatt aactggcgaa ctacttactc tagcttcccg gcaacaatta atagactgga    4620
tggaggcgga taaagttgca ggaccacttc tgcgctcggc ccttccggct ggctggttta    4680
ttgctgataa atctggagcc ggtgagcgtg gtctcgcgg tatcattgca gcactgggc     4740 cagatggtaa gccctcccgt atcgtagtta tctacacgac ggggagtcag gcaactatgg    4800
atgaacgaaa tagacagatc gctgagatag gtgcctcact gattaagcat tggtaactgt    4860
cagaccaagt ttactcatat atactttaga ttgatttaaa acttcatttt taatttaaaa    4920
ggatctaggt gaagatcctt tttgataatc tcatgaccaa aatcccttaa cgtgagtttt    4980
cgttccactg agcgtcagac cccgtagaaa agatcaaagg atcttcttga tccttttt     5040 ttctgcgcgt aatctgctgc ttgcaaacaa aaaaaccacc gctaccagcg gtggtttgtt    5100
tgccggatca agagctacca actctttttc cgaaggtaac tggcttcagc agagcgcaga    5160
taccaaatac tgtccttcta gtgtagccgt agttaggcca ccacttcaag aactctgtag    5220
caccgcctac atacctcgct ctgctaatcc tgttaccagt ggctgctgcc agtggcgata    5280
agtcgtgtct taccgggttg gactcaagac gatagttacc ggataaggcg cagcggtcgg    5340
gctgaacggg gggttcgtgc acacagccca gcttggagcg aacgacctac accgaactga    5400
gatacctaca gcgtgagcta tgagaaagcg ccacgcttcc cgaagggaga aaggcggaca    5460
ggtatccggt aagcggcagg gtcggaacag gagagcgcac gagggagctt ccaggggga    5520 acgcctggta tctttatagt cctgtcgggt ttcgccacct ctgacttgag cgtcgatttt    5580
tgtgatgctc gtcaggggg cggagcctat ggaaaaacgc cagcaacgcg gcctttttac    5640
ggttcctggc cttttgctgg ccttttgctc acatgttctt tcctgcgtta tcccctgatt    5700
ctgtggataa ccgtattacc gcctttgagt gagctgatac cgctcgccgc agccgaacga    5760
ccgagcgcag cgagtcagtg agcgaggaag cggaaga                              5797
```

<210> SEQ ID NO 16
<211> LENGTH: 6994
<212> TYPE: DNA
<213> ORGANISM: Artificial Sequence
<220> FEATURE:
<223> OTHER INFORMATION: Designed plasmid DNA,
      pUC-pBAD-CrtI-m2-CrtY-CrtWBD

<400> SEQUENCE: 16

```
gcgcccaata cgcaaaccgc ctctccccgc gcgttggccg attcattaat gcagctggca      60
cgacaggttt cccgactgga aagcgccatg ttatgacaa cttgacggct acatcattca      120 cttttcttc acaaccggca cggaactcgc tcggctggc cccggtgcat ttttaaata       180 cccgcgagaa atagagttga tcgtcaaaac caacattgcg accgacggtg gcgataggca     240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
```

```
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat actttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
aaagtgtcta taatcacggc agaaaagtcc acattgatta tttgcacggc gtcacacttt   1200
gctatgccat agcatttta tccataagat tagcggatcc tacctgacgc tttttatcgc   1260
aactctctac tgtttctcca tacccgtttg aattctctag actcgagagg aggattacaa   1320
aatgaaacca actacggtaa ttggtgcagg cttcggtggc ctggcactgg caattcgtct   1380
acaagctgcg gggatccccg tcttactgct tgaacaacgt gataaacccg gcggtcgggc   1440
ttatgtctac gaggatcagg ggtttacctt tgatgcaggc ccgacggtta tcaccgatcc   1500
cagtgccatt gaagaactgt tgcactggc aggaaaacag ttaaaagagt atgtcgaact   1560
gctgccggtt acgccgtttt accgcctgtg ttgggagtca gggaaggtct ttaattacga   1620
taacgatcaa acccggctcg aagcgcagat tcagcagttt aatccccgcg atgtcgaagg   1680
ttatcgtcag tttctggact attcacgcgc ggtgtttaaa gaaggctatc taaagctcgg   1740
tactgtccct tttttatcgt tcagagacat gcttcgcgcc gcacctcaac tggcgaaact   1800
gcaggcatgg agaagcgttt acagtaaggt tgccagttac atcgaagatg aacatctgcg   1860
ccaggcgttt tctttccact cgctgttggt gggcggcaat cccttcgcca cctcatccat   1920
ttatacgttg atacacgcgc tggagcgtga gtggggcgtc tggtttccgc gtggcggcac   1980
cggcgcatta gttcagggga tgataaagct gtttcaggat ctgggtggcg aagtcgtgtt   2040
aaacgccaga gtcagccata tggaaacgac aggaaacaag attgaagccg tgcatttaga   2100
ggacggtcgc aggttcctga cgcaagccgt cgcgtcaaat gcagatgtgg ttcataccta   2160
tcgcgacctg ttaagccagc accctgccgc ggttaagcag tccaacaaac tgcagactaa   2220
gcgcatgagt agctctctgt ttgtgctcta ttttggtttg aatcaccatc atgatcagct   2280
cgcgcatcac acggtttgtt tcggcccgcg ttaccgcgag ctgattgacg aaattttaa   2340
tcatgatggc ctcgcagagg acttctcact ttatctgcac gcgccctgtg tcacggattc   2400
gtcactggcg cctgaaggtt gcggcagtta ctatgtgttg gcgccggtgc acatttagg   2460
caccgcgaac ctcgactgga cggttgaggg gccaaaacta cgcgaccgta ttttgcgta   2520
ccttgagcag cattacatgc ctggcttacg gagtcagctg gtcacgcacc ggatgtttac   2580
gccgtttgat tttcgcgacc agcttaatgc ctatcatggc tcagccttt ctgtggagcc   2640
cgttcttacc cagagcgcct ggtttcggcc gcataaccgc gataaaacca ttactaatct   2700
ctacctggtc ggcgcaggca cgcatcccgg cgcaggcatt cctggcgtca tcggctcggc   2760
```

-continued

| | | | | | |
|---|---|---|---|---|---|
| aaaagcgaca | gcaggtttga | tgctggagga | tctgatttga | gggcccgtgt | aggaggatta | 2820 |
| caaaatgcaa | ccgcattatg | atctgattct | cgtgggggct | ggactcgcga | atggccttat | 2880 |
| cgccctgcgt | cttcagcagc | agcaacctga | tatgcgtatt | ttgcttatcg | acgccgcacc | 2940 |
| ccaggcgggc | gggaatcata | cgtggtcatt | tcaccacgat | gatttgactg | agagccaaca | 3000 |
| tcgttggata | gctccgctgg | tggttcatca | ctggcccgac | tatcaggtac | gctttcccac | 3060 |
| acgccgtcgt | aagctgaaca | gcggctactt | ttgtattact | tctcagcgtt | tcgctgaggt | 3120 |
| tttacagcga | cagtttggcc | cgcacttgtg | gatggatacc | gcggtcgcag | aggttaatgc | 3180 |
| ggaatctgtt | cggttgaaaa | agggtcaggt | tatcggtgcc | cgcgcggtga | ttgacgggcg | 3240 |
| gggttatgcg | gcaaattcag | cactgagcgt | gggcttccag | gcgtttattg | ccaggaatg | 3300 |
| gcgattgagc | cacccgcatg | gtttatcgtc | tcccattatc | atggatgcca | cggtcgatca | 3360 |
| gcaaaatggt | tatcgcttcg | tgtacagcct | gccgctctcg | ccgaccagat | tgttaattga | 3420 |
| agacacgcac | tatattgata | atgcgacatt | agatcctgaa | tgcgcgcggc | aaaatatttg | 3480 |
| cgactatgcc | gcgcaacagg | gttggcagct | tcagacactg | ctgcgagaag | aacagggcgc | 3540 |
| cttacccatt | actctgtcgg | gcaatgccga | cgcattctgg | cagcagcgcc | ccctggcctg | 3600 |
| tagtggatta | cgtgccggtc | tgttccatcc | taccaccggc | tattcactgc | cgctggcggt | 3660 |
| tgccgtggcc | gaccgcctga | gtgcacttga | tgtctttacg | tcggcctcaa | ttcaccatgc | 3720 |
| cattacgcat | tttgcccgcg | agcgctggca | gcagcagggc | ttttttccgca | tgctgaatcg | 3780 |
| catgctgttt | ttagccggac | ccgccgattc | acgctggcgg | ttatgcagc | gttttttatgg | 3840 |
| tttacctgaa | gatttaattg | cccgttttta | tgcgggaaaa | ctcacgctga | ccgatcggct | 3900 |
| acgtattctg | agcggcaagc | cgcctgttcc | ggtattagca | gcattgcaag | ccattatgac | 3960 |
| gactcatcgt | taaactagat | aactagtagg | aggattacaa | aatgaccgca | gctgtcgcag | 4020 |
| aacctcgcat | tgtaccgcgc | caaacctgga | tcggcctgac | cctggcgggt | atgattgtgg | 4080 |
| cgggctgggg | ttctctgcac | gtgtacggtg | tgtacttcca | ccgttgggc | accagcagcc | 4140 |
| tggttatcgt | cccggctatc | gtggccgttc | agacgtggtt | gtcggttggc | ctgtttattg | 4200 |
| tcgcacatga | cgccatgcac | ggttccctgg | ccccaggccg | tccgcgcctg | aacgcagcgg | 4260 |
| tgggtcgtct | gacgctgggt | ctgtatgcag | gcttccgttt | cgatcgcttg | aaaacggcgc | 4320 |
| accacgcgca | tcatgcggct | ccgggtaccg | cagatgaccc | ggacttttac | gcgcctgcgc | 4380 |
| cacgcgcctt | cctgccgtgg | ttttttgaact | ttttccgtac | ctatttcggt | tggcgcgaga | 4440 |
| tggcggttct | gaccgcgctg | gtcctgatcg | cgctgtttgg | cttgggtgcc | cgtcggcga | 4500 |
| atctgttgac | ttttttgggcc | gcaccggcgc | tgctgagcgc | gctgcaactg | ttcacgtttg | 4560 |
| gcacctggct | gccgcaccgt | cacacggacc | agccgttcgc | ggatgctcat | catgcacgca | 4620 |
| gcagcggtta | tggtccggtt | ctgagcctgc | tgacctgctt | tcatttcggt | cgtcatcacg | 4680 |
| agcaccacct | gacgccgtgg | cgtccgtggt | ggcgtttgtg | gcgtggtgaa | agctaaatcg | 4740 |
| agctttatct | agttgctgat | gcggtatttt | ctccttacgc | atctgtgcgg | tatttcacac | 4800 |
| cgcatatatg | gtgcactctc | agtacaatct | gctctgatgc | cgcatagtta | agccagcccc | 4860 |
| gacacccgcc | aacacccgct | gacgcgccct | gacgggcttg | tctgctcccg | gcatccgctt | 4920 |
| acagacaagc | tgtgaccgtc | tccgggagct | gcatgtgtca | gaggttttca | ccgtcatcac | 4980 |
| cgaaacgcgc | gagacgaaag | ggcctcgtga | tacgcctatt | tttataggtt | aatgtcatga | 5040 |
| taataatggt | ttcttagacg | tcaggtggca | cttttcgggg | aaatgtgcgc | ggaacccta | 5100 |
| tttgtttatt | tttctaaata | cattcaaata | tgtatccgct | catgagacaa | taaccctgat | 5160 |

-continued

```
aaatgcttca ataatattga aaaaggaaga gtatgagtat tcaacatttc cgtgtcgccc    5220
ttattccctt ttttgcggca ttttgccttc ctgttttttgc tcacccagaa acgctggtga    5280
aagtaaaaga tgctgaagat cagttgggtg cacgagtggg ttacatcgaa ctggatctca    5340
acagcggtaa gatccttgag agttttcgcc ccgaagaacg ttttccaatg atgagcactt    5400
ttaaagttct gctatgtggc gcggtattat cccgtattga cgccgggcaa gagcaactcg    5460
gtcgccgcat acactattct cagaatgact tggttgagta ctcaccagtc acagaaaagc    5520
atcttacgga tggcatgaca gtaagagaat tatgcagtgc tgccataacc atgagtgata    5580
acactgcggc caacttactt ctgacaacga tcggaggacc gaaggagcta accgcttttt    5640
tgcacaacat gggggatcat gtaactcgcc ttgatcgttg ggaaccggag ctgaatgaag    5700
ccataccaaa cgacgagcgt gacaccacga tgcctgtagc aatggcaaca acgttgcgca    5760
aactattaac tggcgaacta cttactctag cttcccggca acaattaata gactggatgg    5820
aggcggataa agttgcagga ccacttctgc gctcggccct tccggctggc tggtttattg    5880
ctgataaatc tggagccggt gagcgtgggt ctcgcggtat cattgcagca ctggggccag    5940
atggtaagcc ctcccgtatc gtagttatct acacgacggg gagtcaggca actatggatg    6000
aacgaaatag acagatcgct gagataggtg cctcactgat taagcattgg taactgtcag    6060
accaagttta ctcatatata ctttagattg atttaaaact tcattttttaa tttaaaagga    6120 tctaggtgaa gatcctttt gataatctca tgaccaaaat cccttaacgt gagttttcgt    6180
tccactgagc gtcagacccc gtagaaaaga tcaaaggatc ttcttgagat cctttttttc    6240
tgcgcgtaat ctgctgcttg caaacaaaaa aaccaccgct accagcggtg gtttgtttgc    6300
cggatcaaga gctaccaact cttttttccga aggtaactgg cttcagcaga gcgcagatac    6360
caaatactgt ccttctagtg tagccgtagt taggccacca cttcaagaac tctgtagcac    6420
cgcctacata cctcgctctg ctaatcctgt taccagtggc tgctgccagt ggcgataagt    6480
cgtgtcttac cgggttggac tcaagacgat agttaccgga taaggcgcag cggtcgggct    6540 gaacggggg ttcgtgcaca cagcccagct tggagcgaac gacctacacc gaactgagat    6600
acctacagcg tgagctatga gaaagcgcca cgcttcccga agggagaaag gcggacaggt    6660
atccggtaag cggcagggtc ggaacaggag agcgcacgag ggagcttcca ggggaaacg    6720 cctggtatct ttatagtcct gtcgggtttc gccacctctg acttgagcgt cgatttttgt    6780
gatgctcgtc aggggggcgg agcctatgga aaaacgccag caacgcggcc ttttacggt    6840 tcctggcctt ttgctggcct tttgctcaca tgttctttcc tgcgttatcc cctgattctg    6900
tggataaccg tattaccgcc tttgagtgag ctgataccgc tcgccgcagc cgaacgaccg    6960
agcgcagcga gtcagtgagc gaggaagcgg aaga                                 6994
```

<210> SEQ ID NO 17
<211> LENGTH: 6764
<212> TYPE: DNA
<213> ORGANISM: Artificial Sequence
<220> FEATURE:
<223> OTHER INFORMATION: Designed plasmid DNA,
      pUC-pBAD-CrtI-m2-CrtY-CrtZBD

<400> SEQUENCE: 17

```
gcgcccaata cgcaaaccgc ctctccccgc gcgttggccg attcattaat gcagctggca      60
cgacaggttt cccgactgga aagcgccatg gttatgacaa cttgacggct acatcattca     120 cttttttcttc acaaccggca cggaactcgc tcgggctggc cccggtgcat ttttaaata     180
```

```
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
cccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca    1020
tcagacattg ccgtcactgc gtcttttact ggctcttctc gctaaccaaa ccggtaaccc    1080
cgcttattaa aagcattctg taacaaagcg ggaccaaagc catgacaaaa acgcgtaaca    1140
aaagtgtcta taatcacggc agaaaagtcc acattgatta tttgcacggc gtcacacttt    1200
gctatgccat agcattttta tccataagat tagcggatcc tacctgacgc ttttatcgc    1260
aactctctac tgtttctcca tacccgtttg aattctctag actcgagagg aggattacaa    1320
aatgaaacca actacggtaa ttggtgcagg cttcggtggc ctggcactgg caattcgtct    1380
acaagctgcg gggatccccg tcttactgct tgaacaacgt gataaacccg gcggtcgggc    1440
ttatgtctac gaggatcagg ggtttacctt tgatgcaggc ccgacggtta tcaccgatcc    1500
cagtgccatt gaagaactgt ttgcactggc aggaaaacag ttaaagagt atgtcgaact    1560
gctgccggtt acgccgtttt accgcctgtg ttgggagtca gggaaggtct ttaattacga    1620
taacgatcaa acccggctcg aagcgcagat tcagcagttt aatccccgcg atgtcgaagg    1680
ttatcgtcag tttctggact attcacgcgc ggtgtttaaa gaaggctatc taaagctcgg    1740
tactgtccct tttttatcgt tcagagacat gcttcgcgcc gcacctcaac tggcgaaact    1800
gcaggcatgg agaagcgttt acagtaaggt tgccagttac atcgaagatg aacatctgcg    1860
ccaggcgttt tctttccact cgctgttggt gggcggcaat cccttcgcca cctcatccat    1920
ttatacgttg atacacgcgc tggagcgtga gtggggcgtc tggtttccgc gtggcggcac    1980
cggcgcatta gttcagggga tgataaagct gtttcaggat ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcataccta    2160
tcgcgacctg ttaagccagc accctgccgc ggttaagcag tccaacaaac tgcagactaa    2220
gcgcatgagt agctctctgt ttgtgctcta ttttggtttg aatcaccatc atgatcagct    2280
cgcgcatcac acggtttgtt tcggcccgcg ttaccgcgag ctgattgacg aaattttaa    2340
tcatgatggc ctcgcagagg acttctcact ttatctgcac gcgccctgtg tcacggattc    2400
gtcactggcg cctgaaggtt gcggcagtta ctatgtgttg gcgccggtgc cacatttagg    2460
caccgcgaac ctcgactgga cggttgaggg gccaaaacta cgcgaccgta ttttgcgta    2520
```

```
ccttgagcag cattacatgc ctggcttacg gagtcagctg gtcacgcacc ggatgtttac    2580
gccgtttgat tttcgcgacc agcttaatgc ctatcatggc tcagccttt  ctgtggagcc    2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcaa ccgcattatg atctgattct cgtgggggct ggactcgcga atggccttat    2880
cgccctgcgt cttcagcagc agcaacctga tatgcgtatt ttgcttatcg acgccgcacc    2940
ccaggcgggc gggaatcata cgtggtcatt tcaccacgat gatttgactg agagccaaca    3000
tcgttggata gctccgctgg tggttcatca ctggcccgac tatcaggtac gctttcccac    3060
acgccgtcgt aagctgaaca gcggctactt ttgtattact tctcagcgtt tcgctgaggt    3120
tttacagcga cagtttggcc cgcacttgtg gatggatacc gcggtcgcag aggttaatgc    3180
ggaatctgtt cggttgaaaa agggtcaggt tatcggtgcc cgcgcggtga ttgacgggcg    3240
gggttatgcg gcaaattcag cactgagcgt gggcttccag cgtttattg  ccaggaatg    3300 gcgattgagc cacccgcatg gtttatcgtc tcccattatc atggatgcca cggtcgatca    3360
gcaaaatggt tatcgcttcg tgtacagcct gccgctctcg ccgaccagat tgttaattga    3420
agacacgcac tatattgata atgcgacatt agatcctgaa tgcgcgcggc aaaatatttg    3480
cgactatgcc gcgcaacagg gttggcagct tcagacactg ctgcgagaag aacagggcgc    3540
cttacccatt actctgtcgg gcaatgccga cgcattctgg cagcagcgcc cctggcctg    3600 tagtggatta cgtgccggtc tgttccatcc taccaccggc tattcactgc cgctggcggt    3660
tgccgtggcc gaccgcctga gtgcacttga tgtctttacg tcggcctcaa ttcaccatgc    3720
cattacgcat tttgcccgcg agcgctggca gcagcagggc tttttccgca tgctgaatcg    3780
catgctgttt ttagccggac ccgccgattc acgctggcgg gttatgcagc gttttatgg    3840 tttacctgaa gatttaattg cccgttttta tgcgggaaaa ctcacgctga ccgatcggct    3900
acgtattctg agcggcaagc cgcctgttcc ggtattagca gcattgcaag ccattatgac    3960
gactcatcgt taaactagat aactagcgat tcactgtata acattaagaa ggaggattac    4020
aaaatggcat ggctgaccta gatcgcactg ttcctgaccg cattcctggg tatggaggct    4080
ttcgcgtgga tcatgcaccg ttatgtcatg cacggttct  tgtggtcgtg gcatcgtagc    4140
catcacgagc cgcacgacca cccgctggaa aagaacgacc tgtttgccgt tgtctttgcc    4200
gctccggcga ttgttatggt ggcggtgggt ctgcacctgt ggccttgggc cttgccggtc    4260
ggtctgggta ttactgcgta cggcatggtt tacttcttct ttcatgatgg cctggtgcat    4320
cgtcgtttcc cgacgggctt tagcggtcgc agcggctttt ggacccgtcg catccaggcg    4380
caccgtctgc accatgcagt ccgcacgcgt gagggctgcg tgtcctttgg cttcttgtgg    4440
gttcgcagcg cgcgtgccct gaaagcggaa ctggcgcaaa aacgcggtag cagcagctct    4500
ggtgcataaa agctttatct agttgctgat gcggtatttt ctccttacgc atctgtgcgg    4560
tatttcacac cgcatatatg gtgcactctc agtacaatct gctctgatgc cgcatagtta    4620
agccagcccc gacacccgcc aacacccgct gacgcgccct gacgggcttg tctgctcccg    4680
gcatccgctt acagacaagc tgtgaccgtc tccgggagct gcatgtgtca gaggttttca    4740
ccgtcatcac cgaaacgcgc gagacgaaag ggcctcgtga tacgcctatt tttataggtt    4800
aatgtcatga taataatggt ttcttagacg tcaggtggca cttttcgggg aaatgtgcgc    4860 ggaacccta  tttgtttatt tttctaaata cattcaaata tgtatccgct catgagacaa    4920
```

```
taaccctgat aaatgcttca ataatattga aaaaggaaga gtatgagtat tcaacatttc    4980
cgtgtcgccc ttattcccct ttttgcggca ttttgccttc ctgttttgc tcacccagaa     5040 acgctggtga agtaaaaga tgctgaagat cagttgggtg cacgagtggg ttacatcgaa     5100
ctggatctca acagcggtaa gatccttgag agttttcgcc ccgaagaacg ttttccaatg    5160
atgagcactt ttaaagttct gctatgtggc gcggtattat cccgtattga cgccgggcaa    5220
gagcaactcg gtcgccgcat acactattct cagaatgact tggttgagta ctcaccagtc    5280
acagaaaagc atcttacgga tggcatgaca gtaagagaat tatgcagtgc tgccataacc    5340
atgagtgata acactgcggc caacttactt ctgacaacga tcggaggacc gaaggagcta    5400
accgcttttt tgcacaacat gggggatcat gtaactcgcc ttgatcgttg ggaaccggag    5460
ctgaatgaag ccataccaaa cgacgagcgt gacaccacga tgcctgtagc aatggcaaca    5520
acgttgcgca aactattaac tggcgaacta cttactctag cttcccggca caattaata    5580 gactggatgg aggcggataa agttgcagga ccacttctgc gctcggccct tccggctggc    5640
tggtttattg ctgataaatc tggagccggt gagcgtgggt ctcgcggtat cattgcagca    5700
ctggggccag atggtaagcc ctcccgtatc gtagttatct acacgacggg gagtcaggca    5760
actatggatg aacgaaatag acagatcgct gagataggtg cctcactgat taagcattgg    5820
taactgtcag accaagttta ctcatatata ctttagattg atttaaaact tcatttttaa    5880
tttaaaagga tctaggtgaa gatcctttt gataatctca tgaccaaaat cccttaacgt    5940
gagttttcgt tccactgagc gtcagacccc gtagaaaaga tcaaaggatc ttcttgagat    6000
cctttttttc tgcgcgtaat ctgctgcttg caaacaaaaa aaccaccgct accagcggtg    6060
gtttgtttgc cggatcaaga gctaccaact cttttttccga aggtaactgg cttcagcaga    6120
gcgcagatac caaatactgt ccttctagtg tagccgtagt taggccacca cttcaagaac    6180
tctgtagcac cgcctacata cctcgctctg ctaatcctgt taccagtggc tgctgccagt    6240
ggcgataagt cgtgtcttac cgggttggac tcaagacgat agttaccgga taaggcgcag    6300
cggtcgggct gaacggggg ttcgtgcaca cagcccagct tggagcgaac gacctacacc    6360
gaactgagat acctacagcg tgagctatga gaaagcgcca cgcttcccga agggagaaag    6420
gcggacaggt atccggtaag cggcagggtc ggaacaggag agcgcacgag ggagcttcca    6480
gggggaaacg cctggtatct ttatagtcct gtcgggtttc gccacctctg acttgagcgt    6540
cgatttttgt gatgctcgtc aggggggcgg agcctatgga aaaacgccag caacgcggcc    6600 ttttttacggt tcctggcctt ttgctggcct tttgctcaca tgttctttcc tgcgttatcc    6660
cctgattctg tggataaccg tattaccgcc tttgagtgag ctgataccgc tcgccgcagc    6720
cgaacgaccg agcgcagcga gtcagtgagc gaggaagcgg aaga                    6764
```

<210> SEQ ID NO 18
<211> LENGTH: 7516
<212> TYPE: DNA
<213> ORGANISM: Artificial Sequence
<220> FEATURE:
<223> OTHER INFORMATION: Designed plasmid DNA,
      pUC-pBAD-CrtI-m2-CrtY-CrtWBD-CrtZBD

<400> SEQUENCE: 18

```
gcgcccaata cgcaaaccgc ctctccccgc gcgttggccg attcattaat gcagctggca      60
cgacaggttt cccgactgga aagcgccatg gttatgacaa cttgacggct acatcattca     120 cttttttcttc acaaccggca cggaactcgc tcgggctggc cccggtgcat ttttttaaata   180
```

```
cccgcgagaa atagagttga tcgtcaaaac caacattgcg accgacggtg gcgataggca    240
tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540 cccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac    840 cttctcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca    1020
tcagacattg ccgtcactgc gtctttact ggctcttctc gctaaccaaa ccggtaaccc    1080
cgcttattaa aagcattctg taacaaagcg ggaccaaagc catgacaaaa acgcgtaaca    1140
aaagtgtcta taatcacggc agaaaagtcc acattgatta tttgcacggc gtcacacttt    1200
gctatgccat agcatttta tccataagat tagcggatcc tacctgacgc ttttatcgc    1260 aactctctac tgtttctcca tacccgtttg aattctctag actcgagagg aggattacaa    1320
aatgaaacca actacggtaa ttggtgcagg cttcggtggc ctggcactgg caattcgtct    1380
acaagctgcg gggatccccg tcttactgct tgaacaacgt gataaacccg gcggtcgggc    1440
ttatgtctac gaggatcagg ggtttacctt tgatgcaggc ccgacggtta tcaccgatcc    1500
cagtgccatt gaagaactgt ttgcactggc aggaaaacag ttaaagagt atgtcgaact    1560 gctgccggtt acgccgtttt accgcctgtg ttgggagtca gggaaggtct ttaattacga    1620
taacgatcaa acccggctcg aagcgcagat tcagcagttt aatccccgcg atgtcgaagg    1680
ttatcgtcag tttctggact attcacgcgc ggtgttaaa gaaggctatc taaagctcgg    1740
tactgtccct ttttatcgt tcagagacat gcttcgcgcc gcacctcaac tggcgaaact    1800
gcaggcatgg agaagcgttt acagtaaggt tgccagttac atcgaagatg aacatctgcg    1860
ccaggcgttt tcttttcact cgctgttggt gggcggcaat cccttcgcca cctcatccat    1920
ttatacgttg atacacgcgc tggagcgtga gtggggcgtc tggtttccgc gtggcggcac    1980
cggcgcatta gttcagggga tgataaagct gtttcaggat ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcataccta    2160
tcgcgacctg ttaagccagc accctgccgc ggttaagcag tccaacaaac tgcagactaa    2220
gcgcatgagt agctctctgt tgtgctcta ttttggtttg aatcaccatc atgatcagct    2280
cgcgcatcac acggtttgtt tcggcccgcg ttaccgcgag ctgattgacg aaattttaa    2340 tcatgatggc ctcgcagagg acttctcact ttatctgcac gcgccctgtg tcacggattc    2400
gtcactggcg cctgaaggtt gcggcagtta ctatgtgttg gcgccggtgc acatttagg    2460 caccgcgaac ctcgactgga cggttgaggg gccaaaacta cgcgaccgta tttttgcgta    2520
```

```
ccttgagcag cattacatgc ctggcttacg gagtcagctg gtcacgcacc ggatgtttac    2580
gccgtttgat tttcgcgacc agcttaatgc ctatcatggc tcagccttt  ctgtggagcc    2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcaa ccgcattatg atctgattct cgtgggggct ggactcgcga atggccttat    2880
cgccctgcgt cttcagcagc agcaacctga tatgcgtatt ttgcttatcg acgccgcacc    2940
ccaggcgggc gggaatcata cgtggtcatt tcaccacgat gatttgactg agagccaaca    3000
tcgttggata gctccgctgg tggttcatca ctggcccgac tatcaggtac gctttcccac    3060
acgccgtcgt aagctgaaca gcggctactt ttgtattact tctcagcgtt cgctgaggt     3120 tttacagcga cagtttggcc cgcacttgtg gatggatacc gcggtcgcag aggttaatgc    3180
ggaatctgtt cggttgaaaa agggtcaggt tatcggtgcc cgcgcggtga ttgacgggcg    3240
gggttatgcg gcaaattcag cactgagcgt gggcttccag gcgttattg  gccaggaatg    3300 gcgattgagc cacccgcatg gtttatcgtc tcccattatc atggatgcca cggtcgatca    3360
gcaaaatggt tatcgcttcg tgtacagcct gccgctctcg ccgaccagat tgttaattga    3420
agacacgcac tatattgata atgcgacatt agatcctgaa tgcgcgcggc aaaatatttg    3480
cgactatgcc gcgcaacagg gttggcagct tcagacactg ctgcgagaag aacagggcgc    3540
cttacccatt actctgtcgg gcaatgccga cgcattctgg cagcagcgcc cctggcctg    3600 tagtggatta cgtgccggtc tgttccatcc taccaccggc tattcactgc cgctggcggt    3660
tgccgtggcc gaccgcctga gtgcacttga tgtctttacg tcggcctcaa ttcaccatgc    3720
cattacgcat tttgcccgcg agcgctggca gcagcagggc tttttccgca tgctgaatcg    3780
catgctgttt ttagccggac ccgccgattc acgctggcgg gttatgcagc gttttatgg    3840 tttacctgaa gatttaattg cccgttttta tgcgggaaaa ctcacgctga ccgatcggct    3900
acgtattctg agcggcaagc cgcctgttcc ggtattagca gcattgcaag ccattatgac    3960
gactcatcgt taaactagat aactagtagg aggattacaa aatgaccgca gctgtcgcag    4020
aacctcgcat tgtaccgcgc caaacctgga tcggcctgac cctggcgggt atgattgtgg    4080
cgggctgggg ttctctgcac gtgtacggtg tgtacttcca ccgttggggc accagcagcc    4140
tggttatcgt cccggctatc gtggccgttc agacgtggtt gtcggttggc ctgtttattg    4200
tcgcacatga cgccatgcac ggttccctgg ccccaggccg tccgcgcctg aacgcagcgg    4260
tgggtcgtct gacgctgggt ctgtatgcag gcttccgttt cgatcgcttg aaaacggcgc    4320
accacgcgca tcatgcggct ccgggtaccg cagatgaccc ggacttttac gcgcctgcgc    4380
cacgcgcctt cctgccgtgg ttttttgaact ttttccgtac ctatttcggt tggcgcgaga    4440
tggcggttct gaccgcgctg gtcctgatcg cgctgtttgg cttgggtgcc cgtccggcga    4500
atctgttgac ttttttgggcc gcaccggcgc tgctgagcgc gctgcaactg ttcacgtttg    4560
gcacctggct gccgcaccgt cacacggacc agccgttcgc ggatgctcat catgcacgca    4620
gcagcggtta tggtccggtt ctgagcctgc tgacctgctt tcatttcggt cgtcatcacg    4680
agcaccacct gacgccgtgg cgtccgtggt ggcgtttgtg gcgtggtgaa agctaaatcg    4740
attcactgta taacattaag aaggaggatt acaaaatggc atggctgacc tggatcgcac    4800
tgttcctgac cgcattcctg ggtatggagg ctttcgcgtg gatcatgcac cgttatgtca    4860
tgcacggttt cttgtggtcg tggcatcgta gccatcacga gccgcacgac cacccgctgg    4920
```

| | |
|---|---|
| aaaagaacga cctgtttgcc gttgtctttg ccgctccggc gattgttatg gtggcggtgg | 4980 |
| gtctgcacct gtggccttgg gccttgccgg tcggtctggg tattactgcg tacggcatgg | 5040 |
| tttacttctt cttcatgat ggcctggtgc atcgtcgttt cccgacgggc tttagcggtc | 5100 |
| gcagcggctt ttggacccgt cgcatccagg cgcaccgtct gcaccatgca gtccgcacgc | 5160 |
| gtgagggctg cgtgtccttt ggcttcttgt gggttcgcag cgcgcgtgcc ctgaaagcgg | 5220 |
| aactggcgca aaaacgcggt agcagcagct ctggtgcata aaagctttat ctagttgctg | 5280 |
| atgcggtatt ttctccttac gcatctgtgc ggtatttcac accgcatata tggtgcactc | 5340 |
| tcagtacaat ctgctctgat gccgcatagt taagccagcc ccgacacccg ccaacacccg | 5400 |
| ctgacgcgcc ctgacgggct tgtctgctcc cggcatccgc ttacagacaa gctgtgaccg | 5460 |
| tctccgggag ctgcatgtgt cagaggtttt caccgtcatc accgaaacgc gcgagacgaa | 5520 |
| agggcctcgt gatacgccta ttttataggt taatgtcat gataataatg gtttcttaga | 5580 |
| cgtcaggtgg cacttttcgg ggaaatgtgc gcggaacccc tatttgttta tttttctaaa | 5640 |
| tacattcaaa tatgtatccg ctcatgagac aataaccctg ataaatgctt caataatatt | 5700 |
| gaaaaaggaa gagtatgagt attcaacatt tccgtgtcgc ccttattccc ttttttgcgg | 5760 |
| cattttgcct tcctgttttt gctcacccag aaacgctggt gaaagtaaaa gatgctgaag | 5820 |
| atcagttggg tgcacgagtg ggttacatcg aactggatct caacagcggt aagatccttg | 5880 |
| agagttttcg ccccgaagaa cgttttccaa tgatgagcac ttttaaagtt ctgctatgtg | 5940 |
| gcgcggtatt atcccgtatt gacgccgggc aagagcaact cggtcgccgc atacactatt | 6000 |
| ctcagaatga cttggttgag tactcaccag tcacagaaaa gcatcttacg gatggcatga | 6060 |
| cagtaagaga attatgcagt gctgccataa ccatgagtga taacactgcg gccaacttac | 6120 |
| ttctgacaac gatcggagga ccgaaggagc taaccgcttt tttgcacaac atggggatc | 6180 |
| atgtaactcg ccttgatcgt tgggaaccgg agctgaatga agccatacca aacgacgagc | 6240 |
| gtgacaccac gatgcctgta gcaatggcaa caacgttgcg caaactatta actggcgaac | 6300 |
| tacttactct agcttcccgg caacaattaa tagactggat ggaggcggat aaagttgcag | 6360 |
| gaccacttct gcgctcggcc cttccggctg gctggtttat tgctgataaa tctggagccg | 6420 |
| gtgagcgtgg gtctcgcggt atcattgcag cactggggcc agatggtaag ccctcccgta | 6480 |
| tcgtagttat ctacacgacg gggagtcagg caactatgga tgaacgaaat agacagatcg | 6540 |
| ctgagatagg tgcctcactg attaagcatt ggtaactgtc agaccaagtt tactcatata | 6600 |
| tactttagat tgatttaaaa cttcattttt aatttaaaag gatctaggtg aagatccttt | 6660 |
| ttgataatct catgaccaaa atcccttaac gtgagttttc gttccactga gcgtcagacc | 6720 |
| ccgtagaaaa gatcaaagga tcttcttgag atcctttttt tctgcgcgta atctgctgct | 6780 |
| tgcaaacaaa aaaaccaccg ctaccagcgg tggtttgttt gccggatcaa gagctaccaa | 6840 |
| ctcttttccc gaaggtaact ggcttcagca gagcgcagat accaaatact gtccttctag | 6900 |
| tgtagccgta gttaggccac cacttcaaga actctgtagc accgcctaca tacctcgctc | 6960 |
| tgctaatcct gttaccagtg gctgctgcca gtggcgataa gtcgtgtctt accgggttgg | 7020 |
| actcaagacg atagttaccg gataaggcgc agcggtcggg ctgaacgggg gttcgtgca | 7080 |
| cacagcccag cttggagcga acgacctaca ccgaactgag atacctacag cgtgagctat | 7140 |
| gagaaagcgc cacgcttccc gaagggagaa aggcggacag gtatccggta agcggcaggg | 7200 |
| tcggaacagg agagcgcacg agggagcttc caggggaaa cgcctggtat ctttatagtc | 7260 |

```
ctgtcgggtt tcgccacctc tgacttgagc gtcgattttt gtgatgctcg tcagggggc    7320 ggagcctatg gaaaaacgcc agcaacgcgg cctttttacg gttcctggcc ttttgctggc    7380
cttttgctca catgttcttt cctgcgttat ccctgattc tgtggataac cgtattaccg    7440
cctttgagtg agctgatacc gctcgccgca gccgaacgac cgagcgcagc gagtcagtga    7500
gcgaggaagc ggaaga                                                    7516

<210> SEQ ID NO 19
<211> LENGTH: 7359
<212> TYPE: DNA
<213> ORGANISM: Artificial Sequence
<220> FEATURE:
<223> OTHER INFORMATION: Designed plasmid DNA,
      pAC-crtMF26A,W38A,F233S-fdsY81A,V157A-idi

<400> SEQUENCE: 19
gaattccgga tgagcattca tcaggcgggc aagaatgtga ataaaggccg gataaaactt     60
gtgcttattt tctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc    360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480 gttttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccctg gcggctccct    960 cgtgcgctct cctgttcctg cctttcggtt taccggtgtc attccgctgt tatggccgcg   1020
tttgtctcat tccacgcctg acactcagtt ccgggtaggc agttcgctcc aagctggact   1080
gtatgcacga accccccgtt cagtccgacc gctgcgcctt atccggtaac tatcgtcttg   1140
agtccaaccc ggaaagacat gcaaaagcac actggcagc agccactggt aattgattta   1200
gaggagttag tcttgaagtc atgcgccggt taaggctaaa ctgaaggac aagttttggt   1260 gactgcgctc ctccaagcca gttacctcgg ttcaaagagt tggtagctca gagaaccttc   1320
gaaaaaccgc cctgcaaggc ggttttttcg ttttcagagc aagagattac gcgcagacca   1380
aaacgatctc aagaagatca tcttattaat cagataaaat atttcaagat ttcagtgcaa   1440
tttatctctt caaatgtagc acctgaagtc agccccatac gataagttg gtaattctca   1500 tgtttgacag cttatcgtga ggtttcccga ctggaaagcg ggcagtgagc gcaacgcaat   1560
taatgtgagt tagctcactc attaggcacc ccaggcttta cactttatgc ttccggctcg   1620
tatgttgtgt ggaattgtga gcggataaca atttcacaca ggaaacacat atggaattct   1680
ctagaaggag gagtaagcga tggcgcagct ttcagttgaa cagtttctca acgagcaaaa   1740
```

```
acaggcggtg gaaacagcgc tctcccgtta tatagagcgc ttagaagggc cggcgaagct   1800
gaaaaaggcg atggcgtact cattggaggc cggcggcaaa cgaatccgtc cgttgctgct   1860
tctgtccacc gttcgggcgc tcggcaaaga cccggcggtc ggattgcccg tcgcctgcgc   1920
gattgaaatg atccatacgg catctttgat ccatgatgat ttgccgagca tggacaacga   1980
tgatttgcgg cgcggcaagc cgacgaacca taaagtgttc ggcgaggcga tggccatctt   2040
ggcgggggac gggttgttga cgtacgcgtt tcaattgatc accgaaatcg acgatgagcg   2100
catccctcct tccgtccggc ttcggctcat cgaacggctg gcgaaagcgg ccggtccgga   2160
agggatggcg gccggtcagg cagccgatat ggaaggagag gggaaaacgc tgacgctttc   2220
ggagctcgaa tacattcatc ggcataaaac cgggaaaatg ctgcaataca gcgtgcacgc   2280
cggcgccttg atcggcggcg ctgatgcccg gcaaacgcgg gagcttgacg aattcgccgc   2340
ccatctaggc cttgcctttc aaattcgcga tgatattctc gatattgaag gggcagaaga   2400
aaaaatcggc aagccggtcg gcagcgacca aagcaacaac aaagcgacgt atccagcgtt   2460
gctgtcgctt gccggcgcga aggaaaagtt ggcgttccat atcgaggcgg cgcagcgcca   2520
tttacggaac gctgacgttg acggcgccgc gctcgcctat atttgcgaac tggtcgccgc   2580
ccgcgaccat taactcgagg ggcccggcgc ctgatgcggt attttctcct tacgcatctg   2640
tgcggtattt cactgcatcg ataagcttta atgcggtagt ttatcacagt taaattgcta   2700
acgcagtcag gcaccgtgta tgaaatctaa caatgcgctc atcgtcatcc tcggcaccgt   2760
caccctggat gctgtaggca taggcttggt tatgccggta ctgccgggcc tcttgcggga   2820
tatcgtccat tccgacagca tcgccagtca ctatggcgtg ctgctagcgc tatatgcgtt   2880
gatgcaattt ctatgcgcac ccgttctcgg agcactgtcc gaccgctttg gccgccgccc   2940
agtcctgctc gcttcgctac ttggagccac tatcgactac gcgatcatgg cgaccacacc   3000
cgtcctgtgg atcccgtgga ggtttcccga ctggaaagcg ggcagtgagc gcaacgcaat   3060
taatgtgagt tagctcactc attaggcacc ccaggcttta ctttatgc ttccggctcg   3120 tatgttgtgt ggaattgtga gcggataaca atttcacaca ggaaacacat atggaattct   3180
ctagaaggag gattacaaaa tgacaatgat gaatatgaat tttaaatatt gtcataaaat   3240
catgaagaaa cattcaaaaa gcttttctta cgctgcggac ttgttaccag aagatcaaag   3300
aaaagcggtt gcggcaattt atgctgtgtg tcgtaaaatt gatgacagta tagatgttta   3360
tggcgatatt caattttaa atcaaataaa agaagatata caatctattg aaaaataccc   3420
atatgaacat catcactttc aaagtgatcg tagaatcatg atggcgcttc agcatgttgc   3480
acaacataaa aatatcgcct ttcaatcttt ttataatctc attgatactg tatataaaga   3540
tcaacatttt acaatgtttg aaacggacgc tgaattattc ggatattgtt atggtgttgc   3600
tggtacagta ggtgaagtat tgacgccgat tttaagtgat catgaaacac atcagacata   3660
cgatgtcgca agaagacttg gtgaatcgtt gcaattgatt aatatattaa gagatgtcgg   3720
tgaagatttt gacaatgaac ggatatattt tagtaagcaa cgattaaagc aatatgaagt   3780
tgatattgct gaagtgtacc aaaatggtgt taataatcat tatattgact tatgggaata   3840
ttatgcagct atcgcagaaa aagatttca agatgttatg gatcaaatca agtatctag   3900 tattgaagca caaccaatca tagaattagc agcacgtata tatattgaaa tactggacga   3960
agtgagacag gctaactata cattacatga acgtgttttt gtggataaga ggaaaaaggc   4020
aaagttgttt catgaaataa atagtaaata tcatagaata tagctcgagg ggcccggcgc   4080
ctgatgcggt attttctcct tacgcatctg tgcggtattt cactgcgct cgagggggccc   4140
```

```
ggcgcctgat gcggtatttt ctccttacgc atctgtgcgg tatttcacgg atcctctacg    4200
ccggacgcat cgtggccggc atcaccggcg ccacaggtgc ggttgctggc gcctatatcg    4260
ccgacatcac cgatggggaa gatcgggctc gccacttcgg gctcatgagc gcttgtttcg    4320
gcgtgggtat ggtggcaggc cccgtggccg ggggactgtt gggcgccatc tccttgcatg    4380
caccattcct tgcggcggcg gtgctcaacg gcctcaacct actactgggc tgcttcctaa    4440
tgcaggagtc gcataaggga gagcgtcgac gtgaaatacc gcacagatgc gtaaggagaa    4500
aataccgcat caggcgccgg gcccctcgag ttatttaagc tgggtaaatg cagataatcg    4560
ttttctggct tcgcgatttg tcgcctgcat caccatccac ggactgaacg cccacggcgt    4620
ggcatcaata ccgtgtaata catctgctaa atcacaccat tgataatcca tcacttcatc    4680
atcattgatc tgtaacgcac tagtggtgcg tgcggcaaat accggacaca cttcattttc    4740
cacaatgcca ctcggatcgg tggcgcggta gcgaaagtca ggatagatag attcaggagg    4800
cgtaatttcc acgccaagct cataacggca acggcggatc actgcgtctt cgttgctttc    4860
tcccagttgt gggtgcccac aaaccgagtt agtccacacg ccaggccatg cttttttgct    4920
cagtgcgcgg cgggtaacta ataattgtcc tttggcatta aacagccaac tggagaacgc    4980
gagatgtaag cgggtgtctg ccgtgtgtgc ggcatacttt tccagcgtac ccgtgggaac    5040
tccctgtgca ttcaataaaa tgacgtgttc cgtttgcatt ttgtaatcct ccttctagag    5100
aattccatat gtgtttcctg tgtgaaattg ttatccgctc acaattccac acaacatacg    5160
agccggaagc ataaagtgta aagcctgggg tgcctaatga gtgagctaac tcacattaat    5220
tgcgttgcgc tcactgcccg ctttccagtc gggaaacctg tcgaccgatg cccttgagag    5280
ccttcaaccc agtcagctcc ttccggtggg cgcggggcat gactatcgtc gccgcactta    5340
tgactgtctt ctttatcatg caactcgtag gacaggtgcc ggcagcgctc tgggtcattt    5400
tcggcgagga ccgctttcgc tggagcgcga cgatgatcgg cctgtcgctt gcggtattcg    5460
gaatcttgca cgccctcgct caagccttcg tcactggtcc cgccaccaaa cgtttcggcg    5520
agaagcaggc cattatcgcc ggcatggcgg ccgacgcgct gggctacgtc ttgctggcgt    5580
tcgcgacgcg aggctggatg gccttcccca ttatgattct tctcgcttcc ggcggcatcg    5640
ggatgcccgc gttgcaggcc atgctgtcca ggcaggtaga tgacgaccat cagggacagc    5700
ttcaaggatc gctcgcggct cttaccagcc taacttcgat cactggaccg ctgatcgtca    5760
cggcgattta tgccgcctcg gcgagcacat ggaacgggtt ggcatggatt gtaggcgccg    5820
ccctatacct tgtctgcctc cccgcgttgc gtcgcggtgc atggagccgg gccacctcga    5880
cctgaatgga agccggcggc acctcgctaa cggattcacc actccaagaa ttggagccaa    5940
tcaattcttg cggagaactg tgaatgcgca aaccaaccct tggcagaaca tatccatcgc    6000
gtccgccatc tccagcagcc gcacgcggcg catctcgggc agcgttgggt cctggccacg    6060
ggtgcgcatg atcgtgctcc tgtcgttgag gacccggcta ggctggcggg gttgccttac    6120
tggttagcag aatgaatcac cgatacgcga gcgaacgtga agcgactgct gctgcaaaac    6180
gtctgcgacc tgagcaacaa catgaatggt cttcggtttc cgtgtttcgt aaagtctgga    6240
aacgcggaag tcccctacgt gctgctgaag ttgcccgcaa cagagagtgg aaccaaccgg    6300
tgataccacg atactatgac tgagagtcaa cgccatgagc ggcctcattt cttattctga    6360
gttacaacag tccgcaccgc tgtccggtag ctccttccgg tgggcgcggg gcatgactat    6420
cgtcgccgca cttatgactg tcttctttat catgcaactc gtaggacagg tgccggcagc    6480
```

```
gcccaacagt ccccccggcca cggggcctgc caccatacccc acgccgaaac aagcgccctg    6540
caccattatg ttccggatct gcatcgcagg atgctgctgg ctaccctgtg gaacacctac    6600
atctgtatta acgaagcgct aaccgttttt atcaggctct gggaggcaga ataaatgatc    6660
atatcgtcaa ttattacctc cacggggaga gcctgagcaa actggcctca ggcatttgag    6720
aagcacacgg tcacactgct tccggtagtc aataaaccgg taaaccagca atagacataa    6780
gcggctattt aacgaccctg ccctgaaccg acgaccgggt cgaatttgct ttcgaatttc    6840
tgccattcat ccgcttatta tcacttattc aggcgtagca ccaggcgttt aagggcacca    6900
ataactgcct taaaaaaatt acgccccgcc ctgccactca tcgcagtact gttgtaattc    6960
attaagcatt ctgccgacat ggaagccatc acagacggca tgatgaacct gaatcgccag    7020
cggcatcagc accttgtcgc cttgcgtata atatttgccc atggtgaaaa cggggggcgaa    7080 gaagttgtcc atattggcca cgtttaaatc aaaactggtg aaactcaccc agggattggc    7140
tgagacgaaa aacatattct caataaaccc tttagggaaa taggccaggt tttcaccgta    7200
acacgccaca tcttgcgaat atatgtgtag aaactgccgg aaatcgtcgt ggtattcact    7260
ccagagcgat gaaaacgttt cagtttgctc atggaaaacg gtgtaacaag ggtgaacact    7320
atcccatatc accagctcac cgtctttcat tgccatacg                           7359

<210> SEQ ID NO 20
<211> LENGTH: 7561
<212> TYPE: DNA
<213> ORGANISM: Artificial
<220> FEATURE:
<223> OTHER INFORMATION: Designed plasmid DNA,
      pUC-pBAD-CrtIN304P-CrtY-CrtG-CrtZBD

<400> SEQUENCE: 20
gcgcccaata cgcaaaccgc ctctccccgc gcgttggccg attcattaat gcagctggca      60
cgacaggttt cccgactgga aagcgccatg gttatgacaa cttgacggct acatcattca     120 cttttcttc acaaccggca cggaactcgc tcgggctggc cccggtgcat ttttaaata     180 cccgcgagaa atagagttga tcgtcaaaac caacattgcg accgacggtg gcgataggca     240
tccgggtggt gctcaaaagc agcttcgcct ggctgatacg ttggtcctcg cgccagctta     300
agacgctaat ccctaactgc tggcggaaaa gatgtgacag acgcgacggc gacaagcaaa     360
catgctgtgc gacgctggcg atatcaaaat tgctgtctgc caggtgatcg ctgatgtact     420
gacaagcctc gcgtacccga ttatccatcg gtggatggag cgactcgtta atcgcttcca     480
tgcgccgcag taacaattgc tcaagcagat ttatcgccag cagctccgaa tagcgccctt     540 cccccttgccc ggcgttaatg atttgcccaa acaggtcgct gaaatgcggc tggtgcgctt     600
catccgggcg aaagaacccc gtattggcaa atattgacgg ccagttaagc cattcatgcc     660
agtaggcgcg cggacgaaag taaacccact ggtgatacca ttcgcgagcc tccggatgac     720
gaccgtagtg atgaatctct cctggcggga acagcaaaat atcacccggt cggcaaacaa     780
attctcgtcc ctgattttc accacccct gaccgcgaat ggtgagattg agaatataac     840
ctttcattcc cagcggtcgg tcgataaaaa aatcgagata accgttggcc tcaatcggcg     900
ttaaacccgc caccagatgg gcattaaacg agtatcccgg cagcagggga tcattttgcg     960
cttcagccat acttttcata ctcccgccat tcagagaaga aaccaattgt ccatattgca    1020
tcagacattg ccgtcactgc gtcttttact ggctcttctc gctaaccaaa ccggtaaccc    1080
cgcttattaa aagcattctg taacaaagcg ggaccaaagc catgacaaaa acgcgtaaca    1140
```

| | | | | | |
|---|---|---|---|---|---|
| aaagtgtcta | taatcacggc | agaaaagtcc | acattgatta | tttgcacggc | gtcacacttt | 1200 |
| gctatgccat | agcattttta | tccataagat | tagcggatcc | tacctgacgc | tttttatcgc | 1260 |
| aactctctac | tgtttctcca | tacccgtttg | aattctctag | actcgagagg | aggattacaa | 1320 |
| aatgaaacca | actacggtaa | ttggtgcagg | cttcggtggc | ctggcactgg | caattcgtct | 1380 |
| acaagctgcg | gggatccccg | tcttactgct | tgaacaacgt | gataaacccg | gcggtcgggc | 1440 |
| ttatgtctac | gaggatcagg | ggtttacctt | tgatgcaggc | ccgacggtta | tcaccgatcc | 1500 |
| cagtgccatt | gaagaactgt | tgcactggca | aggaaaacag | ttaaaagagt | atgtcgaact | 1560 |
| gctgccggtt | acgccgtttt | accgcctgtg | ttgggagtca | gggaaggtct | ttaattacga | 1620 |
| taacgatcaa | acccggctcg | aagcgcagat | tcagcagttt | aatccccgcg | atgtcgaagg | 1680 |
| ttatcgtcag | tttctggact | attcacgcgc | ggtgtttaaa | gaaggctatc | taaagctcgg | 1740 |
| tactgtccct | tttttatcgt | tcagagacat | gcttcgcgcc | gcacctcaac | tggcgaaact | 1800 |
| gcaggcatgg | agaagcgttt | acagtaaggt | tgccagttac | atcgaagatg | aacatctgcg | 1860 |
| ccaggcgttt | tctttccact | cgctgttggt | gggcggcaat | cccttcgcca | cctcatccat | 1920 |
| ttatacgttg | atacacgcgc | tggagcgtga | gtggggcgtc | tggtttccgc | gtggcggcac | 1980 |
| cggcgcatta | gttcagggga | tgataaagct | gtttcaggat | ctgggtggcg | aagtcgtgtt | 2040 |
| aaacgccaga | gtcagccata | tggaaacgac | aggaaacaag | attgaagccg | tgcatttaga | 2100 |
| ggacggtcgc | aggttcctga | cgcaagccgt | cgcgtcaaat | gcagatgtgg | ttcataccta | 2160 |
| tcgcgacctg | ttaagccagc | accctgccgc | ggttaagcag | tccaacaaac | tgcagactaa | 2220 |
| gcgcatgagt | ccttctctgt | ttgtgctcta | ttttggtttg | aatcaccatc | atgatcagct | 2280 |
| cgcgcatcac | acggtttgtt | tcggcccgcg | ttaccgcgag | ctgattgacg | aaatttttaa | 2340 |
| tcatgatggc | ctcgcagagg | acttctcact | ttatctgcac | gcgccctgtg | tcacggattc | 2400 |
| gtcactggcg | cctgaaggtt | gcggcagtta | ctatgtgttg | gcgccggtgc | cacatttagg | 2460 |
| caccgcgaac | ctcgactgga | cggttgaggg | gccaaaacta | cgcgaccgta | ttttgcgta | 2520 |
| ccttgagcag | cattacatgc | ctggcttacg | gagtcagctg | gtcacgcacc | ggatgtttac | 2580 |
| gccgtttgat | tttcgcgacc | agcttaatgc | ctatcatggc | tcagccttt | ctgtggagcc | 2640 |
| cgttcttacc | cagagcgcct | ggtttcggcc | gcataaccgc | gataaaacca | ttactaatct | 2700 |
| ctacctggtc | ggcgcaggca | cgcatcccgg | cgcaggcatt | cctggcgtca | tcggctcggc | 2760 |
| aaaagcgaca | gcaggtttga | tgctggagga | tctgatttga | gggcccgtgt | aggaggatta | 2820 |
| caaaatgcaa | ccgcattatg | atctgattct | cgtgggggct | ggactcgcga | atggccttat | 2880 |
| cgccctgcgt | cttcagcagc | agcaacctga | tatgcgtatt | ttgcttatcg | acgccgcacc | 2940 |
| ccaggcgggc | gggaatcata | cgtggtcatt | tcaccacgat | gatttgactg | agagccaaca | 3000 |
| tcgttggata | gctccgctgg | tggttcatca | ctggcccgac | tatcaggtac | gctttcccac | 3060 |
| acgccgtcgt | aagctgaaca | gcggctactt | ttgtattact | tctcagcgtt | tcgctgaggt | 3120 |
| tttacagcga | cagtttggcc | cgcacttgtg | gatggatacc | gcggtcgcag | aggttaatgc | 3180 |
| ggaatctgtt | cggttgaaaa | agggtcaggt | tatcggtgcc | cgcgcggtga | ttgacgggcg | 3240 |
| gggttatgcg | gcaaattcag | cactgagcgt | gggcttccag | gcgtttattg | gccaggaatg | 3300 |
| gcgattgagc | caccccgcatg | gtttatcgtc | tcccattatc | atggatgcca | cggtcgatca | 3360 |
| gcaaaatggt | tatcgcttcg | tgtacagcct | gccgctctcg | ccgaccagat | tgttaattga | 3420 |
| agacacgcac | tatattgata | atgcgacatt | agatcctgaa | tgcgcgcggc | aaaatatttg | 3480 |
| cgactatgcc | gcgcaacagg | gttggcagct | tcagacactg | ctgcgagaag | aacagggcgc | 3540 |

```
cttacccatt actctgtcgg gcaatgccga cgcattctgg cagcagcgcc ccctggcctg    3600
tagtggatta cgtgccggtc tgttccatcc taccaccggc tattcactgc cgctggcggt    3660
tgccgtggcc gaccgcctga gtgcacttga tgtctttacg tcggcctcaa ttcaccatgc    3720
cattacgcat tttgcccgcg agcgctggca gcagcagggc tttttccgca tgctgaatcg    3780
catgctgttt ttagccggac ccgccgattc acgctggcgg ttatgcagc gttttatgg     3840 tttacctgaa gatttaattg cccgttttta tgcgggaaaa ctcacgctga ccgatcggct    3900
acgtattctg agcggcaagc cgcctgttcc ggtattagca gcattgcaag ccattatgac    3960
gactcatcgt taaactagat aactagtagg aggattacaa atgttgaggg atctgctcat    4020
caccaccctg gcgctgagcc tgatcatcgg cctgcgctat ctgctggtcg gcgcggcggc    4080
ccatgggctg ctgtgggccg gggcgggccg gggacgggcg ctgaacctgc ggccgccggc    4140
gatgaagcgc atccgcgccg agatcgtcgc ctccctgatc gcctgcccca tctacgccct    4200
gccggcggcc ctggtgctgg agctgtggaa gcggggcggg acggcgatct acagcgatcc    4260
cgacgcctgg ccctgtggt ggctgccggt cagtctgatc gtctatctgc tggcgcacga    4320
cgccttctac tactgggtgc acagggccct gcatcacccg cgcgtcttcg gctgggccca    4380
tgccgaacac caccggtcgc gcgaccccag cgccttcgcc tccttcgcct tcgacccggc    4440
cgaggctgcg gccaccgcct ggttcctgcc cgccctggcc ctgatcgtgc cgatccactg    4500
gggcgtggcc ctgaccctgc tgacgctgat gtcgctgacg gccgccctga accatgcggg    4560
gcgcgaggtc tggcccgccg cctggctgga gcgggcgccg cttcgctggc tgatcaccgc    4620
cacccaccac gacgcccacc acaagcggtt caacggaaac tacggcctct atttccagtt    4680
ctgggaccgc tgggcgggga ctgaggtttc ggccgccccc tcgccaccat ccccggtcat    4740
ccctccagag cggccctcag cgcctcttcg gtgatctagt aatcgattca ctgtataaca    4800
ttaagaagga ggattacaaa atggcatggc tgacctggat cgcactgttc ctgaccgcat    4860
tcctgggtat ggaggctttc gcgtggatca tgcaccgtta tgtcatgcac ggtttcttgt    4920
ggtcgtggca tcgtagccat cacgagccgc acgaccaccc gctggaaaag aacgacctgt    4980
ttgccgttgt ctttgccgct ccggcgattg ttatggtggc ggtgggtctg cacctgtggc    5040
cttgggcctt gccggtcggt ctgggtatta ctgcgtacgg catggtttac ttcttctttc    5100
atgatggcct ggtgcatcgt cgtttcccga cgggctttag cggtcgcagc ggcttttgga    5160
cccgtcgcat ccaggcgcac cgtctgcacc atgcagtccg cacgcgtgag ggctgcgtgt    5220
cctttggctt cttgtgggtt cgcagcgcgc gtgccctgaa agcggaactg gcgcaaaaac    5280
gcggtagcag cagctctggt gcataaaagc tttatctagt tgctgatgcg gtattttctc    5340
cttacgcatc tgtgcggtat ttcacaccgc atatatggtg cactctcagt acaatctgct    5400
ctgatgccgc atagttaagc cagccccgac acccgccaac acccgctgac gcgccctgac    5460
gggcttgtct gctcccggca tccgcttaca gacaagctgt gaccgtctcc gggagctgca    5520
tgtgtcagag gttttcaccg tcatcaccga aacgcgcgag acgaaagggc ctcgtgatac    5580
gcctattttt ataggttaat gtcatgataa taatggtttc ttagacgtca ggtggcactt    5640
ttcggggaaa tgtgcgcgga acccctattt gtttattttt ctaaatacat tcaaatatgt    5700
atccgctcat gagacaataa ccctgataaa tgcttcaata atattgaaaa aggaagagta    5760
tgagtattca acatttccgt gtcgccctta ttccctttt tgcggcattt tgccttcctg    5820
tttttgctca cccagaaacg ctggtgaaag taaaagatgc tgaagatcag ttgggtgcac    5880
```

```
gagtgggtta catcgaactg atctcaaca gcggtaagat ccttgagagt tttcgccccg      5940
aagaacgttt tccaatgatg agcactttta aagttctgct atgtggcgcg gtattatccc     6000
gtattgacgc cgggcaagag caactcggtc gccgcataca ctattctcag aatgacttgg     6060
ttgagtactc accagtcaca gaaaagcatc ttacggatgg catgacagta agagaattat     6120
gcagtgctgc cataaccatg agtgataaca ctgcggccaa cttacttctg acaacgatcg     6180
gaggaccgaa ggagctaacc gcttttttgc acaacatggg gatcatgta actcgccttg      6240 atcgttggga accggagctg aatgaagcca taccaaacga cgagcgtgac accacgatgc     6300
ctgtagcaat ggcaacaacg ttgcgcaaac tattaactgg cgaactactt actctagctt     6360
cccggcaaca attaatagac tggatggagg cggataaagt tgcaggacca cttctgcgct     6420
cggcccttcc ggctggctgg tttattgctg ataaatctgg agccggtgag cgtgggtctc     6480
gcggtatcat tgcagcactg gggccagatg gtaagccctc ccgtatcgta gttatctaca     6540
cgacggggag tcaggcaact atggatgaac gaaatagaca gatcgctgag ataggtgcct     6600
cactgattaa gcattggtaa ctgtcagacc aagtttactc atatatactt tagattgatt     6660
taaaacttca ttttt aattt aaaaggatct aggtgaagat cctttttgat aatctcatga    6720
ccaaaatccc ttaacgtgag ttttcgttcc actgagcgtc agaccccgta gaaaagatca     6780
aaggatcttc ttgagatcct ttttttctgc gcgtaatctg ctgcttgcaa acaaaaaaac     6840
caccgctacc agcggtggtt tgtttgccgg atcaagagct accaactctt tttccgaagg     6900
taactggctt cagcagagcg cagataccaa atactgtcct tctagtgtag ccgtagttag     6960
gccaccactt caagaactct gtagcaccgc ctacatacct cgctctgcta atcctgttac     7020
cagtggctgc tgccagtggc gataagtcgt gtcttaccgg gttggactca agacgatagt     7080
taccggataa ggcgcagcgg tcgggctgaa cggggggttc gtgcacacag cccagcttgg     7140
agcgaacgac ctacaccgaa ctgagatacc tacagcgtga gctatgagaa agcgccacgc     7200
ttcccgaagg gagaaaggcg gacaggtatc cggtaagcgg cagggtcgga acaggagagc     7260
gcacgaggga gcttccaggg ggaaacgcct ggtatcttta tagtcctgtc gggtttcgcc     7320
acctctgact tgagcgtcga ttttgtgat gctcgtcagg gggcggagc ctatggaaaa       7380 acgccagcaa cgcggccttt ttacggttcc tggccttttg ctggccttt gctcacatgt      7440 tctttcctgc gttatcccct gattctgtgg ataaccgtat taccgccttt gagtgagctg     7500
ataccgctcg ccgcagccga acgaccgagc gcagcgagtc agtgagcgag gaagcggaag     7560
a                                                                     7561
```

<210> SEQ ID NO 21
<211> LENGTH: 8309
<212> TYPE: DNA
<213> ORGANISM: Artificial
<220> FEATURE:
<223> OTHER INFORMATION: Designed plasmid DNA,
      pUC-pBAD-CrtIN304P-CrtY-CrtG-CrtWBD-CrtZBD

<400> SEQUENCE: 21

```
gcgcccaata cgcaaaccgc ctctccccgc gcgttggccg attcattaat gcagctggca      60
cgacaggttt cccgactgga aagcgccatg gttatgacaa cttgacggct acatcattca     120 cttttttcttc acaaccggca cggaactcgc tcgggctggc cccgtgcat ttttttaaata    180 cccgcgagaa atagagttga tcgtcaaaac caacattgcg accgacgtg gcgataggca     240 tccgggtggt gctcaaaagc agcttcgcct ggctgatacg ttggtcctcg cgccagctta     300
```

```
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
cccccttgcc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgattttc accacccct gaccgcgaat ggtgagattg agaatataac    840
ctttcattcc cagcggtcgg tcgataaaaa aatcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca    1020
tcagacattg ccgtcactgc gtcttttact ggctcttctc gctaaccaaa ccgtaaccc    1080
cgcttattaa aagcattctg taacaaagcg ggaccaaagc catgacaaaa acgcgtaaca    1140
aaagtgtcta taatcacggc agaaaagtcc acattgatta tttgcacggc gtcacacttt    1200
gctatgccat agcatttta tccataagat tagcggatcc tacctgacgc ttttatcgc    1260
aactctctac tgtttctcca tacccgtttg aattctctag actcgagagg aggattacaa    1320
aatgaaacca actacggtaa ttggtgcagg cttcggtggc ctggcactgg caattcgtct    1380
acaagctgcg gggatccccg tcttactgct tgaacaacgt gataaacccg gcggtcgggc    1440
ttatgtctac gaggatcagg ggtttacctt tgatgcaggc ccgacggtta tcaccgatcc    1500
cagtgccatt gaagaactgt ttgcactggc aggaaaacag ttaaaagagt atgtcgaact    1560
gctgccggtt acgccgtttt accgcctgtg ttgggagtca gggaaggtct ttaattacga    1620
taacgatcaa acccggctcg aagcgcagat tcagcagttt aatccccgcg atgtcgaagg    1680
ttatcgtcag tttctggact attcacgcgc ggtgtttaaa gaaggctatc taaagctcgg    1740
tactgtccct ttttatcgt tcagagacat gcttcgcgcc gcacctcaac tggcgaaact    1800
gcaggcatgg agaagcgttt acagtaaggt tgccagttac atcgaagatg aacatctgcg    1860
ccaggcgttt tcttccact cgctgttggt gggcggcaat cccttcgcca cctcatccat    1920
ttatacgttg atacacgcgc tggagcgtga gtggggcgtc tggtttccgc gtggcggcac    1980
cggcgcatta gttcagggga tgataaagct gtttcaggat ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcataccta    2160
tcgcgacctg ttaagccagc accctgccgc ggttaagcag tccaacaaac tgcagactaa    2220
gcgcatgagt ccttctctgt ttgtgctcta ttttggtttg aatcaccatc atgatcagct    2280
cgcgcatcac acggtttgtt tcggcccgcg ttaccgcgag ctgattgacg aaattttttaa    2340
tcatgatggc ctcgcagagg acttctcact ttatctgcac gcgccctgtg tcacggattc    2400
gtcactggcg cctgaaggtt gcggcagtta ctatgtgttg gcgccggtgc acatttagg    2460
caccgcgaac ctcgactgga cggttgaggg gccaaaacta cgcgaccgta ttttgcgta    2520
ccttgagcag cattacatgc ctggcttacg gagtcagctg gtcacgcacc ggatgttac    2580
gccgtttgat ttcgcgacc agcttaatgc ctatcatggc tcagcctttt ctgtggagcc    2640
cgttcttacc cagagcgcct ggtttcggcc gcataaccgc gataaaacca ttactaatct    2700
```

```
ctacctggtc ggcgcaggca cgcatcccgg cgcaggcatt cctggcgtca tcggctcggc   2760
aaaagcgaca gcaggtttga tgctggagga tctgatttga gggcccgtgt aggaggatta   2820
caaaatgcaa ccgcattatg atctgattct cgtggggct ggactcgcga atggccttat    2880
cgccctgcgt cttcagcagc agcaacctga tatgcgtatt ttgcttatcg acgccgcacc   2940
ccaggcgggc gggaatcata cgtggtcatt tcaccacgat gatttgactg agagccaaca   3000
tcgttggata gctccgctgg tggttcatca ctggcccgac tatcaggtac gctttcccac   3060
acgccgtcgt aagctgaaca gcggctactt ttgtattact tctcagcgtt cgctgaggt    3120 tttacagcga cagtttggcc cgcacttgtg gatggatacc gcggtcgcag aggttaatgc   3180
ggaatctgtt cggttgaaaa agggtcaggt tatcggtgcc cgcgcggtga ttgacgggcg   3240
gggttatgcg gcaaattcag cactgagcgt gggcttccag gcgtttattg ccaggaatg    3300 gcgattgagc cacccgcatg gtttatcgtc tcccattatc atggatgcca cggtcgatca   3360
gcaaaatggt tatcgcttcg tgtacagcct gccgctctcg ccgaccagat tgttaattga   3420
agacacgcac tatattgata atgcgacatt agatcctgaa tgcgcgcggc aaaatatttg   3480
cgactatgcc gcgcaacagg gttggcagct tcagacactg ctgcgagaag aacagggcgc   3540
cttacccatt actctgtcgg gcaatgccga cgcattctgg cagcagcgcc cctggcctg    3600 tagtggatta cgtgccggtc tgttccatcc taccaccggc tattcactgc cgctggcggt   3660
tgccgtggcc gaccgcctga gtgcacttga tgtctttacg tcggcctcaa ttcaccatgc   3720
cattacgcat tttgcccgcg agcgctggca gcagcagggc ttttccgca tgctgaatcg    3780 catgctgttt ttagccggac ccgccgattc acgctggcgg gttatgcagc gtttttatgg   3840
tttacctgaa gatttaattg cccgttttta tgcgggaaaa ctcacgctga ccgatcggct   3900
acgtattctg agcggcaagc cgcctgttcc ggtattagca gcattgcaag ccattatgac   3960
gactcatcgt taaactagat aactagtagg aggattacaa atgttgaggg atctgctcat   4020
caccaccctg gcgctgagcc tgatcatcgg cctgcgctat ctgctggtcg gcgcggcggc   4080
ccatgggctg ctgtgggccg gggcggggcc gggacgggcg ctgaacctgc ggccgccggc   4140
gatgaagcgc atccgcgccg agatcgtcgc ctccctgatc gcctgcccca tctacgccct   4200
gccggcggcc ctggtgctgg agctgtggaa gcggggcggg acggcgatct acagcgatcc   4260
cgacgcctgg ccctgtggt ggctgccggt cagtctgatc gtctatctgc tggcgcacga    4320
cgccttctac tactgggtgc acagggccct gcatcacccg cgcgtcttcg gctgggccca   4380
tgccgaacac caccggtcgc gcgacccag cgccttcgcc tccttcgcct tcgacccggc    4440
cgaggctgcg gccaccgcct ggttcctgcc cgccctggcc ctgatcgtgc cgatccactg   4500
gggcgtggcc ctgaccctgc tgacgctgat gtcgctgacg gccgccctga accatgcggg   4560
gcgcgaggtc tggcccgccg cctggctgga gcgggcgccg cttcgctggc tgatcaccgc   4620
cacccaccac gacgcccacc acaagcggtt caacggaaac tacggcctct atttccagtt   4680
ctgggaccgc tgggccggga ctgaggtttc ggccgccccc tcgccaccat ccccggtcat   4740
ccctccagag cggccctcag cgcctcttcg gtgatctagt aggaggatta caaaatgacc   4800
gcagctgtcg cagaacctcg cattgtaccg cgccaaacct ggatcggcct gaccctggcg   4860
ggtatgattg tggcgggctg gggttctctg cacgtgtacg gtgtgtactt ccaccgttgg   4920
ggcaccagca gcctggttat cgtcccggct atcgtggccg ttcagacgtg ttgtcggtt    4980 ggcctgtttta ttgtcgcaca tgacgccatg cacggttccc tggccccagg ccgtccgcgc  5040
```

```
ctgaacgcag cggtgggtcg tctgacgctg ggtctgtatg caggcttccg tttcgatcgc   5100
ttgaaaacgg cgcaccacgc gcatcatgcg gctccgggta ccgcagatga cccggacttt   5160
tacgcgcctg cgccacgcgc cttcctgccg tggttttttga acttttttccg tacctatttc   5220 ggttggcgcg agatggcggt tctgaccgcg ctggtcctga tcgcgctgtt tggcttgggt   5280
gcccgtccgg cgaatctgtt gacttttttgg gccgcaccgg cgctgctgag cgcgctgcaa   5340
ctgttcacgt ttggcacctg gctgccgcac cgtcacacgg accagccgtt cgcggatgct   5400
catcatgcac gcagcagcgg ttatggtccg gttctgagcc tgctgacctg ctttcatttc   5460
ggtcgtcatc acgagcacca cctgacgccg tggcgtccgt ggtggcgttt gtggcgtggt   5520
gaaagctaaa tcgattcact gtataacatt aagaaggagg attacaaaat ggcatggctg   5580
acctggatcg cactgttcct gaccgcattc ctgggtatgg aggctttcgc gtggatcatg   5640
caccgttatg tcatgcacgg tttcttgtgg tcgtggcatc gtagccatca cgagccgcac   5700
gaccacccgc tggaaaagaa cgacctgttt gccgttgtct ttgccgctcc ggcgattgtt   5760
atggtggcgg tgggtctgca cctgtggcct tgggccttgc cggtcggtct gggtattact   5820
gcgtacggca tggtttactt cttctttcat gatggcctgg tgcatcgtcg tttcccgacg   5880
ggctttagcg gtcgcagcgg cttttggacc cgtcgcatcc aggcgcaccg tctgcaccat   5940
gcagtccgca cgcgtgaggg ctgcgtgtcc tttggcttct tgtgggttcg cagcgcgcgt   6000
gccctgaaag cggaactggc gcaaaaacgc ggtagcagca gctctggtgc ataaaagctt   6060
tatctagttg ctgatgcggt attttctcct tacgcatctg tgcggtattt cacaccgcat   6120
atatggtgca ctctcagtac aatctgctct gatgccgcat agttaagcca gccccgacac   6180
ccgccaacac ccgctgacgc gccctgacgg gcttgtctgc tcccggcatc cgcttacaga   6240
caagctgtga ccgtctccgg gagctgcatg tgtcagaggt tttcaccgtc atcaccgaaa   6300
cgcgcgagac gaaagggcct cgtgatacgc ctatttttat aggttaatgt catgataata   6360
atggtttctt agacgtcagg tggcactttt cggggaaatg tgcgcggaac ccctatttgt   6420
ttatttttct aaatacattc aaatatgtat ccgctcatga acaataaccc ctgataaatg   6480
cttcaataat attgaaaaag gaagagtatg agtattcaac atttccgtgt cgcccttatt   6540
cccttttttg cggcattttg ccttcctgtt tttgctcacc cagaaacgct ggtgaaagta   6600
aaagatgctg aagatcagtt gggtgcacga gtgggttaca tcgaactgga tctcaacagc   6660
ggtaagatcc ttgagagttt tcgccccgaa gaacgttttc caatgatgag cacttttaaa   6720
gttctgctat gtggcgcggt attatcccgt attgacgccg ggcaagagca actcggtcgc   6780
cgcatacact attctcagaa tgacttggtt gagtactcac cagtcacaga aaagcatctt   6840
acggatggca tgacagtaag agaattatgc agtgctgcca taaccatgag tgataacact   6900
gcggccaact tacttctgac aacgatcgga ggaccgaagg agctaaccgc ttttttgcac   6960
aacatggggg atcatgtaac tcgccttgat cgttgggaac cggagctgaa tgaagccata   7020
ccaaacgacg agcgtgacac cacgatgcct gtagcaatgg caacaacgtt gcgcaaacta   7080
ttaactggcg aactacttac tctagcttcc cggcaacaat taatagactg gatggaggcg   7140
gataaagttg caggaccact tctgcgctcg gcccttccgg ctggctggtt tattgctgat   7200
aaatctggag ccggtgagcg tgggtctcgc ggtatcattg cagcactggg gccagatggt   7260
aagccctccc gtatcgtagt tatctacacg acggggagtc aggcaactat ggatgaacga   7320
aatagacaga tcgctgagat aggtgcctca ctgattaagc attggtaact gtcagaccaa   7380
gtttactcat atatacttta gattgattta aaacttcatt tttaatttaa aaggatctag   7440
```

```
gtgaagatcc ttttttgataa tctcatgacc aaaatccctt aacgtgagtt ttcgttccac    7500
tgagcgtcag accccgtaga aaagatcaaa ggatcttctt gagatccttt ttttctgcgc    7560
gtaatctgct gcttgcaaac aaaaaaacca ccgctaccag cggtggtttg tttgccggat    7620
caagagctac caactctttt tccgaaggta actggcttca gcagagcgca gataccaaat    7680
actgtccttc tagtgtagcc gtagttaggc caccacttca agaactctgt agcaccgcct    7740
acatacctcg ctctgctaat cctgttacca gtggctgctg ccagtggcga taagtcgtgt    7800
cttaccgggt tggactcaag acgatagtta ccggataagg cgcagcggtc gggctgaacg    7860
gggggttcgt gcacacagcc cagcttggag cgaacgacct acaccgaact gagatacccta    7920 cagcgtgagc tatgagaaag cgccacgctt cccgaaggga gaaaggcgga caggtatccg    7980
gtaagcggca gggtcggaac aggagagcgc acgagggagc ttccagggg aaacgcctgg    8040 tatctttata gtcctgtcgg gtttcgccac ctctgacttg agcgtcgatt tttgtgatgc    8100
tcgtcagggg gcggagcct atggaaaaac gccagcaacg cggcctttttt acggttcctg    8160 gccttttgct ggccttttgc tcacatgttc tttcctgcgt tatcccctga ttctgtggat    8220
aaccgtatta ccgcctttga gtgagctgat accgctcgcc gcagccgaac gaccgagcgc    8280
agcgagtcag tgagcgagga agcggaaga                                      8309

<210> SEQ ID NO 22
<211> LENGTH: 8083
<212> TYPE: DNA
<213> ORGANISM: Artificial
<220> FEATURE:
<223> OTHER INFORMATION: Designed plasmid DNA,
      pUC-pBAD-CrtIN304P-CrtY-CrtX-CrtZBD

<400> SEQUENCE: 22
gcgcccaata cgcaaaccgc ctctccccgc gcgttggccg attcattaat gcagctggca      60
cgacaggttt cccgactgga aagcgccatg gttatgacaa cttgacggct acatcattca     120 cttttttcttc acaaccggca cggaactcgc tcgggctggc cccggtgcat ttttttaaata   180 cccgcgagaa atagagttga tcgtcaaaac caacattgcg accacggtg gcgataggca    240 tccgggtggt gctcaaaagc agcttcgcct ggctgatacg ttggtcctcg cgccagctta    300
agacgctaat ccctaactgc tggcggaaaa gatgtgacag acgcgacggc gacaagcaaa    360
catgctgtgc gacgctggcg atatcaaaat tgctgtctgc caggtgatcg ctgatgtact    420
gacaagcctc gcgtacccga ttatccatcg gtggatggag cgactcgtta atcgcttcca    480
tgcgccgcag taacaattgc tcaagcagat ttatcgccag cagctccgaa tagcgccctt    540
ccccttgccc ggcgttaatg atttgcccaa acaggtcgct gaaatgcggc tggtgcgctt    600
catccgggcg aaagaacccc gtattggcaa atattgacgg ccagttaagc cattcatgcc    660
agtaggcgcg cggacgaaag taaacccact ggtgatacca ttcgcgagcc tccggatgac    720
gaccgtagtg atgaatctct cctggcggga acagcaaaat atcacccggt cggcaaacaa    780
attctcgtcc ctgatttttc accacccct gaccgcgaat ggtgagattg agaatataac    840
ctttcattcc cagcggtcgg tcgataaaaa atcgagata accgttggcc tcaatcggcg    900
ttaaacccgc caccagatgg gcattaaacg agtatcccgg cagcagggga tcattttgcg    960
cttcagccat acttttcata ctcccgccat tcagagaaga aaccaattgt ccatattgca   1020
tcagacattg ccgtcactgc gtcttttact ggctcttctc gctaaccaaa ccggtaaccc   1080
cgcttattaa aagcattctg taacaaagcg ggaccaaagc catgacaaaa acgcgtaaca   1140
```

```
aaagtgtcta taatcacggc agaaaagtcc acattgatta tttgcacggc gtcacacttt    1200
gctatgccat agcatttta tccataagat tagcggatcc tacctgacgc tttttatcgc    1260
aactctctac tgtttctcca tacccgtttg aattctctag actcgagagg aggattacaa    1320
aatgaaacca actacggtaa ttggtgcagg cttcggtggc ctggcactgg caattcgtct    1380
acaagctgcg gggatccccg tcttactgct tgaacaacgt gataaacccg gcggtcgggc    1440
ttatgtctac gaggatcagg ggtttacctt tgatgcaggc ccgacggtta tcaccgatcc    1500
cagtgccatt gaagaactgt ttgcactggc aggaaaacag ttaaaagagt atgtcgaact    1560
gctgccggtt acgccgtttt accgcctgtg ttgggagtca gggaaggtct ttaattacga    1620
taacgatcaa acccggctcg aagcgcagat tcagcagttt aatccccgcg atgtcgaagg    1680
ttatcgtcag tttctggact attcacgcgc ggtgtttaaa gaaggctatc taaagctcgg    1740
tactgtccct ttttttatcgt tcagagacat gcttcgcgcc gcacctcaac tggcgaaact    1800
gcaggcatgg agaagcgttt acagtaaggt tgccagttac atcgaagatg aacatctgcg    1860
ccaggcgttt tcttttccact cgctgttggt gggcggcaat cccttcgcca cctcatccat    1920
ttatacgttg atacacgcgc tggagcgtga gtgggggcgtc tggtttccgc gtggcggcac    1980
cggcgcatta gttcagggga tgataaagct gttttcagga ctgggtggcg aagtcgtgtt    2040
aaacgccaga gtcagccata tggaaacgac aggaaacaag attgaagccg tgcatttaga    2100
ggacggtcgc aggttcctga cgcaagccgt cgcgtcaaat gcagatgtgg ttcataccta    2160
tcgcgacctg ttaagccagc accctgccgc ggttaagcag tccaacaaac tgcagactaa    2220
gcgcatgagt ccttctctgt ttgtgctcta ttttggtttg aatcaccatc atgatcagct    2280
cgcgcatcac acggtttgtt tcggcccgcg ttaccgcgag ctgattgacg aaattttaa    2340 tcatgatggc ctcgcagagg acttctcact ttatctgcac gcgccctgtg tcacggattc    2400
gtcactggcg cctgaaggtt gcggcagtta ctatgtgttg gcgccggtgc cacatttagg    2460
caccgcgaac ctcgactgga cggttgaggg gccaaaacta cgcgaccgta ttttgcgta    2520 ccttgagcag cattacatgc ctggcttacg gagtcagctg gtcacgcacc ggatgtttac    2580
gccgtttgat tttcgcgacc agcttaatgc ctatcatggc tcagccttt ctgtggagcc    2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcaa ccgcattatg atctgattct cgtgggggct ggactcgcga atggccttat    2880
cgccctgcgt cttcagcagc agcaacctga tatgcgtatt ttgcttatcg acgccgcacc    2940
ccaggcgggc gggaatcata cgtggtcatt tcaccacgat gatttgactg agagccaaca    3000
tcgttggata gctccgctgg tggttcatca ctggcccgac tatcaggtac gctttcccac    3060
acgccgtcgt aagctgaaca gcggctactt ttgtattact tctcagcgtt cgctgaggt    3120 tttacagcga cagtttggcc cgcacttgtg gatggatacc gcggtcgcag aggttaatgc    3180
ggaatctgtt cggttgaaaa agggtcaggt tatcggtgcc cgcgcggtga ttgacgggcg    3240
gggttatgcg gcaaattcag cactgagcgt gggcttccag gcgttattg gccaggaatg    3300 gcgattgagc cacccgcatg gtttatcgtc tcccattatc atggatgcca cggtcgatca    3360
gcaaaatggt tatcgcttcg tgtacagcct gccgctctcg ccaccagat tgttaattga    3420 agacacgcac tatattgata atgcgacatt agatcctgaa tgcgcgcggc aaaatatttg    3480
```

| | |
|---|---|
| cgactatgcc gcgcaacagg gttggcagct tcagacactg ctgcgagaag aacagggcgc | 3540 |
| cttacccatt actctgtcgg gcaatgccga cgcattctgg cagcagcgcc ccctggcctg | 3600 |
| tagtggatta cgtgccggtc tgttccatcc taccaccggc tattcactgc cgctggcggt | 3660 |
| tgccgtggcc gaccgcctga gtgcacttga tgtctttacg tcggcctcaa ttcaccatgc | 3720 |
| cattacgcat tttgcccgcg agcgctggca gcagcagggc ttttccgca tgctgaatcg | 3780 |
| catgctgttt ttagccggac ccgccgattc acgctggcgg gttatgcagc gtttttatgg | 3840 |
| tttacctgaa gatttaattg cccgtttta tgcgggaaaa ctcacgctga ccgatcggct | 3900 |
| acgtattctg agcggcaagc cgcctgttcc ggtattagca gcattgcaag ccattatgac | 3960 |
| gactcatcgt taaactagat aactagtagg aggattacaa atgagccatt cgcggcgat | 4020 |
| cgcaccgcct ttttacagcc atgttcgcgc attacagaat ctcgctcagg aactggtcgc | 4080 |
| gcgcggtcat cgggtgacct ttattcagca atacgatatt aaacacttga tcgatagcga | 4140 |
| aaccattgga tttcattccg tcgggacaga cagccatccc cccggcgcgt taacgcgcgt | 4200 |
| gctacacctg gcggctcatc ctctgggcc gtcaatgctg aagctcatca atgaaatggc | 4260 |
| gcgcaccacc gatatgctgt gccgcgaact cccccaggca tttaacgatc tggccgtcga | 4320 |
| tggcgtcatt gttgatcaaa tggaaccggc aggcgcgctc gttgctgaag cactgggact | 4380 |
| gccgtttatc tctgtcgcct gcgcgctgcc tctcaatcgt gaaccggata tgcccctggc | 4440 |
| ggttatgcct ttcgaatacg ggaccagcga cgcggctcgc gaacgttatg ccgccagtga | 4500 |
| aaaaatttat gactggctaa tgcgtcgtca tgaccgtgtc attgccgaac acagccacag | 4560 |
| aatgggctta gccccccggc aaaagcttca ccagtgtttt tcgccactgg cgcaaatcag | 4620 |
| ccagcttgtt cctgaactgg attttccccg caaagcgtta ccggcttgtt ttcatgccgt | 4680 |
| cgggcctctg cgcgaaacgc acgcaccgtc aacgtcttca tcccgttatt ttacatcctc | 4740 |
| agaaaaaccc cggatttcg cctcgctggg cacgcttcag ggacaccgtt atgggctgtt | 4800 |
| taaaacgata gtgaaagcct gtgaagaaat tgacggtcag ctcctgttag cccactgtgg | 4860 |
| tcgtcttacg gactctcagt gtgaagagct ggcgcgaagc cgtcatacac aggtggtgga | 4920 |
| ttttgccgat cagtcagccg cgctgtctca ggcgcagctg gcgatcaccc acggcggcat | 4980 |
| gaatacggta ctggacgcga ttaattaccg gacgccccttt tagcgcttc cgctggcctt | 5040 |
| tgatcagccc ggcgtcgcgt cacgcatcgt ttatcacggc atcggcaagc gtgcttcccg | 5100 |
| ctttaccacc agccatgctt tggctcgtca gatgcgttca ttgctgacca acgtcgactt | 5160 |
| tcagcagcgc atggcgaaaa tccagacagc ccttcgtttg gcaggggca ccatggccgc | 5220 |
| tgccgatatc attgagcagg ttatgtgcac cggtcagcct gtcttaagtg ggagcggcta | 5280 |
| tgcaaccgca ttatgatcta gtaatcgatt cactgtataa cattaagaag gaggattaca | 5340 |
| aaatggcatg gctgacctgg atcgcactgt tcctgaccgc attcctgggt atggaggctt | 5400 |
| tcgcgtggat catgcaccgt tatgtcatgc acggtttctt gtggtcgtgg catcgtagcc | 5460 |
| atcacgagcc gcacgaccac ccgctggaaa agaacgacct gtttgccgtt gtctttgccg | 5520 |
| ctccggcgat tgttatggtg gcggtgggtc tgcacctgtg gccttgggcc ttgccggtcg | 5580 |
| gtctgggtat tactgcgtac ggcatggttt acttcttctt tcatgatggc ctggtgcatc | 5640 |
| gtcgtttccc gacgggcttt agcggtcgca gcggcttttg gacccgtcgc atccaggcgc | 5700 |
| accgtctgca ccatgcagtc cgcacgcgtg agggctgcgt gtcctttggc ttcttgtggg | 5760 |
| ttcgcagcgc gcgtgccctg aaagcggaac tggcgcaaaa acgcgtagc agcagctctg | 5820 |
| gtgcataaaa gctttatccta gttgctgatg cggtattttc tccttacgca tctgtgcggt | 5880 |

| | | | | |
|---|---|---|---|---|
| atttcacacc | gcatatatgg | tgcactctca | gtacaatctg | ctctgatgcc gcatagttaa | 5940 |
| gccagcsccg | acacccgcca | acacccgctg | acgcgccctg | acgggcttgt ctgctcccgg | 6000 |
| catccgctta | cagacaagct | gtgaccgtct | ccgggagctg | catgtgtcag aggttttcac | 6060 |
| cgtcatcacc | gaaacgcgcg | agacgaaagg | gcctcgtgat | acgcctattt ttataggtta | 6120 |
| atgtcatgat | aataatggtt | tcttagacgt | caggtggcac | ttttcgggga aatgtgcgcg | 6180 |
| gaacccctat | ttgtttattt | ttctaaatac | attcaaatat | gtatccgctc atgagacaat | 6240 |
| aaccctgata | aatgcttcaa | taatattgaa | aaggaagag | tatgagtatt caacatttcc | 6300 |
| gtgtcgccct | tattcccttt | tttgcggcat | tttgccttcc | tgtttttgct cacccagaaa | 6360 |
| cgctggtgaa | agtaaaagat | gctgaagatc | agttgggtgc | acgagtgggt tacatcgaac | 6420 |
| tggatctcaa | cagcggtaag | atccttgaga | gttttcgccc | cgaagaacgt tttccaatga | 6480 |
| tgagcacttt | taaagttctg | ctatgtggcg | cggtattatc | ccgtattgac gccgggcaag | 6540 |
| agcaactcgg | tcgccgcata | cactattctc | agaatgactt | ggttgagtac tcaccagtca | 6600 |
| cagaaaagca | tcttacggat | ggcatgacag | taagagaatt | atgcagtgct gccataacca | 6660 |
| tgagtgataa | cactgcggcc | aacttacttc | tgacaacgat | cggaggaccg aaggagctaa | 6720 |
| ccgcttttt | gcacaacatg | ggggatcatg | taactcgcct | tgatcgttgg gaaccggagc | 6780 |
| tgaatgaagc | cataccaaac | gacgagcgtg | acaccacgat | gcctgtagca atggcaacaa | 6840 |
| cgttgcgcaa | actattaact | ggcgaactac | ttactctagc | ttcccggcaa caattaatag | 6900 |
| actggatgga | ggcggataaa | gttgcaggac | cacttctgcg | ctcggccctt ccggctggct | 6960 |
| ggtttattgc | tgataaatct | ggagccggtg | agcgtgggtc | tcgcggtatc attgcagcac | 7020 |
| tggggccaga | tggtaagccc | tcccgtatcg | tagttatcta | cacgacgggg agtcaggcaa | 7080 |
| ctatggatga | acgaaataga | cagatcgctg | agataggtgc | ctcactgatt aagcattggt | 7140 |
| aactgtcaga | ccaagtttac | tcatatatac | tttagattga | tttaaaactt catttttaat | 7200 |
| ttaaaaggat | ctaggtgaag | atcctttttg | ataatctcat | gaccaaaatc ccttaacgtg | 7260 |
| agttttcgtt | ccactgagcg | tcagaccccg | tagaaaagat | caaaggatct tcttgagatc | 7320 |
| ctttttttct | gcgcgtaatc | tgctgcttgc | aaacaaaaaa | accaccgcta ccagcggtgg | 7380 |
| tttgtttgcc | ggatcaagag | ctaccaactc | tttttccgaa | ggtaactggc ttcagcagag | 7440 |
| cgcagatacc | aaatactgtc | cttctagtgt | agccgtagtt | aggccaccac ttcaagaact | 7500 |
| ctgtagcacc | gcctacatac | ctcgctctgc | taatcctgtt | accagtggct gctgccagtg | 7560 |
| gcgataagtc | gtgtcttacc | gggttggact | caagacgata | gttaccggat aaggcgcagc | 7620 |
| ggtcgggctg | aacggggggt | tcgtgcacac | agcccagctt | ggagcgaacg acctacaccg | 7680 |
| aactgagata | cctacagcgt | gagctatgag | aaagcgccac | gcttcccgaa gggagaaagg | 7740 |
| cggacaggta | tccggtaagc | ggcagggtcg | gaacaggaga | gcgcacgagg gagcttccag | 7800 |
| ggggaaacgc | ctggtatctt | tatagtcctg | tcgggtttcg | ccacctctga cttgagcgtc | 7860 |
| gatttttgtg | atgctcgtca | ggggggcgga | gcctatggaa | aaacgccagc aacgcggcct | 7920 |
| ttttacggtt | cctggccttt | tgctggcctt | ttgctcacat | gttctttcct gcgttatccc | 7980 |
| ctgattctgt | ggataaccgt | attaccgcct | ttgagtgagc | tgataccgct cgccgcagcc | 8040 |
| gaacgaccga | gcgcagcgag | tcagtgagcg | aggaagcgga | aga | 8083 |

<210> SEQ ID NO 23
<211> LENGTH: 8831
<212> TYPE: DNA

<213> ORGANISM: Artificial
<220> FEATURE:
<223> OTHER INFORMATION: Designed plasmid DNA,
      pUC-pBAD-CrtIN304P-CrtY-CrtX-CrtWBD-CrtZBD

<400> SEQUENCE: 23

```
gcgcccaata cgcaaaccgc ctctccccgc gcgttggccg attcattaat gcagctggca    60
cgacaggttt cccgactgga aagcgccatg gttatgacaa cttgacggct acatcattca   120
cttttcttc acaaccggca cggaactcgc tcgggctggc cccggtgcat tttttaaata   180
cccgcgagaa atagagttga tcgtcaaaac caacattgcg accgacggtg gcgataggca   240
tccgggtggt gctcaaaagc agcttcgcct ggctgatacg ttggtcctcg cgccagctta   300
agacgctaat ccctaactgc tggcggaaaa gatgtgacag acgcgacggc gacaagcaaa   360
catgctgtgc cacgctggcg atatcaaaat tgctgtctgc caggtgatcg ctgatgtact   420
gacaagcctc gcgtacccga ttatccatcg gtggatggag cgactcgtta atcgcttcca   480
tgcgccgcag taacaattgc tcaagcagat ttatcgccag cagctccgaa tagcgccctt   540
ccccttgccc ggcgttaatg atttgcccaa acaggtcgct gaaatgcggc tggtgcgctt   600
catccgggcg aaagaacccc gtattggcaa atattgacgg ccagttaagc cattcatgcc   660
agtaggcgcg cggacgaaag taaacccact ggtgatacca ttcgcgagcc tccggatgac   720
gaccgtagtg atgaatctct cctggcggga acagcaaaat atcacccggt cggcaaacaa   780
attctcgtcc ctgattttc accaccccct gaccgcgaat ggtgagattg agaatataac   840
ctttcattcc cagcggtcgg tcgataaaaa aatcgagata accgttggcc tcaatcggcg   900
ttaaacccgc caccagatgg gcattaaacg agtatcccgg cagcagggga tcattttgcg   960
cttcagccat acttttcata ctcccgccat tcagagaaga aaccaattgt ccatattgca  1020
tcagacattg ccgtcactgc gtcttttact ggctcttctc gctaaccaaa ccggtaaccc  1080
cgcttattaa aagcattctg taacaaagcg ggaccaaagc catgacaaaa acgcgtaaca  1140
aaagtgtcta taatcacggc agaaaagtcc acattgatta tttgcacggc gtcacacttt  1200
gctatgccat agcatttta tccataagat tagcggatcc tacctgacgc ttttatcgc  1260
aactctctac tgtttctcca tacccgtttg aattctctag actcgagagg aggattacaa  1320
aatgaaacca actacggtaa ttggtgcagg cttcggtggc ctggcactgg caattcgtct  1380
acaagctgcg gggatccccg tcttactgct tgaacaacgt gataaacccg gcggtcgggc  1440
ttatgtctac gaggatcagg ggtttacctt tgatgcaggc ccgacggtta tcaccgatcc  1500
cagtgccatt gaagaactgt ttgcactggc aggaaaacag ttaaagagt atgtcgaact  1560
gctgccggtt acgccgtttt accgcctgtg ttgggagtca gggaaggtct taattacga  1620
taacgatcaa cccggctcg aagcgcagat tcagcagttt aatccccgcg atgtcgaagg  1680
ttatcgtcag tttctggact attcacgcgc ggtgtttaaa gaaggctatc taaagctcgg  1740
tactgtccct ttttatcgt tcagagacat gcttcgcgcc gcacctcaac tggcgaaact  1800
gcaggcatgg agaagcgttt acagtaaggt tgccagttac atcgaagatg aacatctgcg  1860
ccaggcgttt tctttccact cgctgttggt gggcggcaat cccttcgcca cctcatccat  1920
ttatacgttg atacacgcgc tggagcgtga gtggggcgtc tggtttccgc gtggcggcac  1980
cggcgcatta gttcagggga tgataaagct gtttcaggat ctgggtggcg aagtcgtgtt  2040
aaacgccaga gtcagccata tggaaacgac aggaaacaag attgaagccg tgcatttaga  2100
ggacggtcgc aggttcctga cgcaagccgt cgcgtcaaat gcagatgtgg ttcataccta  2160
```

```
tcgcgacctg ttaagccagc accctgccgc ggttaagcag tccaacaaac tgcagactaa    2220
gcgcatgagt ccttctctgt ttgtgctcta ttttggtttg aatcaccatc atgatcagct    2280
cgcgcatcac acggtttgtt tcggcccgcg ttaccgcgag ctgattgacg aaattttaa     2340 tcatgatggc ctcgcagagg acttctcact ttatctgcac gcgccctgtg tcacggattc    2400
gtcactggcg cctgaaggtt gcggcagtta ctatgtgttg gcgccggtgc cacatttagg    2460
caccgcgaac ctcgactgga cggttgaggg gccaaaacta cgcgaccgta tttttgcgta    2520
ccttgagcag cattacatgc ctggcttacg gagtcagctg gtcacgcacc ggatgtttac    2580
gccgtttgat tttcgcgacc agcttaatgc ctatcatggc tcagccttt ctgtggagcc     2640 cgttcttacc cagagcgcct ggtttcggcc gcataaccgc gataaaacca ttactaatct    2700
ctacctggtc ggcgcaggca cgcatcccgg cgcaggcatt cctggcgtca tcggctcggc    2760
aaaagcgaca gcaggtttga tgctggagga tctgatttga gggcccgtgt aggaggatta    2820
caaaatgcaa ccgcattatg atctgattct cgtgggggct ggactcgcga atggccttat    2880
cgccctgcgt cttcagcagc agcaacctga tatgcgtatt ttgcttatcg acgccgcacc    2940
ccaggcgggc gggaatcata cgtggtcatt tcaccacgat gatttgactg agagccaaca    3000
tcgttggata gctccgctgg tggttcatca ctggcccgac tatcaggtac gctttcccac    3060
acgccgtcgt aagctgaaca gcggctactt ttgtattact tctcagcgtt cgctgaggt     3120 tttacagcga cagtttggcc cgcacttgtg gatggatacc gcggtcgcag aggttaatgc    3180
ggaatctgtt cggttgaaaa agggtcaggt tatcggtgcc cgcgcggtga ttgacgggcg    3240
gggttatgcg gcaaattcag cactgagcgt gggcttccag gcgtttattg ccaggaatg    3300 gcgattgagc cacccgcatg gtttatcgtc tcccattatc atggatgcca cggtcgatca    3360
gcaaaatggt tatcgcttcg tgtacagcct gccgctctcg ccgaccagat tgttaattga    3420
agacacgcac tatattgata atgcgacatt agatcctgaa tgcgcgcggc aaaatatttg    3480
cgactatgcc gcgcaacagg gttggcagct tcagacactg ctgcgagaag aacagggcgc    3540
cttacccatt actctgtcgg gcaatgccga cgcattctgg cagcagcgcc cctggcctg    3600 tagtggatta cgtgccggtc tgttccatcc taccaccggc tattcactgc cgctggcggt    3660
tgccgtggcc gaccgcctga gtgcacttga tgtctttacg tcggcctcaa ttcaccatgc    3720
cattacgcat tttgcccgcg agcgctggca gcagcagggc ttttccgca tgctgaatcg     3780 catgctgttt ttagccggac ccgccgattc acgctggcgg gttatgcagc gttttttatgg   3840 tttacctgaa gatttaattg cccgttttta tgcgggaaaa ctcacgctga ccgatcggct    3900
acgtattctg agcggcaagc cgcctgttcc ggtattagca gcattgcaag ccattatgac    3960
gactcatcgt taaactagat aactagtagg aggattacaa atgagccatt tcgcggcgat    4020
cgcaccgcct ttttacagcc atgttcgcgc attacagaat ctcgctcagg aactggtcgc    4080
gcgcggtcat cgggtgacct ttattcagca atacgatatt aaacacttga tcgatagcga    4140
aaccattgga tttcattccg tcgggacaga cagccatccc ccggcgcgt taacgcgcgt     4200 gctacacctg gcggctcatc ctctggggcc gtcaatgctg aagctcatca atgaaatggc    4260
gcgcaccacc gatatgctgt gccgcgaact cccccaggca tttaacgatc tggccgtcga    4320
tggcgtcatt gttgatcaaa tggaaccggc aggcgcgctc gttgctgaag cactgggact    4380
gccgtttatc tctgtcgcct gcgcgctgcc tctcaatcgt gaaccggata tgcccctggc    4440
ggttatgcct ttcgaatacg ggaccagcga cgcggctcgc gaacgttatg ccgccagtga    4500
aaaaatttat gactggctaa tgcgtcgtca tgaccgtgtc attgccgaac acagccacag    4560
```

```
aatgggctta gcccccggc aaaagcttca ccagtgtttt tcgccactgg cgcaaatcag    4620
ccagcttgtt cctgaactgg attttccccg caaagcgtta ccggcttgtt ttcatgccgt    4680
cgggcctctg cgcgaaacgc acgcaccgtc aacgtcttca tcccgttatt ttacatcctc    4740
agaaaaaccc cggattttcg cctcgctggg cacgcttcag ggacaccgtt atgggctgtt    4800
taaaacgata gtgaaagcct gtgaagaaat tgacggtcag ctcctgttag cccactgtgg    4860
tcgtcttacg gactctcagt gtgaagagct ggcgcgaagc cgtcatacac aggtggtgga    4920
ttttgccgat cagtcagccg cgctgtctca ggcgcagctg gcgatacccc acggcggcat    4980
gaatacggta ctggacgcga ttaattaccg gacgcccctt ttagcgcttc cgctggcctt    5040
tgatcagccc ggcgtcgcgt cacgcatcgt ttatcacggc atcggcaagc gtgcttccg    5100 ctttaccacc agccatgctt tggctcgtca gatgcgttca ttgctgacca acgtcgactt    5160
tcagcagcgc atggcgaaaa tccagacagc ccttcgtttg cagggggca ccatggccgc    5220 tgccgatatc attgagcagg ttatgtgcac cggtcagcct gtcttaagtg ggagcggcta    5280
tgcaaccgca ttatgatcta gtaggaggat tacaaaatga ccgcagctgt cgcagaacct    5340
cgcattgtac cgcgccaaac ctggatcggc ctgaccctgg cgggtatgat tgtggcgggc    5400
tggggttctc tgcacgtgta cggtgtgtac ttccaccgtt ggggcaccag cagcctggtt    5460
atcgtcccgg ctatcgtggc cgttcagacg tggttgtcgg ttggcctgtt tattgtcgca    5520
catgacgcca tgcacggttc cctggcccca ggccgtccgc gcctgaacgc agcggtgggt    5580
cgtctgacgc tgggtctgta tgcaggcttc cgtttcgatc gcttgaaaac ggcgcaccac    5640
gcgcatcatg cggctccggg taccgcagat gacccggact tttacgcgcc tgcgccacgc    5700
gccttcctgc cgtggttttt gaacttttc cgtacctatt tcggttggcg cgagatggcg    5760
gttctgaccg cgctggtcct gatcgcgctg tttggcttgg gtgcccgtcc ggcgaatctg    5820 ttgactttt gggccgcacc ggcgctgctg agcgcgctgc aactgttcac gtttggcacc    5880
tggctgccgc accgtcacac ggaccagccg ttcgcggatg ctcatcatgc acgcagcagc    5940
ggttatggtc cggttctgag cctgctgacc tgctttcatt tcggtcgtca tcacgagcac    6000
cacctgacgc cgtggcgtcc gtggtggcgt ttgtggcgtg gtgaaagcta aatcgattca    6060
ctgtataaca ttaagaagga ggattacaaa atggcatggc tgacctggat cgcactgttc    6120
ctgaccgcat tcctgggtat ggaggctttc gcgtggatca tgcaccgtta tgtcatgcac    6180
ggtttcttgt ggtcgtggca tcgtagccat cacgagccgc acgaccaccc gctggaaaag    6240
aacgacctgt tgccgttgt ctttgccgct ccggcgattg ttatggtggc ggtgggtctg    6300
cacctgtggc cttgggcctt gccggtcggt ctgggtatta ctgcgtacgg catggtttac    6360
ttcttctttc atgatggcct ggtgcatcgt cgtttcccga cgggctttag cggtcgcagc    6420
ggcttttgga cccgtcgcat ccaggcgcac cgtctgcacc atgcagtccg cacgcgtgag    6480
ggctgcgtgt cctttggctt cttgtgggtt cgcagcgcgc gtgccctgaa agcggaactg    6540
gcgcaaaaac gcggtagcag cagctctggt gcataaaagc tttatctagt tgctgatgcg    6600 gtatttctc cttacgcatc tgtgcggtat ttcacaccgc atatatggtg cactctcagt    6660
acaatctgct ctgatgccgc atagttaagc cagccccgac acccgccaac acccgctgac    6720
gcgccctgac gggcttgtct gctcccggca tccgcttaca gacaagctgt gaccgtctcc    6780
gggagctgca tgtgtcagag gttttcaccg tcatcaccga aacgcgcgag acgaaagggc    6840
ctcgtgatac gcctattttt ataggttaat gtcatgataa taatggtttc ttagacgtca    6900
```

```
ggtggcactt ttcggggaaa tgtgcgcgga acccctattt gtttattttt ctaaatacat      6960
tcaaatatgt atccgctcat gagacaataa ccctgataaa tgcttcaata atattgaaaa      7020
aggaagagta tgagtattca acatttccgt gtcgccctta ttccctttttt gcggcattt      7080 tgccttcctg ttttttgctca cccagaaacg ctggtgaaag taaaagatgc tgaagatcag     7140
ttgggtgcac gagtgggtta catcgaactg gatctcaaca gcggtaagat ccttgagagt      7200
tttcgccccg aagaacgttt tccaatgatg agcactttta aagttctgct atgtggcgcg     7260
gtattatccc gtattgacgc cgggcaagag caactcggtc gccgcataca ctattctcag     7320
aatgacttgg ttgagtactc accagtcaca gaaaagcatc ttacgatgg catgacagta       7380 agagaattat gcagtgctgc cataaccatg agtgataaca ctgcggccaa cttacttctg      7440
acaacgatcg gaggaccgaa ggagctaacc gcttttttgc acaacatggg ggatcatgta      7500
actcgccttg atcgttggga accggagctg aatgaagcca taccaaacga cgagcgtgac      7560
accacgatgc ctgtagcaat ggcaacaacg ttgcgcaaac tattaactgg cgaactactt      7620
actctagctt cccggcaaca attaatagac tggatggagg cggataaagt tgcaggacca      7680
cttctgcgct cggcccttcc ggctggctgg tttattgctg ataaatctgg agccggtgag      7740
cgtgggtctc gcggtatcat tgcagcactg gggccagatg gtaagccctc ccgtatcgta      7800
gttatctaca cgacggggag tcaggcaact atggatgaac gaaatagaca gatcgctgag      7860
ataggtgcct cactgattaa gcattggtaa ctgtcagacc aagtttactc atatatactt      7920
tagattgatt taaaacttca ttttttaattt aaaaggatct aggtgaagat cctttttgat     7980
aatctcatga ccaaaatccc ttaacgtgag ttttcgttcc actgagcgtc agacccgta      8040 gaaaagatca aggatcttc ttgagatcct ttttttctgc gcgtaatctg ctgcttgcaa       8100
acaaaaaaac caccgctacc agcggtggtt tgtttgccgg atcaagagct accaactctt      8160
tttccgaagg taactggctt cagcagagcg cagataccaa atactgtcct tctagtgtag      8220
ccgtagttag gccaccactt caagaactct gtagcaccgc ctacatacct cgctctgcta      8280
atcctgttac cagtggctgc tgccagtggc gataagtcgt gtcttaccgg gttggactca      8340
agacgatagt taccggataa ggcgcagcgg tcgggctgaa cggggggttc gtgcacacag      8400
cccagcttgg agcgaacgac ctacaccgaa ctgagatacc tacagcgtga gctatgagaa      8460
agcgccacgc ttcccgaagg gagaaaggcg gacaggtatc cggtaagcgg cagggtcgga     8520
acaggagagc gcacgaggga gcttccaggg ggaaacgcct ggtatcttta tagtcctgtc      8580
gggtttcgcc acctctgact tgagcgtcga ttttttgtgat gctcgtcagg ggggcggagc     8640
ctatggaaaa acgccagcaa cgcggccttt ttacggttcc tggccttttg ctggcctttt     8700
gctcacatgt tctttcctgc gttatcccct gattctgtgg ataaccgtat taccgccttt     8760
gagtgagctg ataccgctcg ccgcagccga acgaccgagc gcagcgagtc agtgagcgag     8820
gaagcggaag a                                                           8831
```

<210> SEQ ID NO 24
<211> LENGTH: 6689
<212> TYPE: DNA
<213> ORGANISM: Artificial
<220> FEATURE:
<223> OTHER INFORMATION: Designed plasmid DNA, pAC-hexPS

<400> SEQUENCE: 24

```
gaattccgga tgagcattca tcaggcgggc aagaatgtga ataaaggccg gataaaactt        60
gtgcttattt ttctttacgg tctttaaaaa ggccgtaata tccagctgaa cggtctggtt      120
```

```
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgccccctg acaagcatca cgaaatctga cgctcaaatc     900
agtggtggcg aaacccgaca ggactataaa gataccaggc gtttccctg gcggctccct     960 cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga acccccgtt cagtccgacc gctgcgcctt atccggtaac tatcgtcttg     1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320
gaaaaaccgc cctgcaaggc ggttttttcg ttttcagagc aagagattac gcgcagacca    1380
aaacgatctc aagaagatca tcttattaat cagataaaat atttcaagat ttcagtgcaa    1440
tttatctctt caaatgtagc acctgaagtc agccccatac gatataagtt gtaattctca    1500
tgtttgacag cttatcatcg ataagcttta atgcggtagt ttatcacagt taaattgcta    1560
acgcagtcag gcaccgtgta tgaaatctaa caatgcgctc atcgtcatcc tcggcaccgt    1620
caccctggat gctgtaggca taggcttggt tatgccggta ctgccgggcc tcttgcggga    1680
tatcgtccat tccgacagca tcgccagtca ctatggcgtg ctgctagcgc tatatgcgtt    1740
gatgcaattt ctatgcgcac ccgttctcgg agcactgtcc gaccgctttg ccgccgccc     1800 agtcctgctc gcttcgctac ttggagccac tatcgactac gcgatcatgg cgaccacacc    1860
cgtcctgtgg atcccgtgga ggtttcccga ctggaaagcg ggcagtgagc gcaacgcaat    1920
taatgtgagt tagctcactc attaggcacc ccaggcttta cactttatgc ttccggctcg    1980
tatgttgtgt ggaattgtga gcggataaca atttcacaca ggaaacacat atggaattca    2040
ggaggtagat caatgcgtta tttacataaa attgaactag aattaaaccg acttacaagt    2100
cgatatccat tttcaaaaa aattgcattt gatgctgaaa tcataaagct cgttgatgac     2160
ctaaatgtcg atgaaaatgt aaaatgtgcg attgttgcca ttgacacgag tatgcgtatg    2220
caggatttta tcaatgaaga taataaagac agttttgtac tatcaacgga tgttttgagt    2280
gctttatttt ataagtattt atcacagcca ttttatcagc atgattttt agtactgacg     2340 gattgtgtaa gtcgtatcaa tgaattaaaa tcaataagag caacgattac agacgaaatt    2400
gctttgcata atattaataa acaaattcat tatatgttca tacaacctta tatgaacaat    2460
```

```
gagaaagtgg tgtcttatga gtaaacagtt aaatggacag gaaaaaagtg agcttgtaca    2520
taatgtattc cagaatgtat cgacaaagta tgaccgcctc aacgatatca taagttttaa    2580
tcagcataaa tcctggcgta aatatacgat gaaacagatg aatgttaaaa aagggtcgaa    2640
agcacttgat gtatgctgcg gtacaggcga ctggacaatt cagatggcac aggctgtcgg    2700
taaaaatggt catgttattg gtcttgattt cagtgagaat atgttaagtg ttgcacaagg    2760
aaaaacgaat catatacaaa atattgaatt aattcatggt aatgcgatgg aattaccatt    2820
tgaagataat atatttgatt atacaacgat tggttttggt ttacgtaact taccggatta    2880
taaaaaagga ttagaagaaa tgtatcgtgt attaaaacct ggcggcatga ttgttgtttt    2940
agaaacgagc catccaacaa tgccagtatt taaacaaggt tacaaattat atttcaaata    3000
cgttatgccc ctgtttggga aagtatttgc taagtctatg aaggaatata gctggttaca    3060
gcaaagtgct tttgaatttc ctgataagta cacgttagca cttttaatgg ctgaaactgg    3120
atttacacac attaaattta aaggttttac tggtggcgtg agtgcgatgc atcttgcata    3180
caagccgaaa gaaaaataga atggatgatt gctttgagtt ataaagcgtt tttaaaccca    3240
tatatcattg aagttgaaaa aaggttatat gagtgtattc agagtgattc tgaaacgata    3300
aacaaggcgg cacaccatat tttaagttca ggaggaaagc gcgtacgtcc gatgtttgta    3360
ttattaagtg gttttctgaa tgatacacaa aaggatgact tgattcgtac agcagtatct    3420
ctggagctcg ttcatatggc aagtctcgtt catgatgatt acatcgataa tagtgatatg    3480
cgtcgtggta atacttcggt tcatatagct tttgataaag acacagcaat tcgcacagga    3540 catttttat tagcacgtgc gttacaaaat attgcaacta tcaataattc gaaattccat    3600
caaattttta gtaaaacgat acttgaagtt tgttttggtg aatttgacca gatggcagat    3660
cgatttaatt atcctgtatc ctttactgca tatttaagac gtattaatcg taaaacagcg    3720
atactgatag aagcaagctg tcatttaggg gctctcagct cacagcttga tgaacaatct    3780
acatatcata taaaacaatt tgggcattgt attggaatga gttatcaaat tattgatgat    3840
attctcgatt acacgagtga cgaagcaaca ctcggtaaac ctgtcggtag cgatataaga    3900
aacggtcata ttacgtatcc gcttatggcc gctatcgcta atttgaaaga gcaagatgac    3960
gataaacttg aagcagttgt taaacattta acatcaacat cagatgatga agtgtatcaa    4020
tatattgttt cgcaagttaa acaatatgga attgaacctg cagaattgct gagcagaaaa    4080
tatggtgata aagcgaaata tcacttgagt caattacagg atagtaatat taaagattat    4140
ttagaagaaa tccacgaaaa aatgttaaaa cgtgtttatt aatctagact cgaggggccc    4200
ggcgcctgat gcggtatttt ctccttacgc atctgtgcgg tatttcacgt gcgctcgagg    4260
ggcccggcgc ctgatgcggt attttctcct tacgcatctg tgcggtattt cacggatcct    4320
ctacgccgga cgcatcgtgg ccggcatcac cggcgccaca ggtgcggttg ctggcgccta    4380
tatcgccgac atcaccgatg gggaagatcg ggctcgccac ttcgggctca tgagcgcttg    4440
tttcggcgtg ggtatggtgg caggccccgt ggccggggga ctgttgggcg ccatctcctt    4500
gcatgcacca ttccttgcgg cggcggtgct caacggcctc aacctactac tgggctgctt    4560
cctaatgcag gagtcgcata agggagagcg tcgaccgatg cccttgagag ccttcaaccc    4620
agtcagctcc ttccggtggg cgcggggcat gactatcgtc gccgcactta tgactgtctt    4680
ctttatcatg caactcgtag gacaggtgcc ggcagcgctc tgggtcattt tcggcgagga    4740
ccgctttcgc tggagcgcga cgatgatcgg cctgtcgctt gcggtattcg gaatcttgca    4800
cgccctcgct caagccttcg tcactggtcc cgccaccaaa cgtttcggcg agaagcaggc    4860
```

```
cattatcgcc ggcatggcgg ccgacgcgct gggctacgtc ttgctggcgt tcgcgacgcg    4920
aggctggatg gccttcccca ttatgattct tctcgcttcc ggcggcatcg ggatgcccgc    4980
gttgcaggcc atgctgtcca ggcaggtaga tgacgaccat cagggacagc ttcaaggatc    5040
gctcgcggct cttaccagcc taacttcgat cactggaccg ctgatcgtca cggcgattta    5100
tgccgcctcg gcgagcacat ggaacgggtt ggcatggatt gtaggcgccg ccctatacct    5160
tgtctgcctc cccgcgttgc gtcgcggtgc atggagccgg ccacctcga cctgaatgga    5220 agccggcggc acctcgctaa cggattcacc actccaagaa ttggagccaa tcaattcttg    5280
cggagaactg tgaatgcgca aaccaaccct tggcagaaca tatccatcgc gtccgccatc    5340
tccagcagcc gcacgcggcg catctcgggc agcgttgggt cctggccacg ggtgcgcatg    5400
atcgtgctcc tgtcgttgag gacccggcta ggctggcggg gttgccttac tggttagcag    5460
aatgaatcac cgatacgcga gcgaacgtga agcgactgct gctgcaaaac gtctgcgacc    5520
tgagcaacaa catgaatggt cttcggtttc cgtgtttcgt aaagtctgga aacgcggaag    5580
tcccctacgt gctgctgaag ttgcccgcaa cagagagtgg aaccaaccgg tgataccacg    5640
atactatgac tgagagtcaa cgccatgagc ggcctcattt cttattctga gttacaacag    5700
tccgcaccgc tgtccggtag ctccttccgg tgggcgcggg gcatgactat cgtcgccgca    5760
cttatgactg tcttctttat catgcaactc gtaggacagg tgccggcagc gcccaacagt    5820
cccccggcca cggggcctgc caccatacccc acgccgaaac aagcgccctg caccattatg    5880
ttccggatct gcatcgcagg atgctgctgg ctaccctgtg aacacctac atctgtatta    5940 acgaagcgct aaccgttttt atcaggctct gggaggcaga ataaatgatc atatcgtcaa    6000
ttattacctc cacggggaga gcctgagcaa actggcctca ggcatttgag aagcacacgg    6060
tcacactgct tccggtagtc aataaaccgg taaaccagca atagacataa gcggctattt    6120
aacgaccctg ccctgaaccg acgacccggt cgaatttgct ttcgaatttc tgccattcat    6180
ccgcttatta tcacttattc aggcgtagca ccaggcgttt aagggcacca ataactgcct    6240
taaaaaaatt acgccccgcc ctgccactca tcgcagtact gttgtaattc attaagcatt    6300
ctgccgacat ggaagccatc acagacggca tgatgaacct gaatcgccag cggcatcagc    6360
accttgtcgc cttgcgtata atatttgccc atggtgaaaa cggggcgaa gaagttgtcc    6420 atattggcca cgtttaaatc aaaactggtg aaactcaccc agggattggc tgagacgaaa    6480
aacatattct caataaaccc tttagggaaa taggccaggt tttcaccgta acacgccaca    6540
tcttgcgaat atatgtgtag aaactgccgg aaatcgtcgt ggtattcact ccagagcgat    6600
gaaaacgttt cagtttgctc atggaaaacg gtgtaacaag ggtgaacact atcccatatc    6660
accagctcac cgtctttcat tgccatacg                                      6689
```

<210> SEQ ID NO 25
<211> LENGTH: 6249
<212> TYPE: DNA
<213> ORGANISM: Artificial
<220> FEATURE:
<223> OTHER INFORMATION: Designed plasmid DNA, pAC-FDSI78G,Y81A-idi

<400> SEQUENCE: 25

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
```

```
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacagga aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccctg gcggctccct     960 cgtgcgctct cctgttcctg cctttcggtt taccggtgtc attccgctgt tatggccgcg    1020
tttgtctcat tccacgcctg acactcagtt ccgggtaggc agttcgctcc aagctggact    1080
gtatgcacga accccccgtt cagtccgacc gctgcgcctt atccggtaac tatcgtcttg    1140
agtccaaccc ggaaagacat gcaaaagcac cactggcagc agccactggt aattgattta    1200
gaggagttag tcttgaagtc atgcgccggt taaggctaaa ctgaaaggac aagttttggt    1260
gactgcgctc ctccaagcca gttacctcgg ttcaaagagt tggtagctca gagaaccttc    1320
gaaaaaccgc cctgcaaggc ggttttttcg ttttcagagc aagagattac gcgcagacca    1380
aaacgatctc aagaagatca tcttattaat cagataaaat atttcaagat ttcagtgcaa    1440
tttatctctt caaatgtagc acctgaagtc agccccatac gatataagtt gtaattctca    1500
tgtttgacag cttatcgtga ggtttcccga ctggaaagcg ggcagtgagc gcaacgcaat    1560
taatgtgagt tagctcactc attaggcacc ccaggcttta cactttatgc ttccggctcg    1620
tatgttgtgt ggaattgtga gcggataaca atttcacaca ggaaacacat atggaattct    1680
ctagaaggag gattacaaaa tgcaaacgga acacgtcatt ttattgaatg cacagggagt    1740
tcccacgggt acgctggaaa agtatgccgc acacacggca gacaccgct tacatctcgc    1800 gttctccagt tggctgttta atgccaaagg acaattatta gttacccgcc gcgcactgag    1860
caaaaaagca tggcctggcg tgtggactaa ctcggtttgt gggcacccac aactgggaga    1920
aagcaacgaa gacgcagtga tccgccgttg ccgttatgag cttggcgtgg aaattacgcc    1980
tcctgaatct atctatcctg actttcgcta ccgcgccacc gatccgagtg cattgtgga    2040 aaatgaagtg tgtccggtat tgccgcacg caccactagt gcgttacaga tcaatgatga    2100
tgaagtgatg gattatcaat ggtgtgattt agcagatgta ttacacggta ttgatgccac    2160
gccgtgggcg ttcagtccgt ggatggtgat gcaggcgaca aatcgcgaag ccagaaaacg    2220
attatctgca tttacccagc ttaaataact cgaggggccc ggcgcctgat gcggtatttt    2280
ctccttacgc atctgtgcgg tatttcactg catcgataag ctttaatgcg gtagtttatc    2340
acagttaaat tgctaacgca gtcaggcacc gtgtatgaaa tctaacaatg cgctcatcgt    2400
catcctcggc accgtcaccc tggatgctgt aggcataggc ttggttatgc cggtactgcc    2460
gggcctcttg cggatatcg tccattccga cagcatcgcc agtcactatg gcgtgctgct    2520
agcgctatat gcgttgatgc aatttctatg cgcacccgtt ctcggagcac tgtccgaccg    2580
```

| | |
|---|---|
| ctttggccgc cgcccagtcc tgctcgcttc gctacttgga gccactatcg actacgcgat | 2640 |
| catggcgacc acacccgtcc tgtggatccc gtggaggttt cccgactgga aagcgggcag | 2700 |
| tgagcgcaac gcaattaatg tgagttagct cactcattag gcaccccagg ctttacactt | 2760 |
| tatgcttccg gctcgtatgt tgtgtggaat tgtgagcgga taacaatttc acacaggaaa | 2820 |
| cacatatgga attctctaga aggaggagta agcgatggcg cagcttttcag ttgaacagtt | 2880 |
| tctcaacgag caaaaacagg cggtggaaac agcgctctcc cgttatatag agcgcttaga | 2940 |
| agggccggcg aagctgaaaa aggcgatggc gtactcattg gaggccggcg gcaaacgaat | 3000 |
| ccgtccgttg ctgcttctgt ccaccgttcg ggcgctcggc aaagacccgg cggtcggatt | 3060 |
| gcccgtcgcc tgcgcgattg aaatgggtca tacggcatct ttgatccatg atgatttgcc | 3120 |
| gagcatggac aacgatgatt tgcggcgcgcg caagccgacg aaccataaag tgttcggcga | 3180 |
| ggcgatggcc atcttggcgg gggacgggtt gttgacgtac gcgtttcaat tgatcaccga | 3240 |
| aatcgacgat gagcgcatcc ctccttccgt ccggcttcgg ctcatcgaac ggctggcgaa | 3300 |
| agcggccggt ccggaaggga tggtcgccgg tcaggcagcc gatatggaag gagaggggaa | 3360 |
| aacgctgacg ctttcggagc tcgaatacat tcatcggcat aaaaccggga aaatgctgca | 3420 |
| atacagcgtg cacgccggcg ccttgatcgg cggcgctgat gcccggcaaa cgcgggagct | 3480 |
| tgacgaattc gccgcccatc taggccttgc ctttcaaatt cgcgatgata ttctcgatat | 3540 |
| tgaaggggca gaagaaaaaa tcggcaagcc ggtcggcagc gaccaaagca caacaaagc | 3600 |
| gacgtatcca gcgttgctgt cgcttgccgg cgcgaaggaa aagttggcgt tccatatcga | 3660 |
| ggcggcgcag cgccatttac ggaacgctga cgttgacggc gccgcgctcg cctatatttg | 3720 |
| cgaactggtc gccgcccgcg accattaact cgagggccc ggcgcctgat gcggtatttt | 3780 |
| ctccttacgc atctgtgcgg tatttcacgt gcgctcgagg ggcccggcgc ctgatgcggt | 3840 |
| attttctcct tacgcatctg tgcggtattt cacggatcct ctacgccgga cgcatcgtgg | 3900 |
| ccggcatcac cggcgccaca ggtgcggttg ctggcgccta tcgccgac atcaccgatg | 3960 |
| gggaagatcg ggctcgccac ttcgggctca tgagcgcttg tttcggcgtg ggtatggtgg | 4020 |
| caggccccgt ggccggggga ctgttgggcg ccatctcctt gcatgcacca ttccttgcgg | 4080 |
| cggcggtgct caacggcctc aacctactac tgggctgctt cctaatgcag gagtcgcata | 4140 |
| agggagagcg tcgaccgatg cccttgagag ccttcaaccc agtcagctcc ttccggtggg | 4200 |
| cgcggggcat gactatcgtc gccgcactta tgactgtctt ctttatcatg caactcgtag | 4260 |
| gacaggtgcc ggcagcgctc tgggtcattt tcggcgagga ccgctttcgc tggagcgcga | 4320 |
| cgatgatcgg cctgtcgctt gcggtattcg gaatcttgca cgccctcgct caagccttcg | 4380 |
| tcactggtcc cgccaccaaa cgtttcggcg agaagcaggc cattatcgcc ggcatggcgg | 4440 |
| ccgacgcgct gggctacgtc ttgctggcgt tcgcgacgcg aggctggatg gccttcccca | 4500 |
| ttatgattct tctcgcttcc ggcggcatcg ggatgcccgc gttgcaggcc atgctgtcca | 4560 |
| ggcaggtaga tgacgaccat cagggacagc ttcaaggatc gctcgcggct cttaccagcc | 4620 |
| taacttcgat cactggaccg ctgatcgtca cggcgattta tgccgcctcg gcgagcacat | 4680 |
| ggaacgggtt ggcatggatt gtaggcgccg ccctatacct tgtctgcctc cccgcgttgc | 4740 |
| gtcgcggtgc atggagccgg gccacctcga cctgaatgga agccggcggc acctcgctaa | 4800 |
| cggattcacc actccaagaa ttggagccaa tcaattcttg cggagaactg tgaatgcgca | 4860 |
| aaccaaccct tggcagaaca tatccatcgc gtccgccatc tccagcagcc gcacgcggcg | 4920 |

```
catctcgggc agcgttgggt cctggccacg ggtgcgcatg atcgtgctcc tgtcgttgag    4980
gacccggcta ggctggcggg gttgccttac tggttagcag aatgaatcac cgatacgcga    5040
gcgaacgtga agcgactgct gctgcaaaac gtctgcgacc tgagcaacaa catgaatggt    5100
cttcggtttc cgtgtttcgt aaagtctgga aacgcggaag tccctacgt gctgctgaag     5160 ttgcccgcaa cagagagtgg aaccaaccgg tgataccacg atactatgac tgagagtcaa    5220
cgccatgagc ggcctcattt cttattctga gttacaacag tccgcaccgc tgtccggtag    5280
ctccttccgg tgggcgcggg gcatgactat cgtcgccgca cttatgactg tcttctttat    5340
catgcaactc gtaggacagg tgccggcagc gcccaacagt cccccggcca cggggcctgc    5400
caccataccc acgccgaaac aagcgccctg caccattatg ttccggatct gcatcgcagg    5460
atgctgctgg ctaccctgtg aacacctac atctgtatta acgaagcgct aaccgttttt     5520
atcaggctct gggaggcaga ataaatgatc atatcgtcaa ttattacctc cacggggaga    5580
gcctgagcaa actggcctca ggcatttgag aagcacacgg tcacactgct tccggtagtc    5640
aataaaccgg taaccagca atagacataa gcggctattt aacgaccctg ccctgaaccg     5700
acgaccgggt cgaatttgct ttcgaatttc tgccattcat ccgcttatta tcacttattc    5760
aggcgtagca ccaggcgttt aagggcacca ataactgcct taaaaaaatt acgccccgcc    5820
ctgccactca tcgcagtact gttgtaattc attaagcatt ctgccgacat ggaagccatc    5880
acagacggca tgatgaacct gaatcgccag cggcatcagc accttgtcgc cttgcgtata    5940
atatttgccc atggtgaaaa cggggggcgaa gaagttgtcc atattggcca cgtttaaatc    6000
aaaactggtg aaactcaccc agggattggc tgagacgaaa aacatattct caataaaccc    6060
tttagggaaa taggccaggt tttcaccgta acacgccaca tcttgcgaat atatgtgtag    6120
aaactgccgg aaatcgtcgt ggtattcact ccagagcgat gaaaacgttt cagtttgctc    6180
atggaaaacg gtgtaacaag ggtgaacact atcccatatc accagctcac cgtctttcat    6240
tgccatacg                                                            6249

<210> SEQ ID NO 26
<211> LENGTH: 3364
<212> TYPE: DNA
<213> ORGANISM: Artificial
<220> FEATURE:
<223> OTHER INFORMATION: Designed plasmid DNA, pUC-CrtMF26A,W38A,F233S

<400> SEQUENCE: 26
ttggccgatt cattaatgca gctggcacga caggtttccc gactggaaag cgggcagtga     60
gcgcaacgca attaatgtga gttagctcac tcattaggca ccccaggctt tacactttat    120
gcttccggct cgtatgttgt gtggaattgt gagcggataa caatttcaca caggaaacac    180
atatggaatt ctctagaagg aggattacaa atgacaatg atgaatatga attttaaata     240
ttgtcataaa atcatgaaga acattcaaa aagcttttct tacgctgcgg acttgttacc      300
agaagatcaa agaaaagcgg ttgcggcaat ttatgctgtg tgtcgtaaaa ttgatgacag    360
tatagatgtt tatggcgata ttcaattttt aaatcaaata aagaagata tacaatctat     420 tgaaaaatac ccatatgaac atcatcactt tcaaagtgat cgtagaatca tgatggcgct    480
tcagcatgtt gcacaacata aaatatcgc ctttcaatct ttttataatc tcattgatac     540
tgtatataaa gatcaacatt ttacaatgtt tgaaacggac gctgaattat tcggatattg    600
ttatggtgtt gctggtacag taggtgaagt attgacgccg atttttaagtg atcatgaaac    660 acatcagaca tacgatgtcg caagaagact tggtgaatcg ttgcaattga ttaatatatt    720
```

```
aagagatgtc ggtgaagatt ttgacaatga acggatatat tttagtaagc aacgattaaa    780
gcaatatgaa gttgatattg ctgaagtgta ccaaaatggt gttaataatc attatattga    840
cttatgggaa tattatgcag ctatcgcaga aaaagatttt caagatgtta tggatcaaat    900
caaagtatct agtattgaag cacaaccaat catagaatta gcagcacgta tatatattga    960
aatactggac gaagtgagac aggctaacta tacattacat gaacgtgttt ttgtggataa   1020
gaggaaaaag gcaaagttgt ttcatgaaat aaatagtaaa tatcatagaa tatagctcga   1080
ggggcccggc gcctgatgcg gtattttctc cttacgcatc tgtgcggtat tcacaccgc    1140 atatatggtg cactctcagt acaatctgct ctgatgccgc atagttaagc cagccccgac   1200
acccgccaac acccgctgac gcgccctgac gggcttgtct gctcccggca tccgcttaca   1260
gacaagctgt gaccgtctcc gggagctgca tgtgtcagag gttttcaccg tcatcaccga   1320
aacgcgcgag acgaaagggc ctcgtgatac gcctattttt ataggttaat gtcatgataa   1380
taatggtttc ttagacgtca ggtggcactt tcggggaaa tgtgcgcgga acccctattt    1440
gtttattttt ctaaatacat tcaaatatgt atccgctcat gagacaataa ccctgataaa   1500
tgcttcaata atattgaaaa aggaagagta tgagtattca acatttccgt gtcgccctta   1560
ttcccttttt tgcggcattt tgccttcctg tttttgctca cccagaaacg ctggtgaaag   1620
taaaagatgc tgaagatcag ttgggtgcac gagtgggtta catcgaactg gatctcaaca   1680
gcggtaagat ccttgagagt tttcgccccg aagaacgttt tccaatgatg agcacttta    1740 aagttctgct atgtggcgcg gtattatccc gtattgacgc cgggcaagag caactcggtc   1800
gccgcataca ctattctcag aatgacttgg ttgagtactc accagtcaca gaaaagcatc   1860
ttacggatgg catgacagta agagaattat gcagtgctgc cataaccatg agtgataaca   1920
ctgcggccaa cttacttctg acaacgatcg gaggaccgaa ggagctaacc gcttttttgc   1980
acaacatggg ggatcatgta actcgcctg atcgttggga accggagctg aatgaagcca    2040
taccaaacga cgagcgtgac accacgatgc ctgtagcaat ggcaacaacg ttgcgcaaac   2100
tattaactgg cgaactactt actctagctt cccggcaaca attaatagac tggatggagg   2160
cggataaagt tgcaggacca cttctgcgct cggcccttcc ggctggctgg tttattgctg   2220
ataaatctgg agccggtgag cgtgggtctc gcggtatcat tgcagcactg gggccagatg   2280
gtaagccctc ccgtatcgta gttatctaca cgacggggag tcaggcaact atggatgaac   2340
gaaatagaca gatcgctgag ataggtgcct cactgattaa gcattggtaa ctgtcagacc   2400
aagtttactc atatatactt tagattgatt taaaacttca ttttttaattt aaaaggatct   2460 aggtgaagat cctttttgat aatctcatga ccaaaatccc ttaacgtgag ttttcgttcc   2520
actgagcgta gaccccgta gaaaagatca aggatcttc ttgagatcct ttttttctgc     2580
gcgtaatctg ctgcttgcaa acaaaaaaac caccgctacc agcggtggtt tgtttgccgg   2640
atcaagagct accaactctt tttccgaagg taactggctt cagcagagcg cagataccaa   2700
atactgtcct tctagtgtag ccgtagttag gccaccactt caagaactct gtagcaccgc   2760
ctacatacct cgctctgcta atcctgttac cagtggctgc tgccagtggc gataagtcgt   2820
gtcttaccgg gttggactca agacgatagt taccggataa ggcgcagcgg tcgggctgaa   2880
cggggggttc gtgcacacag cccagcttgg agcgaacgac ctacaccgaa ctgagatacc   2940
tacagcgtga gctatgagaa agcgccacgc ttcccgaagg gagaaaggcg gacaggtatc   3000
cggtaagcgg cagggtcgga acaggagagc gcacgaggga gcttccaggg ggaaacgcct   3060
```

-continued

```
ggtatcttta tagtcctgtc gggtttcgcc acctctgact tgagcgtcga tttttgtgat    3120
gctcgtcagg ggggcggagc ctatggaaaa acgccagcaa cgcggccttt ttacggttcc    3180
tggccttttg ctggccttt gctcacatgt tctttcctgc gttatcccct gattctgtgg     3240
ataaccgtat taccgccttt gagtgagctg ataccgctcg ccgcagccga acgaccgagc    3300
gcagcgagtc agtgagcgag gaagcggaag agcgcccaat acgcaaaccg cctctccccg    3360
cgcg                                                                  3364
```

<210> SEQ ID NO 27
<211> LENGTH: 492
<212> TYPE: PRT
<213> ORGANISM: Artificial
<220> FEATURE:
<223> OTHER INFORMATION: Pantoea ananatis crtI mutant (N304P)

<400> SEQUENCE: 27

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Glu Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
                245                 250                 255

Val His Leu Glu Asp Gly Arg Arg Phe Leu Thr Gln Ala Val Ala Ser
            260                 265                 270

Asn Ala Asp Val Val His Thr Tyr Arg Asp Leu Leu Ser Gln His Pro
        275                 280                 285

Ala Ala Val Lys Gln Ser Asn Lys Leu Gln Thr Lys Arg Met Ser Pro
    290                 295                 300
```

```
Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile Asp
                325                 330                 335

Glu Ile Phe Asn His Asp Gly Leu Ala Glu Asp Phe Ser Leu Tyr Leu
            340                 345                 350

His Ala Pro Cys Val Thr Asp Ser Ser Leu Ala Pro Glu Gly Cys Gly
        355                 360                 365

Ser Tyr Tyr Val Leu Ala Pro Val Pro His Leu Gly Thr Ala Asn Leu
    370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Gln Leu Asn Ala Tyr His
            420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Thr Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490
```

<210> SEQ ID NO 28
<211> LENGTH: 1479
<212> TYPE: DNA
<213> ORGANISM: Artificial
<220> FEATURE:
<223> OTHER INFORMATION: Pantoea ananatis crtI mutant (N304P)

<400> SEQUENCE: 28

```
atgaaaccaa ctacggtaat tggtgcaggc ttcggtggcc tggcactggc aattcgtcta      60
caagctgcgg ggatccccgt cttactgctt gaacaacgtg ataaacccgg cggtcgggct     120
tatgtctacg aggatcaggg gtttaccttt gatgcaggcc cgacggttat caccgatccc     180
agtgccattg aagaactgtt tgcactggca ggaaaacagt taaagagta tgtcgaactg     240 ctgccggtta cgccgtttta ccgcctgtgt tgggagtcag ggaaggtctt taattacgat     300
aacgatcaaa cccggctcga agcgcagatt cagcagttta tccccgcga tgtcgaaggt     360 tatcgtcagt ttctggacta ttcacgcgcg gtgtttaaag aaggctatct aaagctcggt     420 actgtcccctt ttttatcgtt cagagacatg cttcgcgccg cacctcaact ggcgaaactg     480
caggcatgga gaagcgttta cagtaaggtt gccagttaca tcgaagatga acatctgcgc     540
caggcgtttt ctttccactc gctgttggtg gcggcaatc ccttcgccac ctcatccatt     600
tatacgttga tacacgcgct ggagcgtgag tgggcgtct ggtttccgcg tggcggcacc     660
ggcgcattag ttcaggggat gataaagctg tttcaggatc tgggtggcga agtcgtgtta     720
aacgccagag tcagccatat ggaaacgaca ggaaacaaga ttgaagccgt gcatttagag     780
gacggtcgca ggttcctgac gcaagccgtc gcgtcaaatg cagatgtggt tcatacctat     840
cgcgacctgt taagccagca ccctgccgcg gttaagcagt ccaacaaact gcagactaag     900
cgcatgagtc cttctctgtt tgtgctctat tttggtttga atcaccatca tgatcagctc     960
gcgcatcaca cggtttgttt cggcccgcgt taccgcgagc tgattgacga aattttttaat    1020
```

```
catgatggcc tcgcagagga cttctcactt tatctgcacg cgccctgtgt cacggattcg    1080
tcactggcgc ctgaaggttg cggcagttac tatgtgttgg cgccggtgcc acatttaggc    1140
accgcgaacc tcgactggac ggttgagggg ccaaaactac gcgaccgtat ttttgcgtac    1200
cttgagcagc attacatgcc tggcttacgg agtcagctgg tcacgcaccg gatgtttacg    1260
ccgtttgatt ttcgcgacca gcttaatgcc tatcatggct cagcctttc tgtggagccc     1320 gttcttaccc agagcgcctg gtttcggccg cataaccgcg ataaaaccat tactaatctc    1380
tacctggtcg gcgcaggcac gcatcccggc gcaggcattc ctggcgtcat cggctcggca    1440
aaagcgacag caggtttgat gctggaggat ctgatttga                           1479
```

METHOD FOR PRODUCING CAROTENOIDS EACH HAVING 50 CARBON ATOMS

This application is a continuation of U.S. patent application Ser. No. 14/124,256, filed Dec. 6, 2013, now U.S. Pat. No. 9,562,220, which is a National Stage Application of PCT/JP2012/064817, filed Jun. 8, 2012, which claims priority from Japanese Patent Application No. 2011-130326, filed Jun. 10, 2011.

TECHNICAL FIELD

The present invention relates to a production method for a carotenoid having 50 carbon atoms, including the step of culturing, in a medium, a cell transformed with a mutant phytoene desaturase gene.

BACKGROUND ART

There exist various carotenoids in nature. Approximately 750 kinds of carotenoids have been identified heretofore, and many of the carotenoids have been shown to have useful physiological functions and industrial applicability such as an antioxidant activity or an antitumor activity, or a use as a functional pigment molecule. In general, carotenoids are compounds classified as tetraterpenes formed of an isoprene backbone of 30 or 40 carbon atoms. In nature, a linear backbone of 30 or 40 carbon atoms is formed as a basic backbone and then subjected to various modifications such as cyclization. Structural diversity of the carotenoids is attributed to diversity of such modifications. Further, carotenoids are known to have physiological activities greatly varying depending on structural differences based on the diversity of the modifications.

A large number of carotenoids have been obtained by isolation and extraction from nature such as plants, or by chemical synthesis. Recently, however, production utilizing microbial fermentation has also been performed. In order to establish biosynthetic pathways for rare carotenoids, which exist in nature in only trace amounts, and unnatural carotenoids, which do not exist in nature, research has been made by many researchers (Non Patent Literatures 1 to 8 and Patent Literature 1). In Non Patent Literatures 1 to 6, carotenoids having various structures have been obtained by synthesis based on the so-called combinatorial biosynthesis technique. The combinatorial biosynthesis is a technology involving altering biosynthetic pathways of microorganisms using a genetic engineering technique and allowing the microorganisms to produce a compound of interest. Modifying enzymes that provide various structures to carotenoids have the "locally specific" nature of recognizing and acting on only part of substrates. Based on such nature of the modified substrates, the combinatorial biosynthesis of the carotenoids has been performed (Non Patent Literature 9). Meanwhile, in Non Patent Literatures 7, 8, and 11 and Patent Literature 1, biosynthesis of various unnatural carotenoids has been achieved by a method involving constructing a metabolic pathway using an activity of an enzyme that cannot be found in nature and is created using protein engineering.

As described above, the carotenoids that exist in nature have backbones of 30 carbon atoms and 40 carbon atoms. The former is derived from 4,4'-diapophytoene, which is synthesized via head-to-head condensation of two molecules of farnesyl diphosphate ($C_{15}PP$). The latter is derived from phytoene (carotenoid backbone compound of 40 carbon atoms), which is synthesized via head-to-head condensation of two molecules of geranylgeranyl diphosphate ($C_{20}PP$). The former is a key component of biosynthetic pathways for 10-odd kinds of carotenoids known to exist in nature, and the latter is a key component of biosynthetic pathways for about 700 or more kinds of carotenoids.

Further, there is a report that a carotenoid having a backbone of 50 carbon atoms, which is larger than that of 40 carbon atoms, exists in nature (Patent Literature 2). The carotenoid having a backbone of 50 carbon atoms is synthesized by binding an isoprene unit to a carotenoid having 40 carbon atoms "as addition" so as to increase the total number of carbon atoms to 45 and 50 (Non Patent Literature 10). In a synthetic pathway for a backbone of 40 or more carbon atoms, such as a backbone of 50 carbon atoms or 60 carbon atoms, synthesis is performed by using, for example, geranylfarnesyl diphosphate ($C_{25}PP$) or hexaprenyl diphosphate ($C_{30}PP$) as a raw material. Although the carotenoid having a backbone of 40 or more carbon atoms is expected to have many potentialities for physiological and pigment functions and the like different from conventional ones, there is no detailed report on its synthetic pathways in nature, and there are few reports on its artificial biosynthetic pathways.

Dr. Umeno, one of the inventors of the present invention, developed an enzyme having a function of synthesizing a carotenoid backbone compound of 50 carbon atoms via condensation of two molecules of geranylfarnesyl diphosphate ($C_{25}PP$) by altering a synthase (CrtM) for a carotenoid having 30 carbon atoms derived from *Staphylococcus aureus*. In addition, Dr. Umeno succeeded for the first time in the world in co-expressing the enzyme with an appropriate precursor synthase in *Escherichia coli* to produce 16,16'-diisopentenylphytoene, a carotenoid backbone compound of 50 carbon atoms (Non Patent Literature 7). However, in the synthetic pathway in Non Patent Literature 7, carotenoids having backbones of, for example, 30 carbon atoms, 40 carbon atoms, and 45 carbon atoms were synthesized simultaneously with that having a backbone of 50 carbon atoms. Even when a wild-type phytoene desaturase was added in this pathway, about 75% of the carotenoid backbone compound of 50 carbon atoms still remained without being desaturated, resulting in poor synthetic efficiency (Non Patent Literature 8).

CITATION LIST

Patent Literature

[PTL 1] US 2002/0051998 A
[PTL 2] JP 07-132096 A

Non Patent Literature

[NPL 1] Takaichi S. et al., Eur J Biochem 241, 291-6 (1996)
[NPL 2] Yokoyama A. et al., Tetrahedron Lett. 39, 3709-12 (1998)
[NPL 3] Albrecht M. et al., Nat. Biotechnol. 18, 843-6 (2000)
[NPL 4] Lee P. C. et al., Chem. Biol. 10, 453-462 (2003)
[NPL 5] Mijts B. N. et al., Chem. Biol. 12, 453-460 (2005)
[NPL 6] Umeno D. et al., Appl Environ Microbiol 69, 3573-3579 (2003)
[NPL 7] Umeno D. et al., J Bacteriol, 186, 1531-1536 (2004)
[NPL 8] Tobias A. V. et al., Biochim Biophys Acta, 1761, 235-246 (2006)
[NPL 9] Umeno D. et al., Microbiol Mol Biol Rev 69, 51-78 (2005)

[NPL 10] Krubasik P. et al., Eur J Biochem 268, 3702-3708 (2001)
[NPL 11] Schmidt-Dannert C. et al., Nature Biotech. 18, 750-753 (2000)

SUMMARY OF INVENTION

Technical Problem

A carotenoid having 50 carbon atoms has a large backbone as compared to a carotenoid having 40 carbon atoms, and hence has such superiority as a substance that conjugated double bonds having a large size can be accommodated. It is considered that, when a carotenoid backbone compound of 50 carbon atoms can be synthesized and desaturated as in the synthetic pathway for the carotenoid having 40 carbon atoms in nature, the resultant product can be used in combination with various modifying enzymes to produce carotenoids having 50 carbon atoms having a great variety of structures and physiological activities. An object of the present invention is to provide a production method for various carotenoids having 50 carbon atoms, including efficiently desaturating a carotenoid backbone compound of 50 carbon atoms.

Solution to Problem

The inventors of the present invention have made intensive studies in order to achieve the object. Consequently, the inventors have found that a carotenoid backbone compound of 50 carbon atoms can be efficiently desaturated with a mutant phytoene desaturase obtained by introducing a mutation into a phytoene desaturase (CrtI), and have focused attention on the fact that a carotenoid having 50 carbon atoms can be efficiently and simply synthesized by culturing a cell having introduced therein a mutant phytoene desaturase gene, thus achieving the present invention.

That is, the present invention relates to the following items.

1. A method of producing a carotenoid having 50 carbon atoms, comprising: culturing, in a medium, a cell transformed with a mutant phytoene desaturase gene; and
obtaining the carotenoid having 50 carbon atoms from a culture after the culturing,
wherein the mutant phytoene desaturase gene has an introduced mutation to encode a mutant phytoene desaturase having an enhanced activity to desaturate a carotenoid backbone compound of 50 carbon atoms.

2. The method of producing a carotenoid having 50 carbon atoms according to the above-described item 1, wherein
the mutant phytoene desaturase gene has an introduced mutation to encode a mutant phytoene desaturase having an enhanced activity to desaturate a carotenoid backbone compound of 50 carbon atoms has been introduced, and
the mutation causes a substitution of an amino acid corresponding to at least one amino acid selected from asparagine at position 304, phenylalanine at position 339, isoleucine at position 338, aspartic acid at position 395, and isoleucine at position 228 in an amino acid sequence set forth in SEQ ID NO: 1.

3. The method of producing a carotenoid having 50 carbon atoms according to the above-described item 1 or 2, wherein
the mutant phytoene desaturase gene has an introduced mutation to encode a mutant phytoene desaturase having an enhanced activity to desaturate a carotenoid backbone compound of 50 carbon atoms has been introduced, and
the mutation causes at least a substitution of an amino acid corresponding to asparagine at position 304 in SEQ ID NO: 1 by proline or serine.

4. The method of producing a carotenoid having 50 carbon atoms according to any one of the above-described items 1 to 3, wherein
the mutant phytoene desaturase gene has an introduced mutation to encode a mutant phytoene desaturase having an enhanced activity to desaturate a carotenoid backbone compound of 50 carbon atoms has been introduced, and
the mutant phytoene desaturase gene is obtained by introducing the mutation into a phytoene desaturase gene derived from *Pantoea ananatis*.

5. The method of producing a carotenoid having 50 carbon atoms according to any one of the above-described items 1 to 4, wherein the cell is *Escherichia coli* or yeast.

6. The method of producing a carotenoid having 50 carbon atoms according to any one of the above-described items 1 to 5, wherein the cell transformed with the mutant phytoene desaturase gene is further transformed with a gene encoding an enzyme that synthesizes the carotenoid backbone compound of 50 carbon atoms via condensation of two molecules of geranylfarnesyl diphosphate.

7. The method of producing a carotenoid having 50 carbon atoms according to any one of the above-described items 1 to 6, wherein the cell as defined in any one of the above-described items 1 to 6 is further transformed with a gene encoding an enzyme that synthesizes geranylfarnesyl diphosphate from farnesyl diphosphate and/or geranylgeranyl diphosphate.

8. The method of producing a carotenoid having 50 carbon atoms according to any one of the above-described items 1 to 7, wherein the cell as defined in any one of the above-described items 1 to 7 is further transformed with a gene encoding an enzyme that cyclizes ends of a desaturated carotenoid having 50 carbon atoms obtained by desaturating the carotenoid backbone compound of 50 carbon atoms.

9. The method of producing a carotenoid having 50 carbon atoms according to the above-described item 8, wherein
the cyclization as defined in the above-described item 8 comprises β-cyclization, and
the cell as defined in the above-described item 8 is further transformed with a gene encoding an enzyme that hydroxylates a β-ring and/or an enzyme that ketolates a β-ring in a carotenoid having 50 carbon atoms and having the β-ring at an end thereof.

10. The method of producing a carotenoid having 50 carbon atoms according to any one of the above-described items 1 to 7, wherein the cell as defined in any one of the above-described items 1 to 7 is further transformed with a gene encoding an enzyme that oxidizes a desaturated carotenoid having 50 carbon atoms obtained by desaturating the carotenoid backbone compound of 50 carbon atoms.

11. A mutant phytoene desaturase gene, into which a mutation to encode a mutant phytoene desaturase having an enhanced activity to desaturate a carotenoid backbone compound of 50 carbon atoms has been introduced.

12. The mutant phytoene desaturase gene according to the above-described item 11, wherein the mutation to encode a mutant phytoene desaturase having an enhanced activity to desaturate a carotenoid backbone compound of 50 carbon atoms causes a substitution of an amino acid corresponding to at least one amino acid selected from asparagine at position 304, phenylalanine at position 339, isoleucine at position 338, aspartic acid at position 395, and isoleucine at position 228 in an amino acid sequence set forth in SEQ ID NO: 1.

13. The mutant phytoene desaturase gene according to the above-described item 11 or 12, wherein the mutation of the mutant phytoene desaturase gene causes at least a substitution of an amino acid corresponding to asparagine at position 304 in SEQ ID NO: 1 by proline or serine.

14. A mutant phytoene desaturase, which is encoded by the mutant phytoene desaturase gene according to any one of the above-described items 11 to 13.

15. A cell producing a carotenoid having 50 carbon atoms by desaturating a carotenoid backbone compound of 50 carbon atoms, which is transformed with the mutant phytoene desaturase gene according to any one of the above-described items 11 to 13.

Advantageous Effects of Invention

The production method of the present invention allows the carotenoid backbone compound of 50 carbon atoms to be efficiently desaturated, and thus the carotenoids having 50 carbon atoms having a great variety of structures can be produced. Some enzymes including a wild-type phytoene desaturase exhibited a desaturation efficiency of only about several % at maximum for the carotenoid backbone compound of 50 carbon atoms. In contrast, the production method of the present invention has provided drastically increased desaturation efficiency. Thus, a desaturated carotenoid having 50 carbon atoms can be delivered to downstream modifying enzymes, and thereby a great variety of carotenoids having 50 carbon atoms can be produced.

A carotenoid backbone compound of 40 carbon atoms (30 carbon atoms in certain species of bacteria) free of oxygen and the like undergoes various modifications such as oxygenation. As a result, carotenoids acquire a great variety of structures. The most major carotene in nature is β-carotene having a β-ring, and various enzymes that modify the β-ring exist in nature. According to the production method of the present invention, a carotenoid having 50 carbon atoms and a β-ring can be synthesized. In addition, a great variety of carotenoids can be produced by using various enzymes that modify the β-ring.

The carotenoid having 50 carbon atoms produced by the production method of the present invention is expected to, for example, have the following potentialities: an antioxidant function improved as compared to a conventional carotenoid; a color gamut as a pigment extended to a range that has not been reported heretofore; and property of hardly undergoing destructive metabolism.

Further, in the production method of the present invention, conventional culture media and conditions may be used, and hence the carotenoid having 50 carbon atoms can be simply synthesized.

In addition, the production method of the present invention can be utilized for carrying out the highly efficient synthesis of a desaturated $C_{55}$ carotenoid, a desaturated $C_{60}$ carotenoid, and the like.

BRIEF DESCRIPTION OF THE DRAWINGS

FIG. 2A illustrates pAC-fds$_{Y81A,V157A}$-crtM$_{F26A,W38A,F233S}$, which was produced by inserting lac promoter/operator (lacPP)-crtM$_{F26A,W38A,F233S}$ and lac promoter/operator (lacPO)-fds$_{Y81A, V157A}$ into a pACmod vector. FIG. 2B illustrates pUC-pBAD-crtI*, which was produced by removing the lac promoter/operator from a pUC18Nm vector, inserting an araC gene/araBAD promoter sequence (derived from a pBADHisA vector), and inserting crtI variants (crtI*) downstream of the promoter. FIG. 2C illustrates pUC-pBAD-crtI*-crtY, which was produced by inserting crtY downstream of the crtI variants in pUC-pBAD-crtI*. FIG. 2D illustrates pUC-pBAD-crtI*-crtWZY, which was produced by inserting crtW, crtZ, and crtY downstream of the crtI variants in pUC-pBAD-crtI*. FIG. 2E illustrates pUC-pBAD-crtI*-crtA, which was produced by inserting crtA downstream of the crtI variants in pUC-pBAD-crtI*. FIG. 2F illustrates pUC-fds$_{Y81A,V157A}$, which was produced by inserting an fds$_{Y81A,V157A}$ gene downstream of lacPO in a pUC18Nm vector. FIG. 2G illustrates pAC-crtM$_{F26A,W38A,F233S}$, which was produced by inserting lacPO-crtM$_{F26A,W38A,F233S}$ into the BamHI site of a pACmod vector. FIG. 2H illustrates pAC-crtM$_{F26A,W38A,F233S}$-idi, which was produced by inserting lacPO-idi upstream of the ClaI site of pAC-crtM$_{F26A,W38A,F233S}$.

FIG. 4A illustrates an overview of procedures of a screening experiment system, and FIG. 4B illustrates a screening principle.

FIGS. 6A-6I show the results of HPLC analysis of carotenoids produced by culturing E. coli that was co-transformed with pAC-fds$_{Y81A,V157A}$-crtM$_{F26A,W38A,F233S}$ and various plasmids (Examples 3 to 6). FIGS. 6A to 6H show chromatograms obtained from HPLC analysis when introducing various plasmids. FIG. 6I shows the absorption spectra of compounds forming respective peaks. In FIG. 6I, the rightmost numerical values correspond to the numbers of the peaks in the chromatograms, and the three-digit numerical values are values for maximum absorption wavelengths.

FIGS. 8A and 8B show the absorption spectra of acetone extracts from $E.$ $coli$ transformed with various genes, and FIG. 8C is photographs showing the actual colors of cell pellets (upper row) and acetone extracts (lower row) in a similar case. CrtI* means that a crtI variant derived from CrtI-m2 was introduced into $E.$ $coli$.

FIG. 11A illustrates pUC-pBAD-$CrtI_{N304P}$-CrtY-$CrtW_{BD}$-$CrtZ_{BD}$. FIG. 11B illustrates pUC-pBAD-CrtI-m2-CrtY-$CrtW_{BD}$. FIG. 11C illustrates pUC-pBAD-CrtI-m2-CrtY-$CrtZ_{BD}$. FIG. 11D illustrates pAC-$crtM_{F26A,W38A,F233S}$-$fds_{Y81A,V157A}$-idi.

FIG. 15A illustrates pUC-pBAD-$CrtI_{N304P}$-CrtY-CrtG-$CrtZ_{BD}$. FIG. 15B illustrates pUC-pBAD-$CrtI_{N304P}$-CrtY-CrtG-$CrtW_{BD}$-$CrtZ_{BD}$. FIG. 15C illustrates pUC-pBAD-$CrtI_{N304P}$-CrtY-CrtX-$CrtZ_{BD}$. FIG. 15D illustrates pUC-pBAD-$CrtI_{N304P}$-CrtY-CrtX-$CrtW_{BD}$-$CrtZ_{BD}$.

In FIG. 20, (b) shows that C50-caloxanthin (peak 3) and C50-nostoxanthin (peak 2) were produced by the additional expression of CrtG, and (c) shows that C50-zeaxanthin-β-D-diglucoside (peak 5) was produced by the additional expression of CrtX.

FIG. 21A illustrates pAC-hexPS. FIG. 21B illustrates pAC-$FDS_{I78G,Y81A}$-idi. FIG. 21C illustrates pUC-$CrtM_{F26A,W38A,F233S}$.

DETAILED DESCRIPTION OF THE INVENTION

Figure 1:
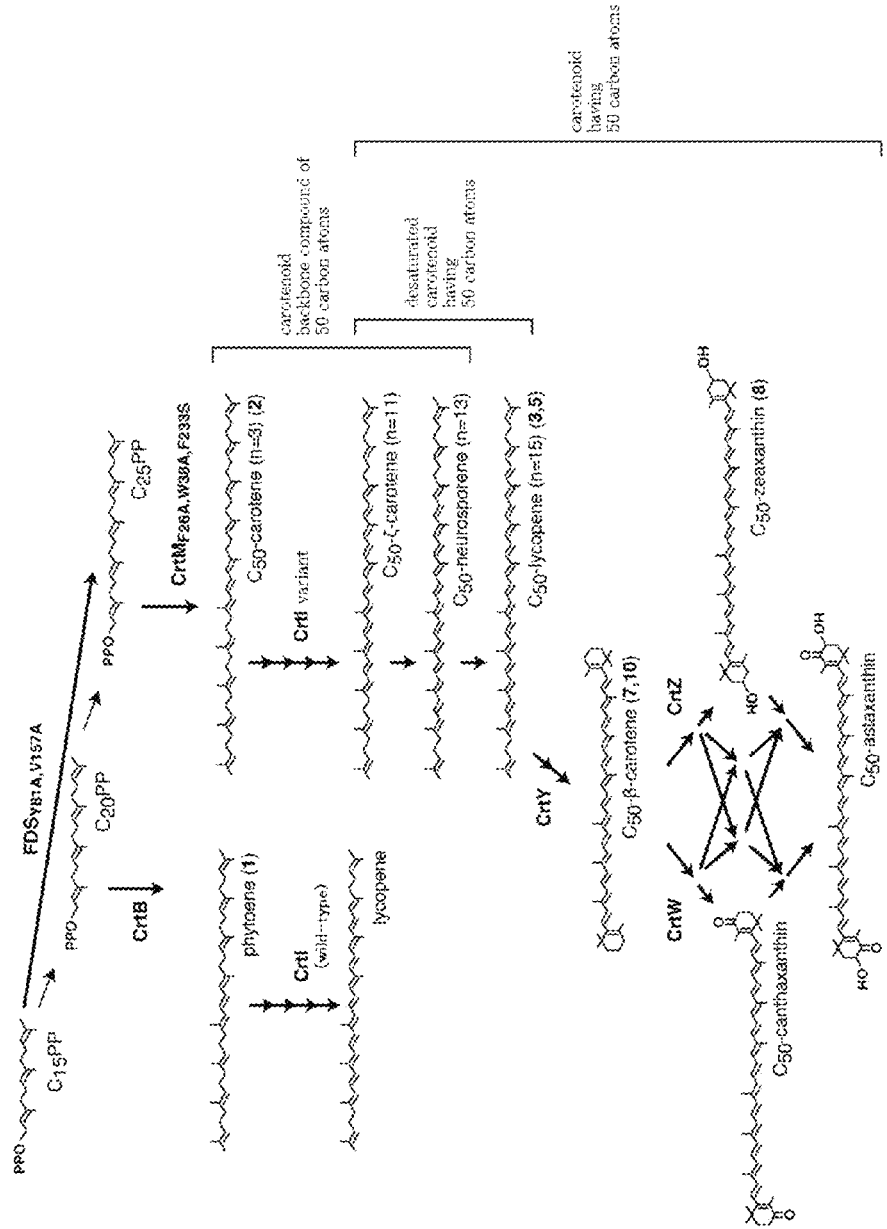
FIG. 1 illustrates functions of enzymes involved in carotenoid biosynthesis, and carotenoid biosynthetic pathways. Abbreviations for the enzymes that catalyze the corresponding reactions are given beside respective arrows. Further, numerals given in parentheses following compound names correspond to numbers of peaks of HPLC analysis in FIGS. 6A-6I.

First, carotenoid biosynthetic pathways are described (see FIG. 1). Carotenoids are biosynthesized from mevalonic acid or pyruvic acid in nature. First, isopentenyl diphosphate (hereinafter referred to as "IPP") and dimethylallyl diphosphate (hereinafter referred to as "DMAPP"), a compound obtained by the isomerization of IPP, are synthesized through a mevalonate pathway or a non-mevalonate pathway (MEP pathway in FIG. 1). Next, geranyl diphosphate (hereinafter referred to as "$C_{10}PP$") is synthesized by condensation of IPP and DMAPP. Then, farnesyl diphosphate (hereinafter referred to as "$C_{15}PP$") and geranylgeranyl diphosphate (hereinafter referred to as "$C_{20}PP$") are synthesized by the sequential addition of two molecules of IPP. $C_{15}PP$ is synthesized by a farnesyl diphosphate synthase, and $C_{20}PP$ is synthesized by a geranylgeranyl diphosphate synthase.

In a pathway for synthesizing a carotenoid having 40 carbon atoms, phytoene is synthesized by condensation of two molecules of $C_{20}PP$ with a phytoene synthase (CrtB), and serves as a precursor for a carotenoid (carotenoid backbone compound).

Phytofluene, ζ-carotene, neurosporene, lycopene, tetradehydrolycopene, and the like are synthesized by sequential desaturation of phytoene. Various carotenoids such as α-carotene, β-carotene, γ-carotene, δ-carotene, ε-carotene, lutein, zeaxanthin, canthaxanthin, fucoxanthin, astaxanthin, antheraxanthin, and violaxanthin are synthesized by modification of the ends of lycopene through cyclization or oxidation. It should be noted that carotenoids constructed only of carbon and hydrogen are classified as carotenes, while carotenoids containing an oxygen element in addition to carbon and hydrogen are classified as xanthophylls.

The present invention enables production of a carotenoid having 50 carbon atoms by alteration of biosynthetic pathways for carotenoids present in nature, and is directed to a production method for a carotenoid having 50 carbon atoms, wherein the production method comprises: culturing, in a medium, a cell transformed with a mutant phytoene desaturase gene; and obtaining a carotenoid having 50 carbon atoms from a culture after the culturing. It should be noted that, in this description, "50 carbon atoms" is sometimes simply referred to as "$C_{50}$", and the same applies to, for example, 35, 40, 45, 55, and 60 carbon atoms.

In this description, the "carotenoid having 50 carbon atoms" is distinguished from a "carotenoid backbone compound of 50 carbon atoms" to be desaturated by a mutant phytoene desaturase, and refers to a compound whose number of double bonds has been increased by one or more by the desaturation of the carotenoid backbone compound of 50 carbon atoms. The carotenoid having 50 carbon atoms may undergo any modification, and also includes, for example, one having a β ring or an s ring at its ends, and one having a functional group containing an element other than carbon and hydrogen, such as a hydroxyl group or a keto group. Further, the carotenoid having 50 carbon atoms may be any carotenoid as long as the number of carbon atoms derived from a backbone compound is 50, and also includes, for example, one in which the total number of carbon atoms is 50 or more as a result of the addition of a functional group containing carbon, such as a methyl group or an acetyl group, by modification.

The "carotenoid backbone compound of 50 carbon atoms" is a precursor for the carotenoid having 50 carbon atoms, which may be desaturated by a mutant phytoene desaturase. Specific examples of the carotenoid backbone compound of 50 carbon atoms include: $C_{50}$-carotene (n=3) (16,16'-diisopentenylphytoene); and compounds in which the number of conjugated double bonds in $C_{50}$-carotene (n=3) is increased by 1 to 5. Specific examples of the compounds in which the number of the double bonds in $C_{50}$-carotene (n=3) is increased by 1 to 5 include: $C_{50}$-carotene (n=5), which is obtained by increasing the number of the double bonds by 1; $C_{50}$-carotene (n=7), which is obtained by increasing the number of the double bonds by 2; and $C_{50}$-ζ-carotene (n=11) and $C_{50}$-neurosporene (n=13) in FIG. 1. It should be noted that, in this description, "n", which is described, for example, following common names for compounds, represents the number of conjugated double bonds.

In this description, the carotenoid backbone compound of 50 carbon atoms that has been desaturated by a mutant phytoene desaturase but has not undergone any modification afterwards is referred to as "desaturated carotenoid having 50 carbon atoms." The desaturated carotenoid having 50 carbon atoms is a linear compound that does not have any functional group except for that derived from a backbone compound. The desaturated carotenoid having 50 carbon atoms is encompassed by the carotenoid having 50 carbon atoms. Specific examples of the desaturated carotenoid having 50 carbon atoms include compounds in which the number of double bonds in $C_{50}$-carotene (n=3) is increased by 1 to 6, and do not include $C_{50}$-carotene (n=3) itself. It should be noted that the compound in which the number of the double bonds in $C_{50}$-carotene (n=3) is increased by 6 is $C_{50}$-lycopene (n=15).

Further, in this description, the term "compound having a carotenoid backbone of 50 carbon atoms" is used in some cases as a concept including all of the carotenoid having 50 carbon atoms, the carotenoid backbone compound of 50 carbon atoms, the desaturated carotenoid having 50 carbon atoms, and the like.

The mutant phytoene desaturase that catalyzes a reaction for desaturating the carotenoid backbone compound of 50 carbon atoms is obtained by inducing a mutation in a wild-type phytoene desaturase (CrtI). The phytoene desaturase (CrtI) is an enzyme that desaturates phytoene having 40 carbon atoms. In nature, CrtI catalyzes a synthesis reaction of lycopene that contains 11 conjugated double bonds, by desaturating phytoene that contains 3 conjugated double bonds to sequentially introduce double bonds. The mutant phytoene desaturase in the present invention has an enhanced activity to desaturate the $C_{50}$ carotenoid backbone compound as compared to the wild-type phytoene desaturase by virtue of the introduction of a mutation.

The mutant phytoene desaturase in the present invention may be derived from any organisms including plants, bacteria, and the like as long as the mutant phytoene desaturase has an enhanced activity to desaturate the $C_{50}$ carotenoid backbone compound by virtue of a mutation. The mutant phytoene desaturase is preferably derived from microorganisms, more preferably derived from bacteria belonging to the genus *Pantoea* (formerly named the genus *Erwinia*), still more preferably derived from *Pantoea ananatis* (formerly named *Erwinia uredovora*). The amino acid sequence of the wild-type phytoene desaturase (CrtI) derived from *Pantoea ananatis* is set forth in SEQ ID NO: 1 of the sequence listing.

In the present invention, a mutant phytoene desaturase gene (crtI*) encodes the mutant phytoene desaturase. A mutation in the mutant phytoene desaturase gene may be any mutation as long as it achieves the object of the present invention. The mutation preferably causes a substitution of an amino acid corresponding to at least one amino acid selected from asparagine at position 304, phenylalanine at position 339, isoleucine at position 338, aspartic acid at position 395, and isoleucine at position 228 in the amino acid sequence set forth in SEQ ID NO: 1, more preferably causes at least a substitution of an amino acid corresponding to asparagine at position 304 in SEQ ID NO: 1 by proline or serine, still more preferably causes at least a substitution of an amino acid corresponding to asparagine at position 304 in SEQ ID NO: 1 by proline. Herein, the "amino acid corresponding to an amino acid at position X in SEQ ID NO: 1" defines that an amino acid as a target of the mutation is at position X counting from the N-terminus in SEQ ID NO: 1, but encompasses that the position X is expressed with a different numerical value in a phytoene desaturase having an amino acid sequence different from the amino acid sequence set forth in SEQ ID NO: 1.

The mutant phytoene desaturase gene is specifically exemplified by a phytoene desaturase gene derived from *Pantoea ananatis* (nucleotide sequence set forth in SEQ ID NO: 2 of the sequence listing), the nucleotide sequence having introduced therein a mutation causing a desired amino acid substitution. The mutant phytoene desaturase gene is exemplified by a gene having a nucleotide sequence of SEQ ID NO: 3 in which adenine (A) at position 911 is substituted by guanine (G) in the nucleotide sequence of SEQ ID NO: 2. The substitution of the nucleotide at position 911 causes a substitution of asparagine at position 304 in the amino acid sequence of SEQ ID NO: 1 by serine. It should be noted that SEQ ID NO: 2 has introduced therein non-synonymous mutations G1131A and A1476T. Further, the mutant phytoene desaturase gene is exemplified by a gene having a nucleotide sequence in which the nucleotide sequence AAC at positions 910 to 912 in the nucleotide sequence of SEQ ID NO: 2 is substituted by CCT, CCC, CCA, or CCG, more preferably CCT (nucleotide sequence set forth in SEQ ID NO: 28 of the sequence listing). The substitution of such bases causes a substitution of asparagine at position 304 in the amino acid sequence of SEQ ID NO: 1 by proline (amino acid sequence set forth in SEQ ID NO: 27 of the sequence listing). It should be noted that SEQ ID NO: 28 has introduced therein non-synonymous mutations G1131A and A1476T.

The nucleotide sequence of the mutant phytoene desaturase gene may be determined by producing a mutant gene library and screening a gene encoding an enzyme that has a function of interest from the library. The screening may be performed by, for example, a method described in Examples. Once the nucleotide sequence is determined, the mutant phytoene desaturase gene may be obtained by, for example, chemical synthesis, PCR using a cloned probe as a template, or a site-directed mutagenesis method.

The present invention includes the step of culturing, in a medium, a cell to be transformed with a mutant phytoene desaturase gene. The cell may be one originally harboring any other carotenoid biosynthetic gene, or may be one transformed with any other carotenoid biosynthetic gene. The other carotenoid biosynthetic gene is involved in a reaction upstream or downstream of a desaturating reaction for the $C_{50}$ carotenoid backbone compound. The upstream reaction corresponds to a pathway for supplying the $C_{50}$ carotenoid backbone compound, and the downstream reaction corresponds to a pathway for further modifying the $C_{50}$ desaturated carotenoid.

The pathway for supplying the $C_{50}$ carotenoid backbone compound is described. IPP, DMAPP, $C_{10}PP$, $C_{15}PP$, and $C_{20}PP$ can be originally synthesized in many cells, in particular, all microorganisms. It is preferred that the cell in the present invention can synthesize geranylfarnesyl diphosphate (hereinafter sometimes referred to as "$C_{25}PP$") from $C_{15}PP$ and/or $C_{20}PP$, and can synthesize the $C_{50}$ carotenoid backbone compound via the condensation of two molecules of $C_{25}PP$. It is more preferred that the cell in the present invention be transformed with at least one of a gene encoding an enzyme that synthesizes $C_{25}PP$ from $C_{15}PP$ and/or $C_{20}PP$ or a gene encoding an enzyme that synthesizes the $C_{50}$ carotenoid backbone compound via the condensation of two molecules of $C_{25}PP$.

The gene encoding the enzyme that synthesizes $C_{25}PP$ from $C_{15}PP$ and/or $C_{20}22$ may be any gene having a function of interest. Such gene is exemplified by a mutant gene of a farnesyl diphosphate synthase (FDS) derived from *Geobacillus stearothermophillus*, a moderate thermophilic bacterium belonging to the genus *Geobacillus* (Ohnuma, S. et al., J Biol Chem 271, 30748-30754 (1996), JP 2010-258989). The mutant gene is exemplified by a gene encoding a double mutant of FDS ($FDS_{Y81A, V157A}$) in which tyrosine at position 81 is substituted by alanine (Y81A) and valine at position 157 is substituted by alanine (V157A) ($fds_{Y81A, V157A}$: SEQ ID NO: 4 of the sequence listing).

The gene encoding the enzyme that synthesizes the $C_{50}$ carotenoid backbone compound via the condensation of two molecules of $C_{25}PP$ may be any gene having a function of interest. Such gene is exemplified by a mutant gene of a diapophytoene synthase (CrtM) derived from *Staphylococcus aureus*, which synthesizes a $C_{30}$ carotenoid backbone compound via the condensation of two molecules of $C_{15}PP$. The mutant gene is exemplified by a gene encoding a triple mutant of CrtM ($CrtM_{F26A, W38A, F233S}$) in which phenylalanine at position 26 and tryptophan at position 38 are substituted by alanine (F26A and W38A) and phenylalanine at position 233 is substituted by serine (F233S) $CrtM_{F26A, W38A, F233S}$: SEQ ID NO: 5 of the sequence listing). It has been found that $CrtM_{F26A, W38A, F233S}$ synthesizes the $C_{50}$ carotenoid backbone compound in an extremely efficient manner.

The cell of the present invention is preferably transformed with both of the gene encoding the enzyme that synthesizes $C_{25}PP$ from $C_{15}PP$ and/or $C_{20}PP$ and the gene encoding the enzyme that synthesizes the $C_{50}$ carotenoid backbone compound from two molecules of $C_{25}PP$ because the cell can produce the $C_{50}$ carotenoid backbone compound with high efficiency. In addition, the cell of the present invention may be transformed with a gene (idi) encoding an enzyme that isomerizes IPP into DMAPP (e.g., an isopentenyl diphosphate isomerase (Idi)) in addition to the above-mentioned genes. When the cell is transformed with the gene encoding the enzyme that isomerizes IPP into DMAPP, the production amount of the $C_{50}$ carotenoid backbone compound and the specificity can be further improved.

The pathway for further modifying the $C_{50}$ desaturated carotenoid is described. The $C_{50}$ desaturated carotenoid is considered to correspond to lycopene or tetradehydrolycopene in nature, and it is predicted that the $C_{50}$ desaturated carotenoid may be modified by various enzymes involved in the modification of lycopene. The cell in the present invention may contain a gene encoding an enzyme that cyclizes the ends of the $C_{50}$ desaturated carotenoid and/or a gene encoding an enzyme that oxidizes the $C_{50}$ desaturated carotenoid by oxygenation. In addition, when the cell in the present invention has the gene encoding the enzyme that cyclizes the ends of the $C_{50}$ desaturated carotenoid (in particular, β-cyclization), the cell may be transformed with a gene encoding an enzyme that hydroxylates a cyclic moiety (in particular, a β-ring) and/or a gene encoding an enzyme that ketolates a cyclic moiety (in particular, a β-ring). It should be noted that the β-ring has the same meaning as a β-ionone ring.

The gene encoding the enzyme that cyclizes the ends of the $C_{50}$ desaturated carotenoid may be any gene having a function of interest. Such gene is exemplified by a gene (crtY) encoding a lycopene cyclase (CrtY) derived from *Pantoea ananatis*, which synthesizes β-carotene from lycopene (Misawa N. et al., J Bacteriol 172, 6704-6712 (1990)).

In a carotenoid having β-cyclized ends, a gene encoding an enzyme that hydroxylates the β-ring and/or a gene encoding an enzyme that ketolates the β-ring may be any gene having a function of interest. Such gene is exemplified by a β-ionone ring-3-hydroxylase (CrtZ) gene (crtZ) or β-ionone ring-4-ketolase (β-ionone ring-4-oxygenase) (CrtW) gene (crtW) derived from a marine bacterium *Paracoccus* sp. strain N81106 (formerly named *Agrobacterium aurantiacum*) or derived from a marine bacterium *Brevundimonas* sp. strain SD-212 (Misawa N. et al., J Bacterial 177, 6575-6584 (1995); Nishida, Y. et al., Appl Environ Microbiol 71, 4286-4296 (2005)). A nucleotide sequence in which crtZ and crtW derived from *Paracoccus* sp. strain N81106 and crtY described above are combined is set forth in SEQ ID NO: 6. A β-ionone ring-3-hydroxylase catalyzes a reaction for hydroxylating carbon at the 3-position of a β-ring, and a β-ionone ring-4-ketolase catalyzes a reaction for oxygenating carbon at the 4-position of a β-ring to form a carbonyl group (keto group).

The gene encoding the enzyme that oxidizes the $C_{50}$ desaturated carotenoid may be any gene having a function of interest. Such gene is exemplified by a spheroidene monooxygenase (CrtA) gene (crtA) derived from *Rhodobacter sphearoides* (SEQ ID NO: 7). A spheroidene monooxygenase is an enzyme that catalyzes an oxidation reaction for converting spheroidene into spheroidenone by inserting an oxygen atom.

The cell of the present invention may be transformed with genes encoding various enzymes involved in the pathway for modifying the $C_{50}$ desaturated carotenoid other than those described above, depending on the kind of a carotenoid to be produced. For example, when the cell is transformed with a β-ionone ring-2-hydroxylase (CrtG) gene (expressed as "CrtV" in WO 2005/049643 A1) derived from *Brevundimonas* sp. strain SD-212 (Nishida, Y. et al, Appl Environ Microbiol 71, 4286-4296, 2005), a $C_{50}$ carotenoid having a β-ring hydroxylated at the 2-position and the 2'-position, the organic synthesis of which has been considered to be difficult, can also be produced. Further, when the cell is transformed with a zeaxanthin glucosyl transferase (crtX) gene derived from *Pantoea ananatis* (Misawa N, J Bacteriol 172, 6704-6712, 1990), a $C_{50}$ carotenoid in which hydroxyl groups at the 3-position and 3'-position of a β-ring are glycosidized can also be produced.

A cell capable of producing a $C_{50}$ carotenoid in the present invention may be produced by selecting an appropriate expression vector and employing a known foreign gene introduction and expression method (e.g., Sambrook, J., Russel, D. W., Molecular Cloning A Laboratory Manual, 3rd Edition, CSHL Press, 2001). The cell is obtained by: preparing a gene to be introduced into the cell by transformation by using a conventional method such as a PCR method; incorporating the gene into an expression vector suitable for a host by using a conventional method; selecting a vector of interest; and transforming a host cell with the vector by using a conventional method. When transforming a cell with two or more kinds of genes, the cell may be transformed with the plurality of genes incorporated into the same expression vector, or may be cotransformed with the plurality of genes incorporated into different expression vectors.

The cell serving as the host is not limited, but microorganisms such as *E. coli*, *Bacillus subtilis*, and yeast are preferred in view of shortening of a culturing time and ease of cloning. In particular, *E. coli* and yeast are preferred. Suitable examples of the *E. coli* include: cloning strains such as *Escherichia coli* XL1-Blue (hereinafter simply referred to as "*E. coli* XL1-Blue"); expression strains such as HB101 and BL21; and gene knockout strains in which the synthesis amount of a terpene precursor is large, such as JW1750 ΔgdhA (glutamate dehydrogenase-deficient) and JW0110 ΔaceE (pyruvate dehydrogenase-deficient) (Baba, T. et al.; Mol Syst Biol 2, 2006 0008 (2006)). Suitable examples of the yeast include standard budding yeast INVSc1 (invitrogen) and YPH499 (stratagene).

The expression vector into which the gene is applied is not particularly limited and may be a vector to be generally used. For example, when the host is *E. coli*, there are given ones derived from pUC18, pACYC184, and the like. When the host is *Bacillus subtilis*, there are given pUB110, pE194, pC194, pHY300PLK DNA, and the like. And when the host is yeast, there are given pRS303, YEp213, TOp2609, and the like.

Whether or not a gene of interest is introduced into the host cell may be confirmed by a conventional method such as a PCR method, a Southern hybridization method, or a northern hybridization method.

The production method for a $C_{50}$ carotenoid of the present invention includes the step of culturing, in a medium, the cells as the transformants obtained as described above. The medium may be any medium containing a substance that may serve as a supply source for the $C_{50}$ carotenoid backbone compound, and may be any medium containing an ingredient to be generally used for cell culturing. For cells in which the $C_{50}$ carotenoid backbone compound is synthesized by the metabolism of IPP and DMAPP, the medium may be any medium containing a carbon source that may serve as a supply source for IPP and DMAPP. Examples of such carbon source include a variety of sugars such as glucose.

A temperature at the time of the culturing is not particularly limited but is set to preferably 18 to 30° C., more preferably 20 to 30° C.

Culture period is also not particularly limited but the culturing is performed for preferably 12 to 72 hours, more preferably 24 to 48 hours after the expression of the gene introduced by the transformation.

The $C_{50}$ carotenoid can be collected from the culture after the culturing in accordance with a method to be generally employed for obtaining a product such as a carotenoid from cells of microorganisms or the like. It may also be possible to separate only the cells from the culture and obtain the carotenoid from the cells.

It should be noted that the present invention is also directed to a mutant phytoene desaturase gene, a mutant phytoene desaturase encoded by the mutant phytoene desaturase gene, and a cell capable of desaturating a $C_{50}$ carotenoid backbone compound to produce a $C_{50}$ carotenoid, which is transformed with the mutant phytoene desaturase gene.

Further, the present invention can be utilized in the highly efficient synthesis of a desaturated $C_{55}$ carotenoid, a desaturated $C_{60}$ carotenoid, or the like. For example, the desaturated $C_{55}$ carotenoid as well as the C50 carotenoid can be produced with high efficiency by utilizing the present invention using a double mutant of a farnesyl diphosphate synthase (FDS) ($FDS_{I78G,Y81A}$) in which isoleucine at position 78 is substituted by glycine (I78G) and tyrosine at position 81 is substituted by alanine (Y81A) in FDS (Ohnuma S et al., J Biol Chem 273, 26705-26713, 1998). Further, the desaturated $C_{60}$ carotenoid can be produced with high efficiency by utilizing the present invention using a $C_{30}PP$ synthase (HexPS) derived from *Micrococcus luteus* (Shimizu N et al, J Bacteriol 180, 1578-1581, 1998), that is, by co-expressing $FDS_{I78G,Y81A}$ or HexPS with the CrtM variant.

EXAMPLES

Hereinafter, the present invention is specifically described by way of Examples. However, the present invention is by no means limited thereto.

(Reference Example 1) Synthesis of $C_{50}$ Carotenoid Backbone Compound (1) Supply of $C_{50}$ Carotenoid Raw Material, $C_{25}PP$ A mutant gene $fds_{Y81A, V157A}$ was used in order to efficiently synthesize $C_{25}PP$ in *E. coli*. $fds_{Y81A, V157A}$ is a mutant of a farnesyl diphosphate synthase (FDS) derived from *Geobacillus stearothermophillus*. The mutation Y81A is derived from Ohnuma, S. et al., J Biol Chem 271, 30748-30754 (1996). Further, the inventors of the present invention produced $fds_{Y81A,V157A}$ encoding a mutant enzyme having further shifted size specificity for a substrate by further introducing a mutation into a mutant gene $fds_{Y81A}$ through the use of the screening method for a terpene synthase gene disclosed in JP 2010-258989.

(2) Synthesis of $C_{50}$ Carotenoid Backbone Compound

A mutant gene $crtM_{F26A,W38A,233S}$ was used for the synthesis of a $C_{50}$ carotenoid backbone compound (16,16'-diisopentenylphytoene) via the condensation of two molecules of $C_{25}PP$. A diapophytoene synthase (CrtM) derived from *Staphylococcus aureus* is originally an enzyme that synthesizes a $C_{30}$ backbone carotenoid via the condensation of two molecules of $C_{15}PP$. The inventors of the present invention introduced a mutation into a crtM gene in order to produce an enzyme having improved size selectivity for a substrate (Umeno et al., J Bacteriol 184, 6690-6699 (2002), Umeno et al., Nucleic Acids Res 31, e91 (2003)). It was found that a $C_{50}$ carotenoid backbone compound was synthesized in a trace amount by feeding $C_{25}PP$ to a double mutant of CrtM having mutations F26A and W38A (Non Patent Literature 7).

The inventors also found that a triple mutant of CrtM having introduced therein mutations F26A, W38A, and F233S synthesized a $C_{50}$ carotenoid backbone compound from two molecules of $C_{25}PP$ in an extremely efficient manner, and synthesized a $C_{60}$ carotenoid backbone compound, though in a trace amount, when $C_{30}PP$ was fed (Maiko Furubayashi, Mayu Ikezumi, Kyoichi Saito, Daisuke Umeno. Activity evolution of unnatural carotenoid synthetic pathways, Annual Meeting of the Kanto Branch of the Japan Society for Bioscience, Biotechnology, and Agrochemistry, 2010, Oct. 9, 2010: Daisuke Umeno, Maiko Furubayashi, Mayu Ikezumi, Akinori Katabami, Ling Li, Jun Kajiwara. Creation and development of unnatural biosynthetic pathways, The Third Annual Meeting of the Japanese Society for Cell Synthesis Research, Institute of Industrial Science, the University of Tokyo, Nov. 12, 2010: Furubayashi M, Saito K, Umeno D, In-laboratory genetic drift of carotenoid synthase and its evolution of size specificity. The international chemical congress of Pacific basin societies, Hawaii, USA, Dec. 17, 2010: Maiko Furubayashi, Mayu Ikezumi, Kyoichi Saito, Daisuke Umeno. Selective synthesis of unnatural carotenoid by combinatorial expression of enzyme mutant, Annual Meeting of the Japan Society for Bioscience, Biotechnology, and Agrochemistry, 2011, March 2011). It was found that $C_{50}$-carotene (n=3), a $C_{50}$ carotenoid backbone compound, was efficiently (about 61%) produced by co-expressing $fds_{Y81A, V157A}$ for supplying $C_{25}PP$ and $crtM_{F26A,W38A,F233S}$ in *E. coli* XL1-Blue.

Figure 2A:
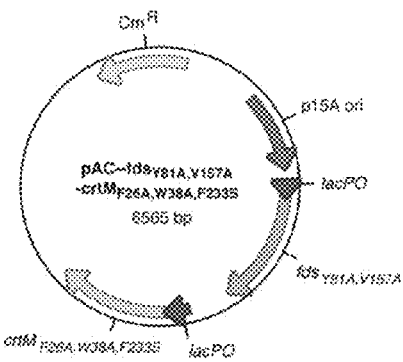
FIGS. 2A-2H illustrate plasmid maps used in Examples 1 to 6 and Reference Examples 1 and 2.
Figure 2B:
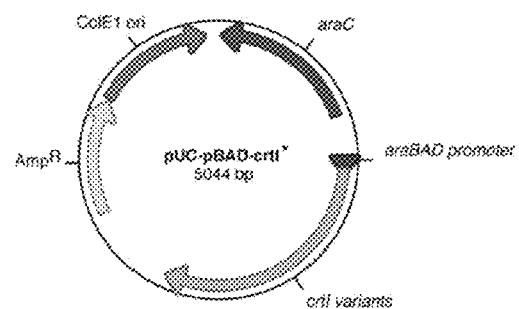
Figure 2C:
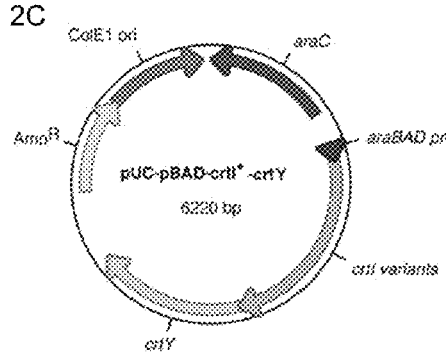
Figure 2D:
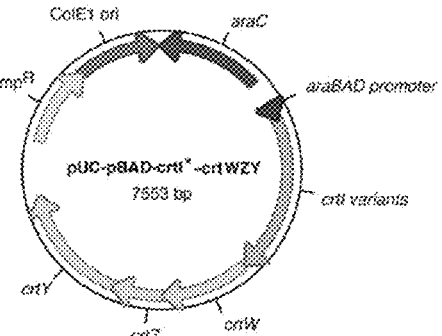
Figure 2E:
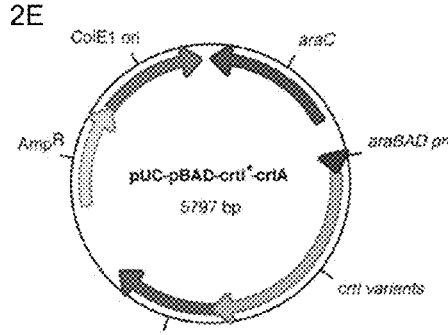
Figure 2F:
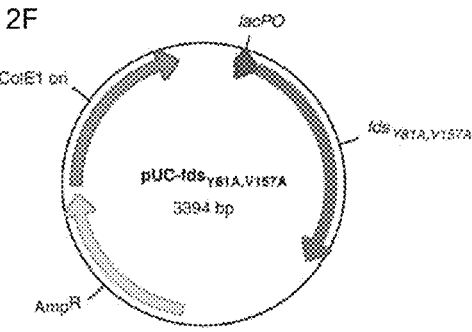
Figure 2G:
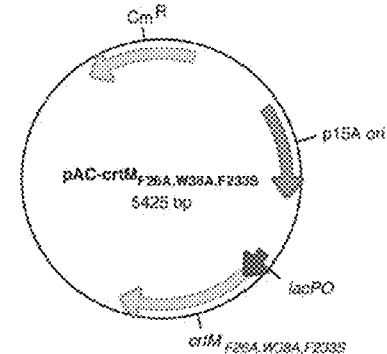

(3) It should be noted that the transformation of *E. coli* XL1-Blue with $fds_{Y81A, V157A}$ and $crtM_{F26A,W38A,F233S}$ was performed by producing plasmids pAC-$crtM_{F26A,W38A,F233S}$ (FIG. 2G: SEQ ID NO: 8) and pUC-$fds_{Y81A,V157A}$ (FIG. 2F: SEQ ID NO: 9) in accordance with a conventional method.

pAC-$crtM_{F26A,W38A,F233S}$ was produced by inserting lac promoter/operator (lacPO)-$crtM_{F26A,W38A,F233S}$ into the BamHI site of a pACmod vector (Claudia Schmidt-Dannert et al., Nat. Biotechnol., 18: 750-753 (2000)).

pUC-$fds_{Y81A,V157A}$ was produced by inserting an $fds_{Y81A,V157A}$ gene downstream of lacPO of a pUC18 Nm vector (Umeno D. et al, J Bacteriol 184, 6690-6699 (2002)).

The transformed *E. coli* was cultured in accordance with the technique disclosed in Non Patent Literature 7.

The analysis of the produced carotenoid was performed by HPLC also in accordance with the method disclosed in Non Patent Literature 7.

(Example 1) Improved Synthesis of $C_{50}$ Carotenoid Backbone Compound

Figure 2H:
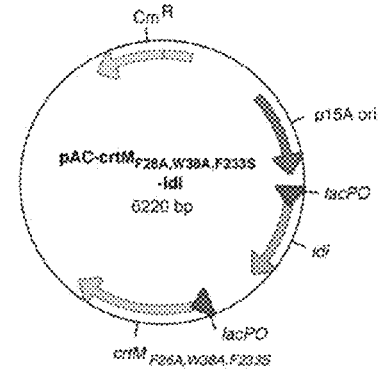

In addition to $fds_{Y81A,V157A}$ and $CrtM_{F26A,W38A,F233S}$, a gene (derived from *E. coli* genome) encoding an isopentenyl diphosphate isomerase (Idi) was expressed in *E. coli* XL1-Blue, and the *E. coli* was cultured. The transformation of *E. coli* XL1-Blue with $fds_{Y81A, V157A}$ and $crtM_{F26A,W38A,F233S}$ was performed by producing plasmids pAC-$crtM_{F26A,W38A,F233S}$-idi (FIG. 2H: SEQ ID NO: 10) and pUC-$fds_{Y81A,V157A}$ (FIG. 2F: SEQ ID NO: 9) in accordance with a conventional method. pAC-$crt_{MF26A,W38A,F233S}$-idi was produced by inserting lacPO-idi upstream of the ClaI site of pAC-$crt_{MF26A,W38A,F233S}$. pUC-$fds_{Y81A,V157A}$ was produced in the same manner as in Reference Example 1. The culturing of the transformed *E. coli* and the analysis of the produced carotenoid were performed in the same manner as in Reference Example 1.

Figure 3:
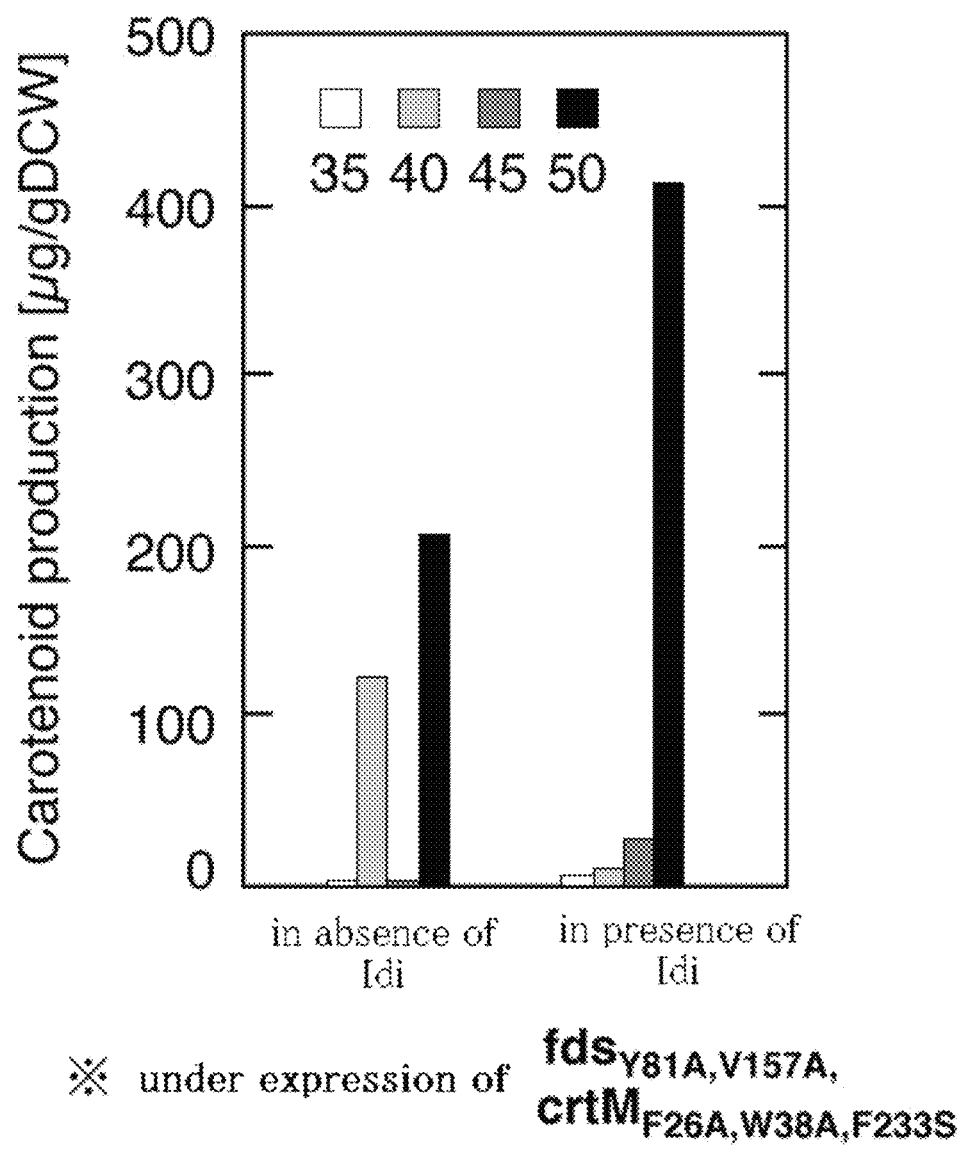
FIG. 3 shows the synthesis amount of a $C_{50}$ carotenoid backbone compound in the case where Idi is co-expressed in a metabolic pathway constructed with FDS$_{Y81A, V157A}$ and CrtM$_{F26A, W38A, F233S}$ Example 1). "Absence of idi" and "Presence of idi" represent the synthesis amounts of a compound having a $C_{35}$ carotenoid backbone (35), a compound having a $C_{40}$ carotenoid backbone (40), a compound having a $C_{45}$ carotenoid backbone (45), and a compound having a $C_{50}$ carotenoid backbone (50) obtained by subjecting acetone extracts from E. coli transformed with various genes to HPLC analysis. Specifically, in FIG. 3, "35" represents 4-apophytoene, "40" represents phytoene, "45" represents 16-isopentenylphytoene, and "50" represents $C_{50}$-carotene (n=3).

FIG. 3 shows the results. The production amount of $C_{50}$-carotene (n=3), a $C_{50}$ carotenoid backbone compound, was increased in the case of introducing Idi as compared to the case of not introducing Idi. Further, phytoene, a $C_{40}$ carotenoid backbone compound, was synthesized in a large amount in the case of not introducing Idi, whereas the production amount of phytoene was decreased and the specificity of the production of $C_{50}$-carotene (n=3) was improved in the case of introducing Idi. The synthetic efficiency of $C_{50}$-carotene (n=3) was found to be improved (about 90%) in the case of introducing Idi.

(Reference Example 2) Desaturation of $C_{50}$ Carotenoid Backbone Compound by Wild-Type CrtI The inventors of the present invention found that a carotenoid having a $C_{50}$ carotenoid backbone compound was desaturated by CrtI (phytoene desaturase encoded by a gene having a nucleotide sequence of SEQ ID NO: 2 (having introduced therein non-synonymous mutations G1131A and A1476T)) (Non Patent Literature 9). However, it was found that its production amount is extremely small and only 25% of the $C_{50}$ carotenoid backbone compound was desaturated (Non Patent Literature 8).

Meanwhile, the inventors of the present invention found that the constitutive expression of wild-type CrtI using a lac promoter (lacP) or the like remarkably inhibited cell growth, and remarkably destabilized cell pigmentation. However, no clear cytotoxicity was observed in cells having a pathway to the synthesis/accumulation of the $C_{50}$ carotenoid backbone compound (e.g., the cells obtained in Reference Example 1 and Example 1).

The inventors of the present invention attempted to ligate crtI downstream of an araBAD promoter capable of reducing leaky expression (low-level expression occurring without any induction) and express the ligation product in E. coli XL1-Blue. A group of carotenoid biosynthetic genes upstream of crtI were constitutively expressed by lacP. After the density/number of the cells had reached sufficient levels, it was attempted to make pigment in the cells by inducing the expression of crtI to desaturate the $C_{50}$ carotenoid backbone compound.

The plasmid used is pUC-pBAD-crtI (having crtI introduced into the crtI variant part in FIG. 2B). The lac promoter/operator (lacPO) of a pUC18 Nm vector (Umeno D. et al, J Bacteriol 184, 6690-6699 (2002)) was removed, and an araC gene/araBAD promoter sequence derived from a pBADHisA vector (invitrogen) was inserted. crtI was inserted into the XhoI-ApaI site downstream of the promoter. crtI is a gene encoding a wild-type phytoene desaturase derived from Pantoea ananatis (Misawa N. et al., J Bacteriol 172, 6704-6712 (1990)).

The problem of the cytotoxicity was overcome in E. coli transformed with pUC-pBAD-crtI. However, the $C_{50}$ carotenoid backbone compound was desaturated with extremely low efficiency, which was almost unrecognizable.

Figure 4A:
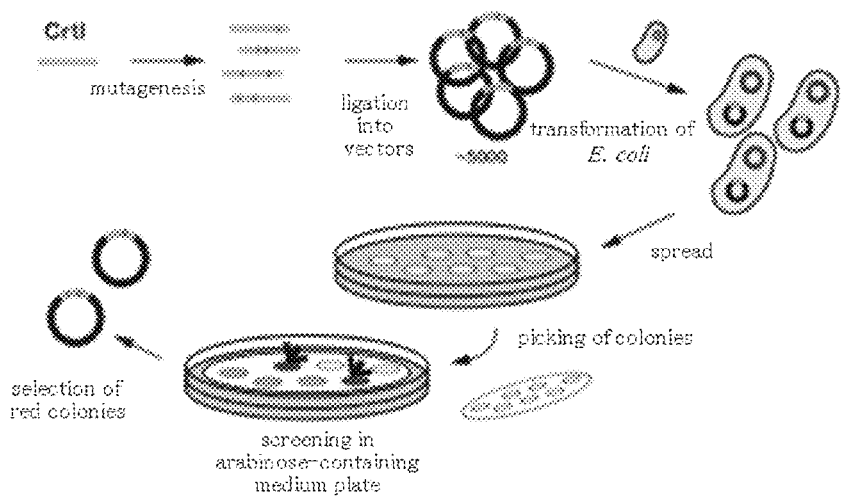
FIGS. 4A and 4B illustrate the screening of a mutant phytoene desaturase capable of efficiently desaturating a carotenoid backbone compound of 50 carbon atoms (Example 2).

(Example 2) Acquisition of crtI Variant Desaturating $C_{50}$ Carotenoid Backbone Compound Based on the evolutionary engineering of a phytoene desaturase (CrtI), it was attempted to acquire a crtI variant that desaturates more efficiently the $C_{50}$ carotenoid backbone compound. FIG. 4A illustrates an overview of procedures of this example, and FIG. 4B illustrates a screening principle.

First, a plasmid pUC-pBAD-crtI containing wild-type crtI (represented by "pUC-I" in FIG. 4B) was used as a template, and a random mutation was introduced into crtI by an error-prone PCR method using $MnCl_2$ (Cadwell et al.: PCR Methods Appl 2, 28-33 (1992)) The obtained PCR product was digested with restriction enzymes XhoI and ApaI, and ligated into the restriction enzyme sites of XhoI and ApaI downstream of an araBAD promoter in a pUC-pBAD vector. E. coli XL10-Gold (Stragatene) was transformed with the ligation product, and part thereof was spread on a Luria Bertani (LB) solid medium. The remaining transformed E. coli was added to 10 mL of an LB liquid medium and cultured at 37° C. overnight. After that, a plasmid was extracted from 2 mL of the culture and used as a "crtI variant plasmid library." Further, the number of the transformed cells (library size), which was calculated from the number of the colonies formed on the solid medium, was $10^5$ cfu/transformation.

Figure 4B:
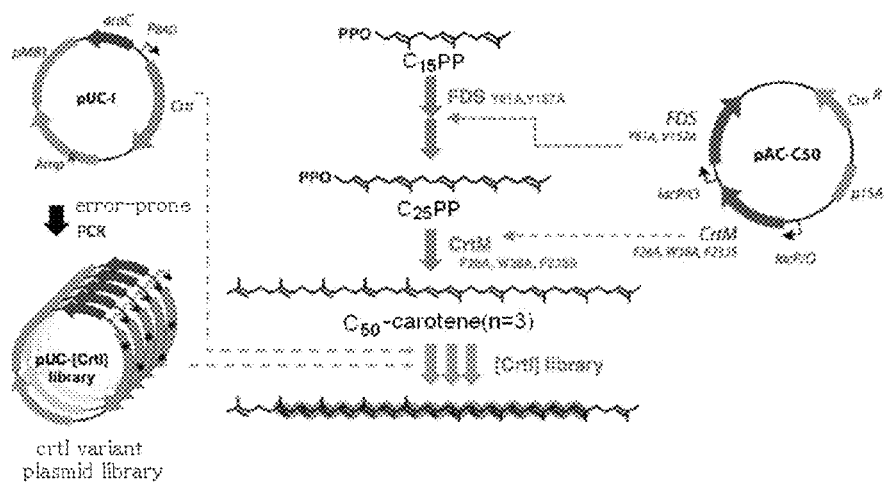

E. coli XL1-Blue harboring a plasmid pAC-crtM$_{F26A,W38A,F233S}$-fds$_{Y81A,V157A}$ (represented by "pAC-$C_{50}$" in FIG. 4B: SEQ ID NO: 11) was transformed with the thus obtained plasmid library and spread on an LB solid medium (containing 50 μg/mL carbenicillin and 30 μg/mL chloramphenicol) on which a nitrocellulose filter was mounted. The cells were cultured at 37° C. for 24 hours until the colonies were formed, and then left to stand still at room temperature for an additional 48 hours.

As a control, E. coli XL1-Blue was transformed with pUC-pBAD-crtI containing wild-type crtI. In this case, the colonies developed a flesh color. In the group of about 2,000 colonies obtained by transformation with the crtI variant plasmid library, 8 colonies developing a particularly intense reddish violet color were visually detected. The colonies were named CrtI-m1, m2, and m8, respectively. As illustrated in FIG. 4B, $C_{50}$-lycopene (n=15), a $C_{50}$ desaturated carotenoid, is a pigment developing a reddish violet color, and it is estimated that, as a result of the efficient synthesis of such compound, the colonies developed a reddish violet color.

The bacterial strain of each of the colonies was cultured in an LB liquid medium at 37° C. for 12 hours to extract a plasmid, and the nucleotide sequence of a crtI variant contained in the plasmid was analyzed by a dideoxy method. Table 1 below shows the analysis results.

TABLE 1

Analysis results of gene mutations in CrtI variants

| Sample names | Gene mutations (amino acid mutations are shown in parentheses) |
| --- | --- |
| CrtI-m1 | A195G, A594G, T1016C (F339S) |
| CrtI-m2 | A911G (N304S) |
| CrtI-m3 | None |
| CrtI-m4 | T1015C (F339L), G1183A (D395N) |
| CrtI-m5 | None |
| CrtI-m6 | A682G (I228V), A1012G (I338V) |
| CrtI-m7 | T144C, A1012G (I338V) |
| CrtI-m8 | A911G (N304S), T1017C |

It was found that CrtI-m2 and CrtI-m8 had the same mutation in which asparagine (N) at position 304 was substituted by serine (S) (N304S). Further, CrtI-m1 and CrtI-m4 each had a mutation in which phenylalanine (F) at position 339 was substituted by serine (S) or leucine (L) (F339S or F339L), and CrtI-m6 and CrtI-m7 each had a mutation in which isoleucine (I) at position 338 was substituted by valine (V) (I338V). It was estimated that the CrtI variants each had an enhanced ability to desaturate a $C_{50}$ carotenoid backbone compound by virtue of those mutations.

(Example 3) Synthesis of Desaturated $C_{50}$ Carotenoid by CrtI Variant

Of the colonies obtained in Example 2, each of CrtI-m1, m2, m4, m6, and m8, which showed enhanced pigmentation as compared to wild-type CrtI, was confirmed for its ability to desaturate a $C_{50}$ carotenoid backbone compound.

E. coli XL1-Blue harboring pAC-crtM$_{F26A,W38A,F233S}$-fds$_{Y81A,V157A}$ was transformed with each of the plasmids pUC-pBAD-CrtI-m1, m2, m4, m6, and m8. The transformant was spread on an LB agar medium on which a nitrocellulose (NC) membrane was contracted, and cultured at 37° C. for 24 hours. The plasmids pUC-pBAD-CrtI-m1, m2, m4, m6, and m8 have various mutant genes mut1, mut2, mut4, mut6, and mut8 inserted into the crtI* part in pUC-pBAD-crtI*-crtY of FIG. 2C, respectively, and the nucleotide sequence of the plasmid having inserted therein mut2 is set forth in SEQ ID NO: 12.

After the formation of the colonies, the NC membrane with the colonies was transferred onto an LB agar medium containing 0.2% arabinose, followed by incubation at room temperature. The colonies were inoculated into 2 mL of an LB medium (containing 50 μg/mL carbenicillin and 30 μg/mL chloramphenicol) and cultured at 37° C. overnight. 300 μL of the culture medium were inoculated into 30 mL of a TB medium (containing 50 μg/mL carbenicillin and 30 μg/mL chloramphenicol), followed by incubation under shaking at 30° C. and 200 rpm. After the incubation under shaking for 24 hours, 20% arabinose was added to the culture medium so as to have a final concentration of 0.2%, followed by incubation under shaking (30° C.) for an additional 48 hours.

The culture medium was measured for its $OD_{600}$, and the cells were harvested by centrifugation. The pellet obtained by harvesting the cells was washed with physiological saline, and a lipid-soluble fraction was extracted with 10 mL of acetone. A 300-μL aliquot was fractionated from the extract and measured for its absorbance spectrum with Spectra Max 384 (Molecular Device).

Figure 5A:
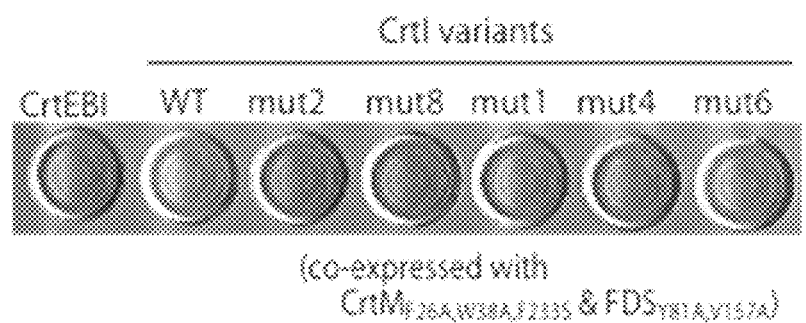
FIGS. 5A and 5B show the actual colors of acetone extracts of 6 colonies out of 8 colonies obtained by screening, and the absorption spectra of the acetone extracts (Example 3). CrtEBI, a control, shows the result of the colony of E. coli transformed with a plasmid pAC-EBI containing crtE, crtB, and crtI derived from Pantoea ananatis. WT (or CrtIwt) shows the result of the colony of E. coli transformed with wild-type crtI, while mut1, mut2, mut8, mut4, and mut6 shows the results of the colonies of CrtI-m1, CrtI-m2, CrtI-m8, CrtI-m4, and CrtI-m6, respectively. It should be noted that the transformed E. coli synthesized lycopene.
Figure 5B:
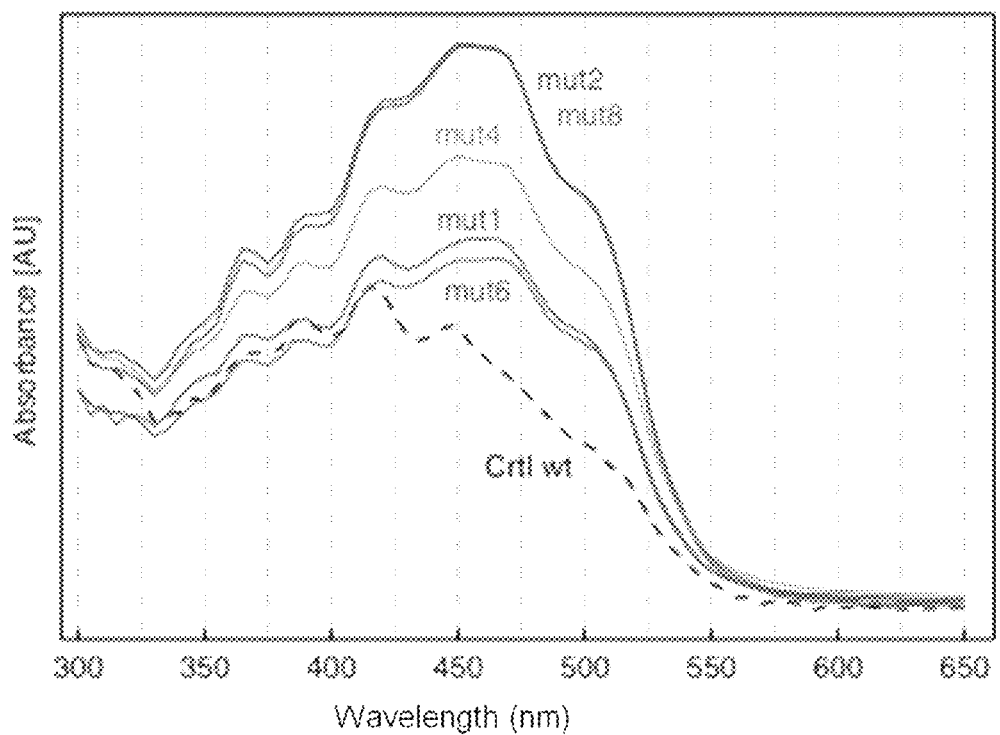

FIGS. 5A and 5B show the results. FIG. 5A is a photograph showing the actual color of each acetone extract. The absorbance of the acetone extract at around 500 to 600 nm was increased in E. coli expressing mut2, mut8, mut1, mut4, or mut6 as compared to E. coli expressing wild-type crtI (WT) (FIG. 5B). In particular, CrtI-m2 and CrtI-m8 having crtI variants with N304S exhibited intense colors and absorbances. In the case of expressing those CrtI variants, a peak (shoulder) on the rightmost side is located at about 540 nm, indicating that a six-step desaturated product (15 conjugated double bonds) is contained in a large amount. The synthesis amount of the $C_{50}$ desaturated carotenoid was the largest in the case of introducing CrtI-m2 or CrtI-m8.

Next, the carotenoid synthesized in the case of CrtI-m2 was subjected to HPLC analysis. 1 mL of hexane and 35 mL of 10% NaCl were added to the acetone extract to extract a carotenoid fraction into a hexane phase. 75% of the hexane extract were collected and dehydrated with addition of a small amount of $MgSO_4$. The hexane solvent was removed by nitrogen, and the carotenoid fraction was finally concentrated into 100 μL of hexane. Thus, a carotenoid extract was obtained. 25 μL (75%×25%=19% of the total volume, corresponding to 7.3 mL of the medium) of the resultant carotenoid extract were injected into an HPLC-photodiode-array system. HPLC analysis was performed in accordance with the conditions of Takaichi, S. Photosynth Res, 65, 93-99 (2000) (column: Waters Spherisorb™ 5.0 μm ODS2 4.6 mm×250 mm Column, eluent: acetonitrile/tetrahydrofuran/methanol (58:7:35) 2 mL/min, detector: photodiode array (190 to 800 nm)). Further, the mass spectrometry of a sample fractionated by HPLC was performed through the use of an M-2500 Hitachi double-focusing mass spectrometer (Hitachi, Ltd.) at a field desorption mode (Takaichi (1993) Org. Mass Spectrom. 28: 785-788)).

As a result, it was found that, in CrtI-m2, a compound ($C_{50}$-lycopene) obtained by the six-step desaturation of the $C_{50}$ carotenoid backbone compound was synthesized in a large amount (peak 3 in FIG. 6B). On the other hand, it was found that, in the case of transformation with wild-type CrtI, almost no desaturated compound was synthesized (FIG. 6A).

The analysis results for peak 2 and peak 3 in FIG. 6B are shown below. $C_{50}$-carotene (n=3): A sample corresponding to peak 2 in FIG. 6B was fractionated by HPLC and subjected to mass spectrometry. The sample showed a much longer HPLC elution time than that of a desaturated carotenoid having the same size, and hence was estimated to be a compound having a $C_{50}$ carotenoid backbone. The absorption spectrum was similar to that of phytoene (n=3). The mass number obtained by the mass spectrometry was 680, which was consistent with that of a putative structure (Compound No. 2 in FIG. 1).

$C_{50}$-lycopene (n=15): A sample corresponding to peak 3 in FIG. 6B was fractionated by HPLC and subjected to mass spectrometry. The HPLC elution time was relatively short. The absorption spectrum was similar to the literature value of 3,4,3',4'-tetradehydrolycopene (n=15) (Karrer and Rutschmann (1945) Helv. Chim. Acta 28: 793-795), and the absorption spectrum had the feature of an acyclic carotenoid. The mass number obtained by the mass spectrometry was 668, which was consistent with that of a putative structure (Compound No. 3 in FIG. 1).

(Example 4) Cyclization of Desaturated $C_{50}$ Carotenoid $C_{50}$-lycopene (n=15), a desaturated $C_{50}$ carotenoid, was cyclized by using a crtY gene encoding a lycopene cyclase, which synthesizes a β-carotenoid from lycopene.

A plasmid pUC-pBAD-crtI/CrtI-m2-crtY was used for transformation with the crtY gene. The plasmid was produced by inserting an SpeI site following an ApaI site in pUC-pBAD-crtI/CrtI-m2 and inserting the crtY gene into the ApaI/SpeI site. The crtY gene is a gene encoding a lycopene cyclase derived from Pantoea ananatis (Misawa N. et al., J Bacteriol 172, 6704-6712 (1990)). It should be noted that the expression "CrtI-m2" in the plasmid means that a mutant gene crtI$_{N304S}$ derived from CrtI-m2 has been inserted. The nucleotide sequence of pUC-pBAD-CrtI-m2-crtY is set forth in SEQ ID NO: 13.

E. coli XL1-Blue harboring pAC-crtM$_{F26A,W38A,F233S}$-fds$_{Y81A,V157A}$ was transformed with pUC-CrtI-m2-CrtY. As a control, transformation was performed with crtY together with wild-type crtI in place of crtI-m2. The E. coli was spread on an LB agar medium on which a nitrocellulose (NC) membrane was mounted, and cultured at 37° C. for 24 hours. After the formation of colonies, the NC membrane with the colonies was transferred onto an LB agar medium containing 0.2% arabinose, followed by incubation at room temperature. Then, the color of the colonies was observed.

Figure 7:
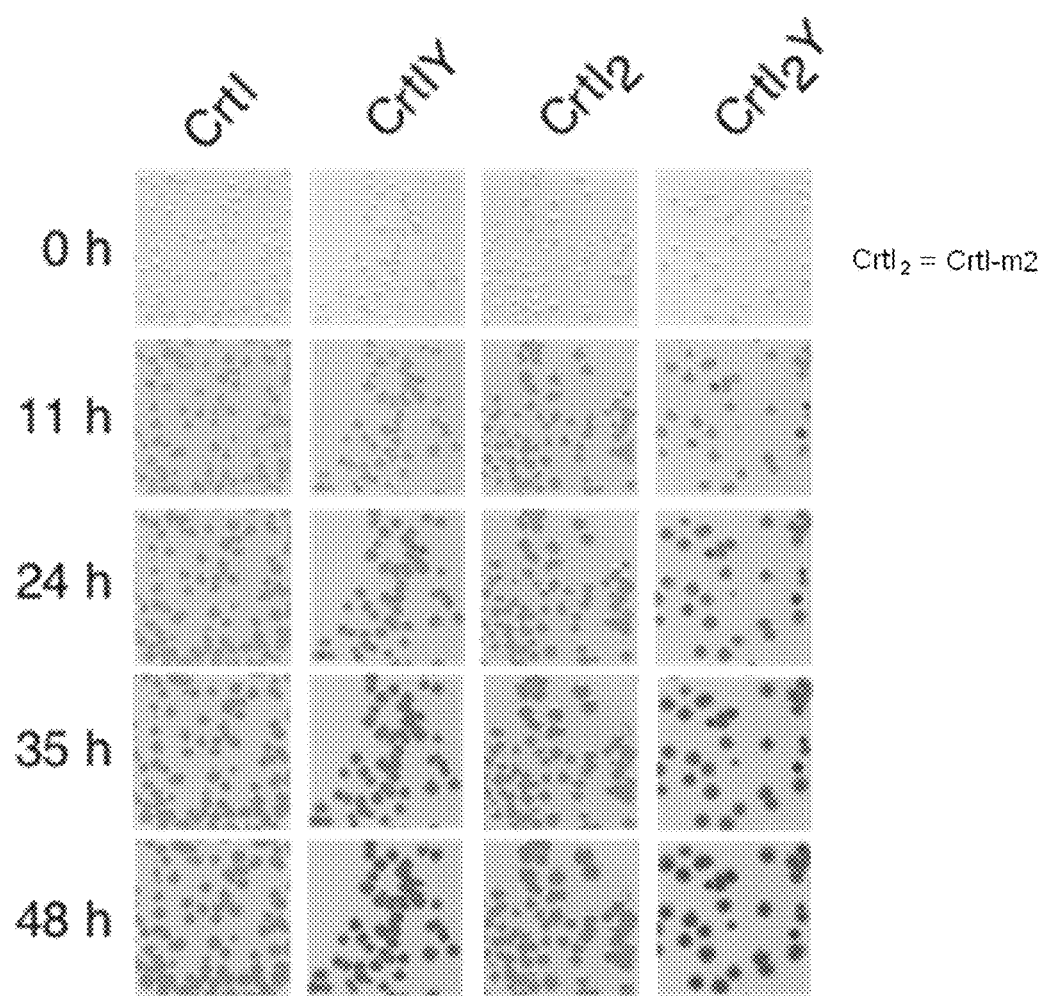
FIG. 7 shows the results of β-cyclic carotenoid synthesis through the cooperation of CrtI with CrtY. The photographs show colony colors in the 0 to 48 hours culture of cells into which various genes have been introduced (Example 4). CrtI shows the case where wild-type crtI was introduced into $E.$ $coli$, CrtIY shows the case where both of wild-type crtI and crtY were introduced into $E.$ $coli$, $CrtI_2$ shows the case where a crtI variant derived from CrtI-m2 was introduced into $E.$ $coli$, and $CrtI_2Y$ shows the case where both of the crtI variant derived from CrtI-m2 and crtY were introduced into $E.$ $coli$. It should be noted that in each $E.$ $coli$ pAC-$fds_{Y81A,V157A}$-$crtM_{F26A,W38A,F233S}$ has been introduced.

FIG. 7 shows the photographs of the transformed E. coli cultured for 0 to 48 hours. The E. coli transformed with a plasmid having crtY downstream of a crtI variant derived from CrtI-m2 ("CrtI$_2$Y" in FIG. 7) developed a very deep red color.

Further, the acetone extract was subjected to HPLC analysis and mass spectrometry by the same techniques as those of Example 3.

A carotenoid having a maximum absorption peak at 502 nm was detected by the HPLC analysis (peak 7 in FIG. 6D). This peak was confirmed in only a trace amount in the case of wild-type CrtI (peak 5 in FIG. 6C). FIG. 1 illustrates the putative structure of the thus obtained $C_{50}$ carotenoid and a synthetic pathway therefor. It should be noted that the numbers of the respective compounds in FIG. 1 correspond to numbers in the chromatograms of FIGS. 6A-6I.

Figure 9A:
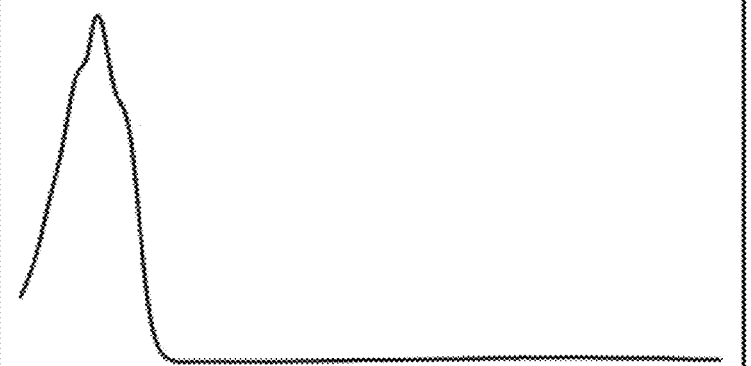
FIGS. 9A-9C show the absorption spectra of $C_{50}$-carotene (n=3), $C_{50}$-lycopene (n=15), and $C_{50}$-β-carotene, respectively in FIGS. 9A, 9B and 9C (Examples 3 and 4).
Figure 9B:
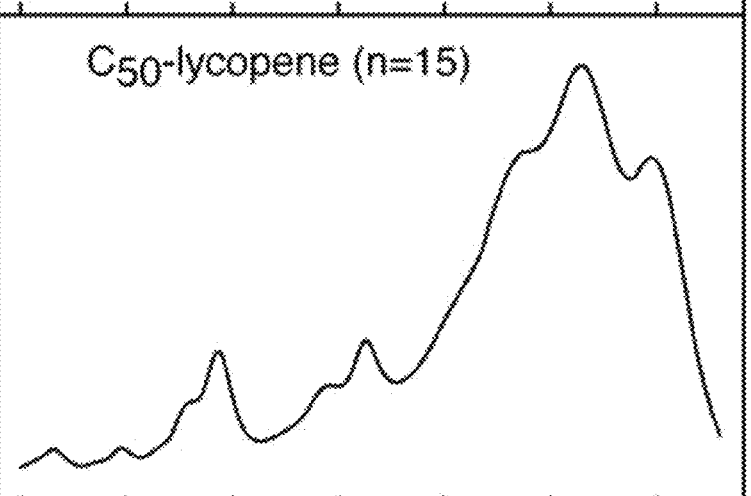
Figure 9C:
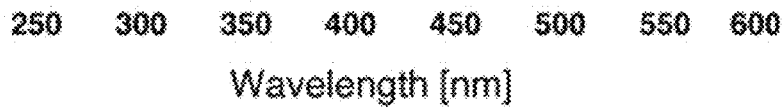

$C_{50}$-β-carotene: A sample corresponding to peak 7 in FIG. 6D was fractionated by HPLC and subjected to mass spectrometry. The HPLC elution time was longer than that of $C_{50}$-lycopene. It is known that a similar behavior is shown in a $C_{40}$ carotenoid as well. The absorption spectrum was almost consistent with that of a chemically synthesized product (Khachik and Beecher (1985) J. Chromatogr. 346: 237-246) (FIG. 9C). The absorption spectrum was similar to one having the feature of a bicyclic carotenoid. The mass number obtained by mass spectrometry was 668, which was consistent with that of a putative structure (Compound No. 7 in FIG. 1).

(Example 5) Extension of Cyclic $C_{50}$ Carotenoid Pathway by Additional Modification An oxocarotenoid was synthesized by further extending the pathway for synthesizing a cyclic $C_{50}$ carotenoid confirmed in Example 4.

pUC-pBAD-crtI-crtWZY (FIG. 2D: SEQ ID NO: 14), a plasmid containing crtW, crtZ, and crtY, was used. As for the plasmid, crtW, crtZ, and crtY of *Paracoccus* sp. strain N81106 (SEQ ID NO: 6) were amplified from a plasmid pAK32 (Misawa N. et al., J Bacteriol 177, 6575-6584 (1995)) by PCR. Through the use of crtW, crtZ, and crtY thus obtained, pUC-pBAD-crtI-crtWZY and pUC-pBAD-CrtI-m2-crtWZY were constructed. In the same manner as the technique of Example 4, the produced plasmids were introduced into *E. coli* (XL1-Blue) together with pAC-crtM$_{F26A,W38A,F233S}$-fds$_{Y81A,V157A}$, and the *E. coli* was cultured, followed by observing the color of colonies.

Figure 8A:
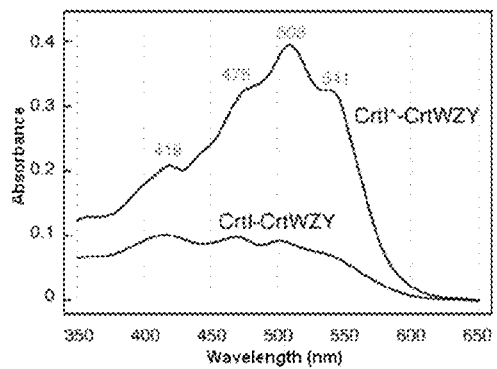
FIGS. 8A-8C show the results of carotenoid synthesis through the cooperation of CrtI with CrtW, CrtZ, and CrtY, in FIG. 8A, and the results of carotenoid synthesis through the cooperation of CrtI with CrtA, in FIG. 8B (Example 5).
Figure 8B:
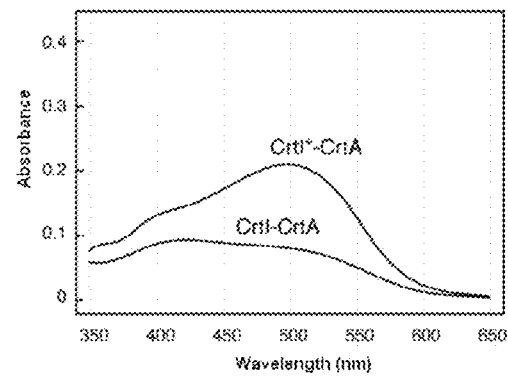
Figure 8C:
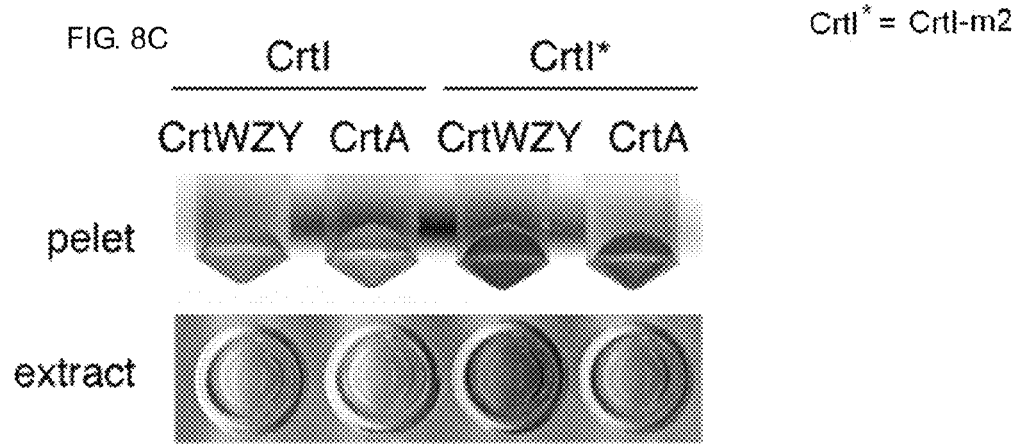

As a result, in a system having introduced therein pUC-pBAD-CrtI-m2-crtWZY, the colonies developed a vivid red color (the second line from the right in FIG. 8C: CrtWZY in CrtI*).

The spectrum of the acetone extract was measured in the same manner as in Example 4. As a result, in the case of transformation with pUC-pBAD-CrtI-m2-crtWZY, an intense peak appeared at 508 nm (CrtI*-CrtWZY in FIG. 8A). On the other hand, in the case of using wild-type CrtI, only a trace amount of a pigment was accumulated (CrtI-CrtWZY in FIG. 8A). HPLC analysis was performed in the same manner as in Example 4. As a result, a novel carotenoid having high polarity and having a maximum absorption peak at 502 nm was obtained as a major peak (peak 9 in FIG. 6F). FIG. 1 illustrates the putative structure of the thus obtained carotenoid and a synthetic pathway therefor. It should be noted that the numbers of the respective compounds in FIG. 1 correspond to numbers in the chromatograms of FIGS. 5A and 5B.

(Example 6) Oxidation of Desaturated $C_{50}$ Carotenoid

The total synthesis of crtA was performed by optimizing a codon for *E. coli* based on the amino acid sequence of CrtA derived from *Rhodobacter* sphearoides (SEQ ID NO: 7, commissioned to DNA2.0). Plasmids pUC-pBAD-crtI-crtA and pUC-pBAD-CrtI-m2-crtA were produced by using the synthesized gene (FIG. 2E: SEQ ID NO: 15).

By the same techniques as those of Example 5, *E. coli* was transformed with the produced plasmids, and the *E. coli* was cultured, followed by observing the color of colonies and analyzing the spectrum of the acetone extract.

As a result, in the case of transformation with pUC-pBAD-CrtI-m2-crtA, the colonies developed a vivid color (the first line from the right in FIG. 8C: CrtA in CrtI*). Further, the acetone extract gave a broad absorption spectrum peculiar to an oxocarotenoid (CrtI*-CrtA in FIG. 8B). In the case of co-expression of CrtA with wild-type CrtI, the colonies developed only a tint color. HPLC analysis was performed in the same manner as in Example 5. As a result, a novel carotenoid having high polarity appeared as a major peak (peak 11 in FIG. 6H).

(Example 7) Acquisition of crtI Variant Having High Ability to Desaturate $C_{50}$ Carotenoid Backbone Compound The biosynthetic pathways for C50-lycopene and C50-β-carotene realized in Examples 3 and 4 left something to be improved in efficiency, because the C50 backbone (C50-carotene (n=3)) still remained. Thus, the acquisition of a CrtI variant having a higher ability to desaturate the C50 backbone was attempted. Of the CrtI variants obtained in Example 2, CrtI-m2 showed the highest C50 backbone desaturation efficiency. Thus, with attention focused on the amino acid substitution N304S of CrtI-m2, the site-directed total substitution of an amino acid at position 304 was performed to search a variant having higher desaturation efficiency.

First, a plasmid pUC-pBAD-crtI containing wild-type CrtI was used as a template, and a library was prepared by PCR using a primer having a randomized amino acid at position 304 (NNK codon) and the subsequent cloning. The resultant plasmid library was screened by the same method as that described in Example 2. Colonies developing a redder color than those of wild-type CrtI were searched to isolate plasmids of CrtI variants. Those CrtI variants were screened again. As a result, products substituted by glycine (G), serine (S), asparagine (N), proline (P), and alanine (A) gave particularly red colonies. Of those, a product substituted by P (codon: CCT) gave the reddest colonies. The amino acid sequence of CrtI having the product substituted by P is set forth in SEQ ID NO: 27 of the sequence listing, and a nucleotide sequence encoding the amino acid sequence is set forth in SEQ ID NO: 28.

Next, the synthesis amounts of C50-lycopene by CrtI-m2 and CrtI$_{N304P}$ were analyzed by HPLC. *E. coli* XL1-Blue was transformed with pUC-pBAD-crtI-m2 or pUC-pBAD-crtI$_{N304P}$ together with pAC-crtM$_{F26A,W38A,F233S}$-fds$_{Y81A,V157A}$. After the formation of colonies, an NC membrane with the colonies was transferred onto an LB agar medium containing 0.2% arabinose, followed by incubation at room temperature. The colonies were inoculated into 2 mL of an LB medium (containing 50 μg/mL carbenicillin and 30 μg/mL chrolamphenicol) and cultured at 37° C. overnight. 300 μL of the culture medium were inoculated into 30 mL of a TB medium (containing 50 μg/mL carbenicillin and 30 μg/mL chrolamphenicol), followed by incubation under shaking at 30° C. and 200 rpm. After the incubation under shaking for 36 hours, 20% arabinose was added to the culture medium so as to have a final concentration of 0.20, followed by incubation under shaking (30°

C.) for an additional 36 hours. HPLC analysis was performed by the method shown in Example 3.

Figure 10:
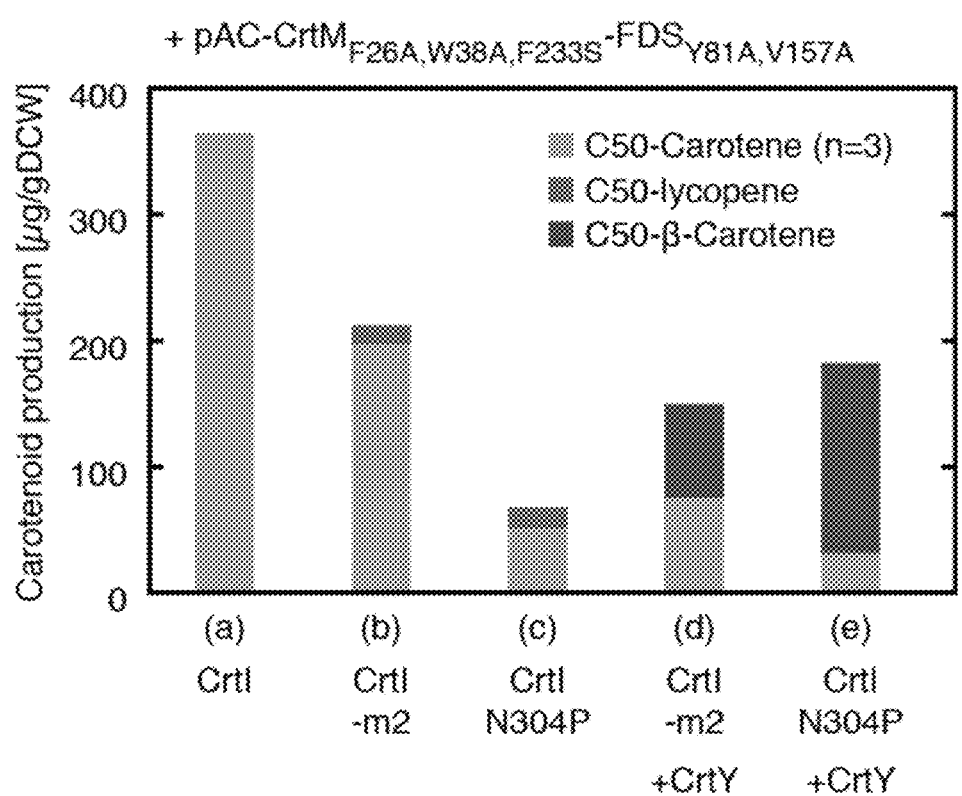
FIG. 10 shows the results of HPLC analysis of synthesis amounts of $C_{50}$-carotene (n=3), $C_{50}$-lycopene, and $C_{50}$-β-carotene by CrtI-m2 and $CrtI_{N304P}$ (Example 7). (a), (b), (c), (d), and (e) show the results of $E.$ $coli$ transformed with pUC-pBAD-CrtI, $E.$ $coli$ transformed with pUC-pBAD-CrtI-m2, $E.$ $coli$ transformed with pUC-pBAD-$CrtI_{N304P}$, $E.$ $coli$ transformed with pUC-pBAD-CrtI-m2-CrtY, and $E.$ $coli$ transformed with pUC-pBAD-$CrtI_{N304P}$-CrtY, respectively. Only $C_{50}$-carotene (n=3) was synthesized in (a), $C_{50}$-carotene (n=3) and $C_{50}$-lycopene were synthesized in (b) and (c), and $C_{50}$-carotene (n=3) and $C_{50}$-β-carotene were synthesized in (d) and (e).

FIG. 10 shows the results. In the case of using CrtI$_{N304P}$, the synthesis amount of C50-lycopene accumulated in the cells showed substantially no increase, whereas the production amount of C50-carotene (n=3) showed a clear decrease as compared to CrtIm2. This is probably because most of C50-lycopene undergoes decomposition because of its low intracellular stability, although the biosynthesis amount of C50-lycopene (desaturation efficiency of C50-carotene) is large (high).

Next, whether or not C50-β-carotene was increased more by using CrtI$_{N304P}$ was investigated. First, a pUC-pBAD-crtI$_{N304P}$-crtY plasmid was prepared. *E. coli* XL1-Blue was transformed with the plasmid and pUC-pBAD-crtI-m2-crtY together with pAC-crtM$_{F26A,W38A,F233S}$-fds$_{Y81A,V157A}$, and culturing, extraction, and HPLC analysis were performed in the same manner as in the above-mentioned sections.

As a result, C50-carotene (n=3) was decreased and C50-lycopene was increased in the case of using CrtI$_{N304P}$ as compared to the case of using CrtI-m2 (FIG. 10).

(Example 8) Study on Use of CrtW and CrtZ Derived from *Brevundimonas* sp. Strain SD-212

In Example 5, it was attempted to produce C50-astaxanthin, in addition to C50-β-carotene, by the use of CrtW and CrtZ derived from *Paracoccus* sp. strain N81106. A polar peak appeared, but most of C50-β-carotene remained without any modification by CrtW or CrtZ. Thus, the synthesis of C50-astaxanthin and its intermediates C50-zeaxanthin and C50-canthaxanthin was attempted by the use of CrtW and CrtZ having higher efficiency.

Figure 11A:
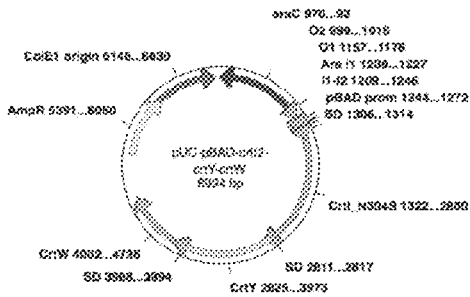
FIGS. 11A-11D illustrate plasmid maps used in Examples 8 and 9. The plasmids contain CrtW and/or CrtZ derived from $Brevundimonas$ sp. strain SD-212.
Figure 11B:
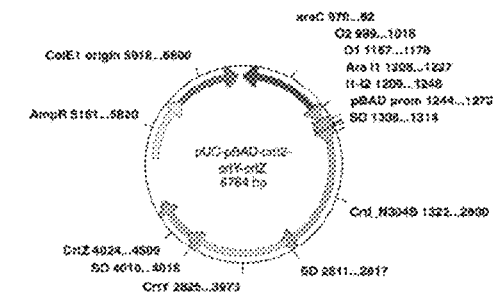
Figure 11C:
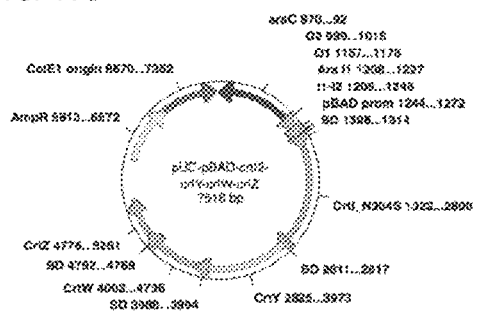

As previously reported (Choi S. et al., Mar Biotechnol 7, 515-522 (2005), Choi S. et al., Appl Microbiol Biotechnol 72, 1238-1246 (2006)), it has been found that CrtW and CrtZ derived from *Brevundimonas* sp. strain SD-212 are a β-carotene ketolase and β-carotene hydroxylase having high efficiency, respectively. In the synthesis of a natural (C40 type) astaxanthin, the enzymes are the best choices that are currently available. Thus, the total synthesis of those genes was performed with codon optimization for *E. coli*, which was commissioned to DNA2.0. Through the use of those genes, pUC-pBAD-CrtI$_{N304P}$-CrtY-CrtW$_{BD}$-CrtZ$_{BD}$ was prepared. Further, pUC-pBAD-CrtI-m2-CrtY-CrtW$_{BD}$ and pUC-pBAD-CrtI-m2-CrtY-CrtZ$_{BD}$ were also prepared. The plasmid maps of pUC-pBAD-CrtI-m2-CrtY-CrtW$_{BD}$, pUC-pBAD-CrtI-m2-CrtY-CrtZ$_{BD}$, and pUC-pBAD-CrtI$_{N304P}$-CrtY-CrtW$_{BD}$-CrtZ$_{BD}$ are illustrated in FIGS. 11A, 11B, and 11C, respectively, and the nucleotide sequences thereof are set forth in SEQ ID NOS: 16, 17, and 18, respectively.

Those plasmids were introduced into *E. coli* (XL1-Blue) together with pAC-crtM$_{F26A,W38A,F233S}$-fds$_{Y81A,V157A}$, and culturing and extraction were performed by the method shown in Example 3. The obtained carotenoid extracts were each injected into an HPLC-photodiodearray system. Analysis was performed at a flow rate of 1 mL/min by using a μBondapak column (100×8 mm, RCM-type, Waters) as a column and using methanol as an eluent.

Figure 12:
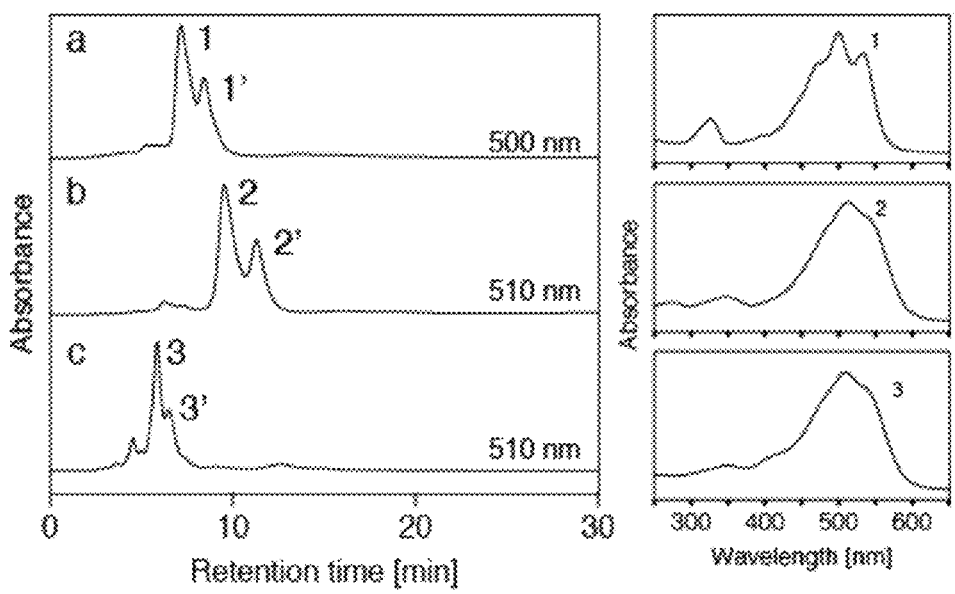
FIG. 12 shows the results of HPLC analysis of C50-zeaxanthin, C50-canthaxanthin, and C50-astaxanthin produced in the case where $E.$ $coli$ was transformed with various plasmids containing CrtW and/or CrtZ derived from $Brevundimonas$ sp. strain SD-212 and pAC-$crtM_{F26A,W38A,F233S}$-$fds_{Y81A,V157A}$ and cultured (Example 8). (a), (b), and (c) show the results of transformation with pUC-pBAD-CrtI-m2-CrtY-$CrtZ_{BD}$, pUC-pBAD-CrtI-m2-CrtY-$CrtW_{BD}$, and pUC-pBAD-$CrtI_{N304P}$-CrtY-$CrtW_{BD}$-$CrtZ_{BD}$, respectively, together with pAC-$CrtM_{F26A,W38A,F233S}$-$fds_{Y81A,V157A}$. Numerals 1, 2, and 3 in FIG. 12 represent the peaks of C50-zeaxanthin, C50-canthaxanthin, and C50-astaxanthin, respectively, and numerals with dashes (primes) represent cis peaks thereof.

As a result, C50-zeaxanthin was specifically synthesized in pUC-pBAD-CrtI-m2-CrtY-CrtZ$_{BD}$ (panel a in FIG. 12), and C50-canthaxanthin was specifically synthesized in the case of using pUC-pBAD-CrtI-m2-CrtY-CrtW$_{BD}$ (panel b in FIG. 12). Further, C50-astaxanthin was specifically synthesized in the case of using pUC-pBAD-CrtI$_{N304P}$-CrtY-CrtW$_{BD}$-CrtZ$_{BD}$ (panel c in FIG. 12).

(Example 9) Increase in C50-Astaxanthin Amount by Co-Expression of Idi

C50-astaxanthin was synthesized in *E. coli* by the method described in Example 8 using pAC-crtM$_{F26A,W38A,F233S}$-fds$_{Y81A,V157A}$ and pUC-pBAD-CrtI$_{N304P}$-CrtY-CrtW$_{BD}$-CrtZ$_{BD}$, and a synthesis amount thereof was determined from an HPLC peak area thereof.

Figure 13:
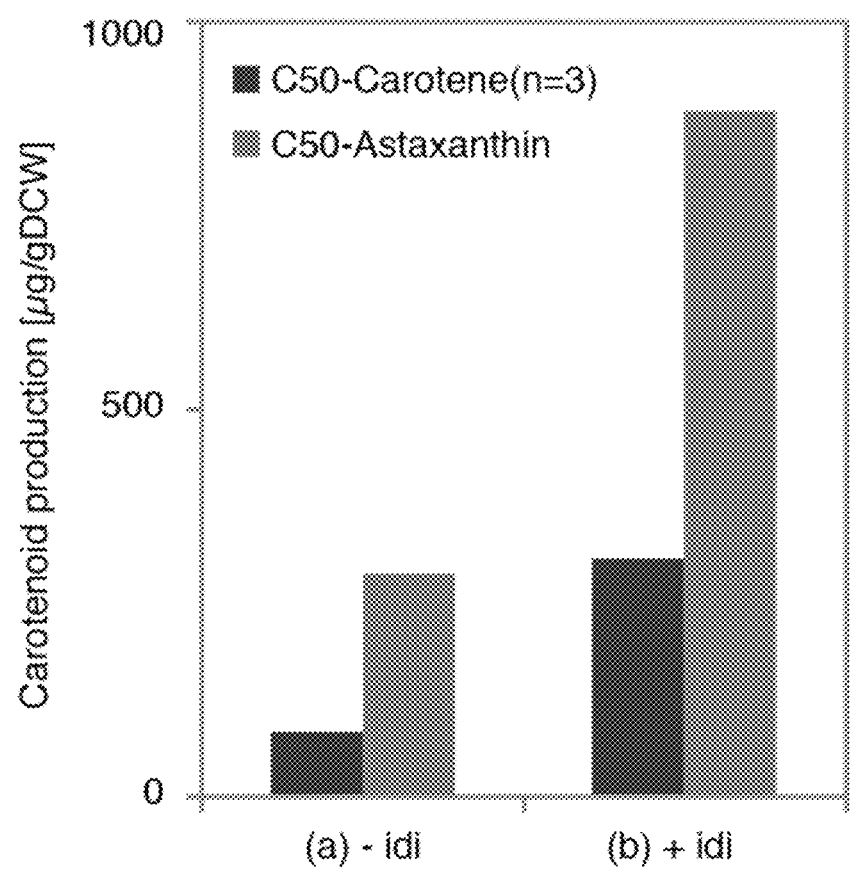
FIG. 13 shows that idi co-expression remarkably increased the synthesis amount of C50-astaxanthin in $E.$ $coli$ transformed with pUC-pBAD-$CrtI_{N304P}$-CrtY-$CrtW_{BD}$-$CrtZ_{BD}$ and pAC-$crtM_{F26A,W38A,F233S}$-$fds_{Y81A,V157A}$ (Example 9). (a) shows the results when co-expressing no idi, that is, the synthesis amounts of C50-carotene (n=3) and C50-astaxanthin in $E.$ $coli$ transformed with pAC-$crtM_{F26A,W38A,F233S}$-$fds_{Y81A,V157A}$ and pUC-pBAD-$CrtI_{N304P}$-CrtY-$CrtW_{BD}$-$CrtZ_{BD}$. (b) shows the results when co-expressing idi, that is, the synthesis amounts of C50-carotene (n=3) and C50-astaxanthin in $E.$ $coli$ transformed with pAC-$crtM_{F26A,W38A,F233S}$-$fds_{Y81A,V157A}$-idi and pUC-pBAD-$CrtI_{N304P}$-CrtY-$CrtW_{BD}$-$CrtZ_{BD}$.

As a result, C50-astaxanthin was synthesized at 288 μg/gDCW (FIG. 13).

Figure 11D:
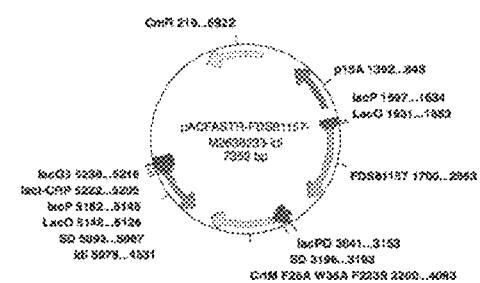

In order to co-express idi therewith, pAC-crtM$_{F26A,W38A,F233S}$-fds$_{Y81A,V157A}$-idi was prepared and transformed into *E. coli* (XL1-Blue) together with pUC-pBAD-CrtI$_{N304P}$-CrtY-CrtW$_{BD}$-CrtZ$_{BD}$. Then, a carotenoid synthesis amount was determined by a similar method. The plasmid map of pAC-CrtM$_{F26A,W38A,F233S}$-fds$_{Y81A,V157A}$-idi is illustrated in FIG. 11D and the nucleotide sequence thereof is set forth in SEQ ID NO: 19.

As a result, C50-astaxanthin was synthesized at 884 μg/gDCW (FIG. 13).

Example 10

A compound in the peak of C50-β-carotene obtained in Example 4 (peak 7 in FIG. 6D) and compounds in the peaks of C50-zeaxanthin, C50-canthaxanthin, and C50-astaxanthin identified in Example 8 (peaks 1, 2, and 3 in FIG. 12) were identified.

The maximum absorption wavelengths of the compound in the peak (peak 7 in FIG. 6D) of C50-β-carotene were 467 (shoulder), 501, and 534 nm in methanol, which was shifted to the lower wavelength side than those of C50-lycopene. Thus, it is apparent that the compound is a carotenoid having a ring structure (Takaichi, S. & Shimada, K. Methods Enzymol. 213, 374-385 (1992)). Further, the prolonged elution time in reverse phase HPLC also indicates that cyclization occurred. The molecular mass was 668, which was identical to a value calculated for C50-β-carotene.

Figure 14:
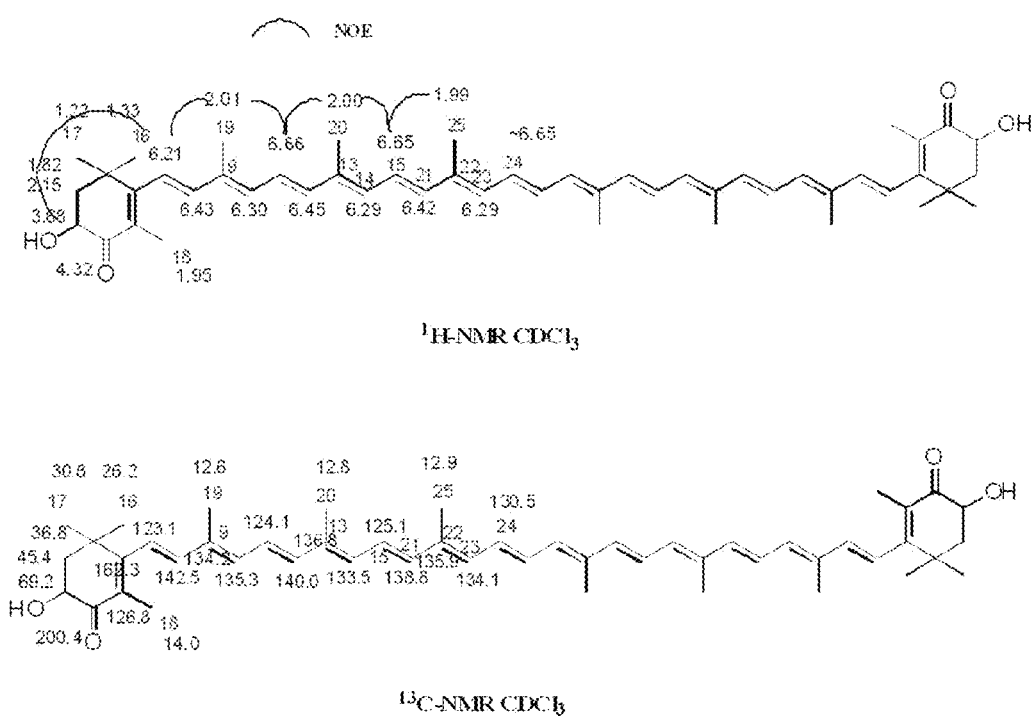
FIG. 14 shows the result of identification by NMR analysis, which indicates that a compound synthesized in $E.$ $coli$ transformed with pUC-pBAD-$CrtI_{N304P}$-CrtY-$CrtW_{BD}$-$CrtZ_{BD}$ and pAC-$crtM_{F26A,W38A,F233S}$-$fds_{Y81A,V157A}$ was C50-astaxanthin (Example 10).

The compound in the peak (peak 3 in FIG. 12) of 50-astaxanthin gave a broad absorption spectrum having a maximum absorption wavelength at 512 nm in methanol. The molecular mass was 728, which was consistent with a value predicted from the structural formula of C50-astaxanthin. In addition, it was attempted to determine a partial structure thereof by chemical derivatization in accordance with the previous report (S. Takaichi et al., Org. Mass Spectroscopy, 28, 785-788 (1993)). This compound, when subjected to reduction with NaBH$_4$, gave the same absorption spectrum as that of C50-β-carotene, and had a molecular mass increased to 732. This revealed the presence of two carbonyl groups at the 4,4'-positions. When the compound before NABH$_4$ treatment was used to prepare its diacetyl and ditrimethylsilyl derivatives, the molecular masses were 812 and 872, respectively. The increases correspond to increases in molecular weight of two acetyl groups and two trimethylsilyl groups, respectively. This revealed the presence of two hydroxyl groups. On the other hand, when the compound after NABH$_4$ treatment was used to prepare its diacetyl and ditrimethylsilyl derivatives in the same manner as described above, the molecular masses were 900 and 1,020, respectively. In other words, the presence of four hydroxyl groups could be confirmed. In addition, when the compound was purified and subjected to NMR analysis, the compound was clearly identified as C50-astaxanthin (FIG. 14).

The compound in the peak (peak 1 in FIG. 12) of C50-zeaxanthin had a molecular mass of 700, which HPLC elution profile and absorption spectrum were as shown in panel (a) of FIG. 12. The compound was determined as C50-zeaxanthin by considering the shift of its elution peak to the polar side and so on.

The compound in the peak (peak 2 in FIG. 12) of C50-canthaxanthin had a molecular mass of 696, which HPLC elution profile and absorption spectrum were as shown in panel (b) of FIG. 12. Thus, the compound was identified as C50-canthaxanthin in consideration of, for example, the shift of its elution peak to the polar side.

(Example 11) Production of Carotenoids Having Great Variety of Structures by Additional Expression of CrtG and CrtX A study on the diversification of carotenoid structures to be synthesized was made by the additional expression of a crtG gene derived from *Brevundimonas* sp. strain SD-212 (Nishida, Y. et al, Appl Environ Microbiol 71, 4286-4296, 2005) and a crtX gene derived from *Pantoea ananatis*. The crtX gene is a gene encoding a zeaxanthin glucosyl transferase.

Figure 15A:
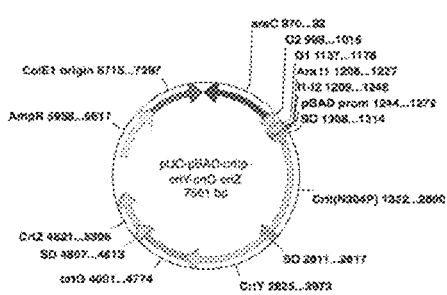
FIGS. 15A-15D illustrate plasmid maps used in Example 11. The plasmids contain, in addition to CrtW and/or CrtZ derived from $Brevundimonas$ sp. strain SD-212, CrtG derived from $Brevundimonas$ sp. strain SD-212 or CrtX derived from $Pantoea$ $ananatis$.
Figure 15B:
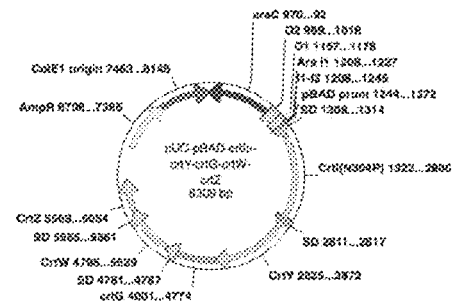

First, pUC-pBAD-CrtI$_{N304P}$-CrtY-CrtG-CrtZ$_{BD}$ and pUC-pBAD-CrtI$_{N304P}$-CrtY-CrtG-CrtW$_{BD}$-CrtZ$_{BD}$ were prepared by using the crtG gene derived from *Brevundimonas* sp. strain SD-212. The plasmid maps of pUC-pBAD-CrtI$_{N304P}$-CrtY-CrtG-CrtZ$_{BD}$ and pUC-pBAD-CrtI$_{N304P}$-CrtY-CrtG-CrtW$_{BD}$-CrtZ$_{BD}$ are illustrated in FIGS. 15A and 15B, respectively, and the nucleotide sequences thereof are set forth in SEQ ID NOS: 20 and 21, respectively.

Figure 16:
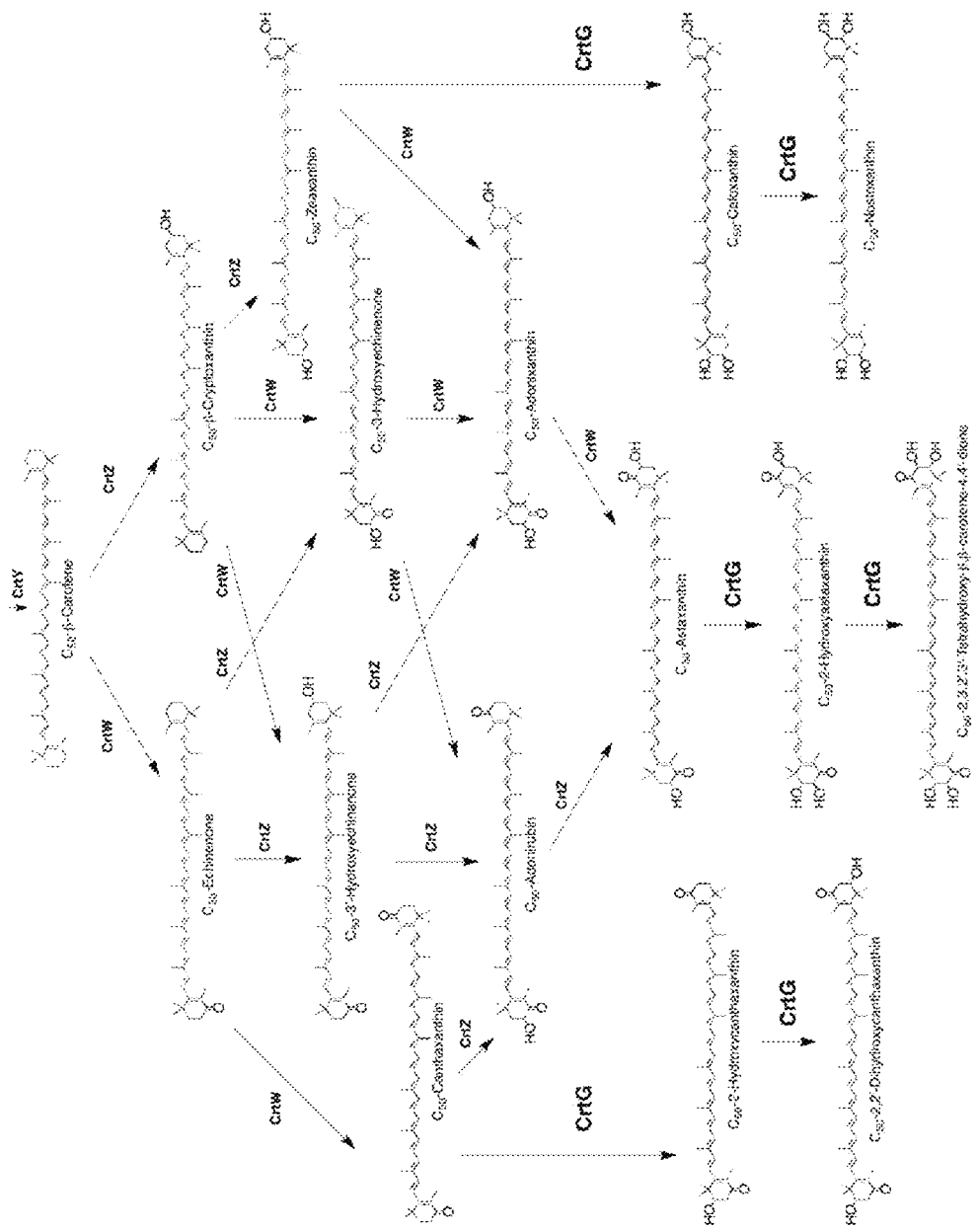
FIG. 16 illustrates that more varieties of carotenoids can be produced by the additional expression of CrtG in carotenoid biosynthetic pathways (Example 11). Through the additional expression of CrtG, $C_{50}$-2-hydroxyastaxanthin and $C_{50}$-2,3,2',3'-tetrahydroxy-β,β-carotene-4,4'-dione are produced from $C_{50}$-astaxanthin. $C_{50}$-caloxanthin and $C_{50}$-nostoxanthin are produced from $C_{50}$-zeaxanthin. Further, $C_{50}$-2-hydroxycanthaxanthin and $C_{50}$-2,2'-dihydroxycanthaxanthin are produced from $C_{50}$-canthaxanthin.

In the case of culturing *E. coli* co-expressing pUC-pBAD-CrtI$_{N304P}$-CrtY-CrtG-CrtZ$_{BD}$ and pAC-CrtM$_{F26A,W38A,F233S}$-FDS$_{Y81A,V157A}$, C$_{50}$-caloxanthin and C$_{50}$-nostoxanthin, which are hydroxylated zeaxanthin at the 2-position and 2'-position, can be synthesized (FIG. 16).

In the case of culturing *E. coli* co-expressing pUC-pBAD-CrtI$_{N304P}$-CrtY-CrtG-CrtW$_{BD}$-CrtZ$_{BD}$ and pAC-CrtM$_{F26A,W38A,F233S}$-FDS$_{Y81A,V157A}$, C$_{50}$-2-hydroxyastaxanthin and C$_{50}$-2,3,2',3'-tetrahydroxy-β,β-carotene-4,4'-dione, which are hydroxylated astaxanthin at the 2-position and 2'-position, can be synthesized (FIG. 16).

Further, it is also possible to synthesize C$_{50}$-2-hydroxycanthaxanthin and C$_{50}$-2,2'-dihidroxycanthaxanthin, which are hydroxylated canthaxanthin at the 2-position and 2'-position (FIG. 16).

Figure 15C:
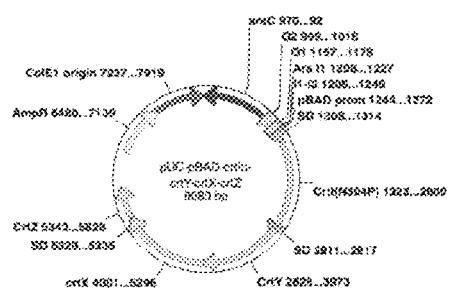
Figure 15D:
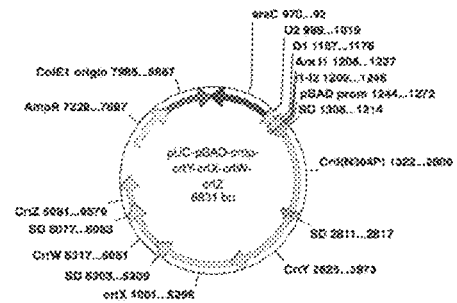

Next, pUC-pBAD-CrtI$_{N304P}$-CrtY-CrtX-CrtZ$_{BD}$ and pUC-pBAD-CrtI$_{N304P}$-CrtY-CrtX-CrtW$_{BD}$-CrtZ$_{BD}$ were prepared by using the crtX gene derived from *Pantoea ananatis*. The plasmid maps of pUC-pBAD-CrtI$_{N304P}$-CrtY-CrtX-CrtZ$_{BD}$ and pUC-pBAD-CrtI$_{N304P}$-CrtY-CrtX-CrtW$_{BD}$-CrtZ$_{BD}$ are illustrated in FIGS. 15C and 15D, respectively, and the nucleotide sequences thereof are set forth in SEQ ID NOS: 22 and 23, respectively.

Figure 17:
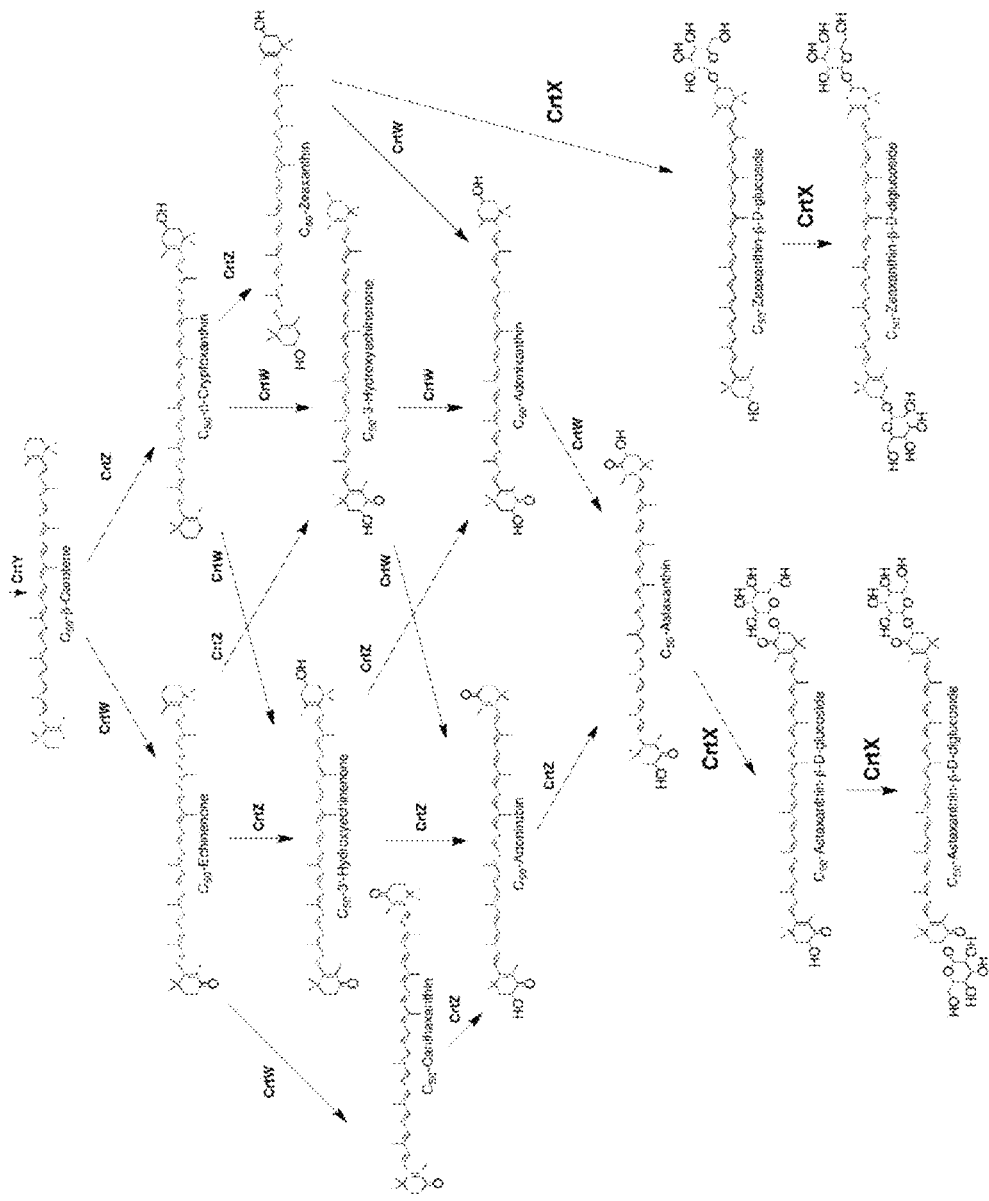
FIG. 17 illustrates that more varieties of carotenoids can be produced by the additional expression of CrtX in carotenoid biosynthetic pathways (Example 11). Through the additional expression of CrtX, $C_{50}$-astaxanthin-β-D-glucoside and $C_{50}$-astaxanthin-β-D-diglucoside are produced from $C_{50}$-astaxanthin. $C_{50}$-zeaxanthin-β-D-glucoside and $C_{50}$-zeaxanthin-3-D-diglucoside are produced from $C_{50}$-zeaxanthin.

In the case of culturing *E. coli* co-expressing pUC-pBAD-CrtI$_{N304P}$-CrtY-CrtX-CrtZ$_{BD}$ and pAC-CrtM$_{F26A,W38A,F233S}$-FDS$_{Y81A,V157A}$, C$_{50}$-zeaxanthin-β-D-glucoside and C$_{50}$-zeaxanthin-β-D-diglucoside, which are glycosidated zeaxanthin at the hydroxyl groups at the 3-position and 3'-position, can be synthesized (FIG. 17).

In the case of culturing *E. coli* co-expressing pUC-pBAD-CrtI$_{N304P}$-CrtY-CrtX-CrtW$_{BD}$-CrtZ$_{BD}$ and pAC-CrtM$_{F26A,W38A,F233S}$-FDS$_{Y81A,V157A}$, C$_{50}$-astaxanthin-β-D-glucoside and C$_{50}$-astaxanthin-β-D-diglucoside, which are glycosidated astaxanthin at the hydroxyl groups at the 3-position and 3'-position, can be synthesized (FIG. 17).

Figure 18:
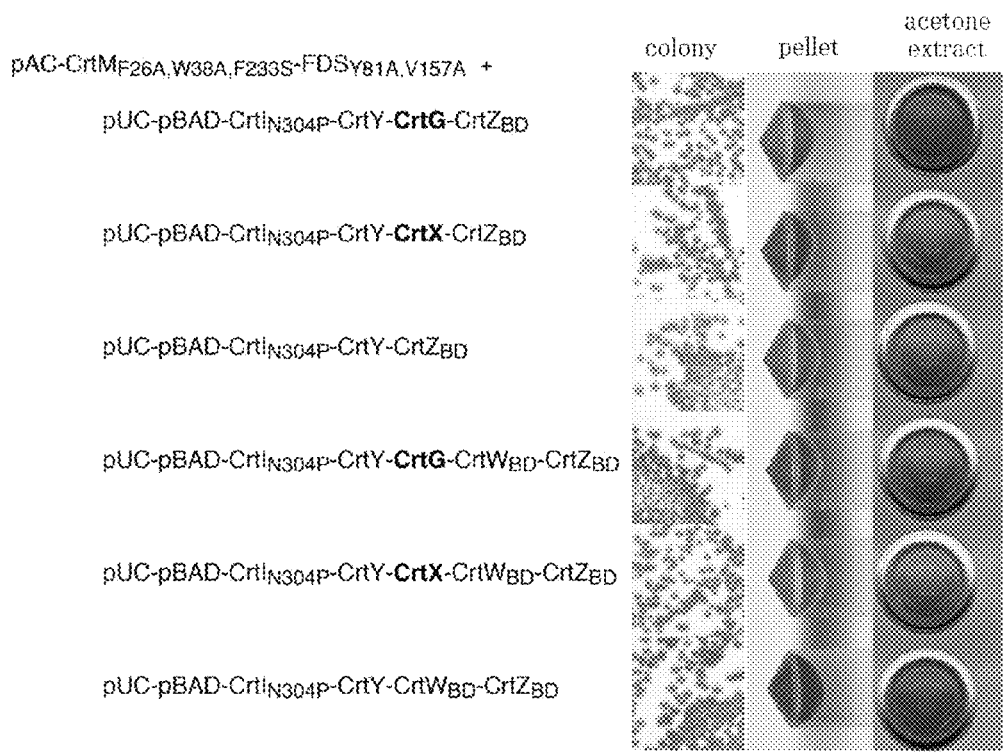
FIG. 18 shows the results of confirmation of the fact that a great variety of carotenoids were able to be produced by the additional expression of CrtG or CrtX in $E.$ $coli$ strains that specifically synthesize C50-zeaxanthin and C50-astaxanthin, based on colony colors, cell pellet colors, and carotenoid extract colors (Example 11).

In fact, when *E. coli* (XL1-Blue) co-expressing any one of pUC-pBAD-CrtI$_{N304P}$-CrtY-CrtG-CrtZ$_{BD}$, pUC-pBAD-CrtI$_{N304P}$-CrtY-CrtX-CrtZ$_{BD}$, pUC-pBAD-CrtI$_{N304P}$-CrtY-CrtG-CrtW-CrtZ$_{BD}$, and pUC-pBAD-CrtI$_{N304P}$-CrtY-CrtX-CrtW$_{BD}$-CrtZ$_{BD}$ together with pAC-CrtM$_{F26A,W38A,F233S}$-FDS$_{Y81A,V157A}$ was spread on an LB solid medium to form colonies, the formed colonies developed a reddish violet color (FIG. 18).

Figure 19A:
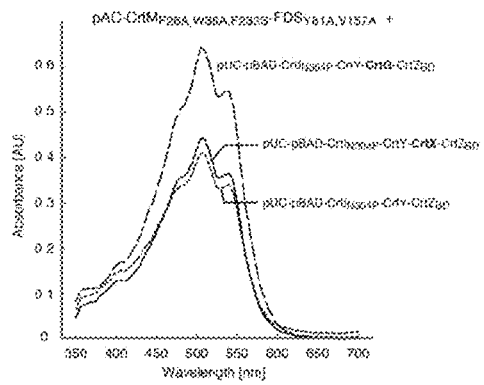
FIGS. 19A and 19B show the results of measurement of absorption spectra of carotenoid extracts obtained by the additional expression of CrtG or CrtX in $E.$ $coli$ strains that specifically synthesize C50-zeaxanthin and C50-astaxanthin (Example 11).
Figure 19B:
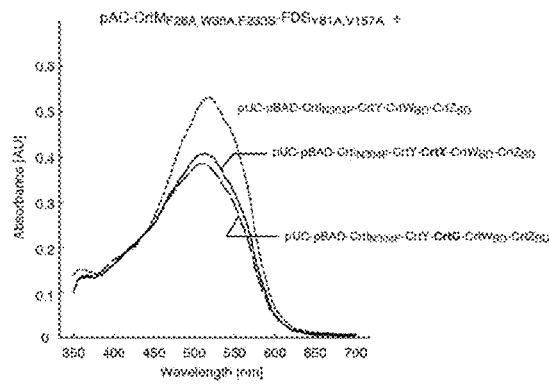

The colonies were inoculated into 2 mL of an LB liquid medium and cultured for 16 hours. After that, the culture medium was inoculated into 30 mL of a TB liquid medium in a 1/100 volume with respect to the TB liquid medium. After incubation under rotation at 200 rpm at 30° C. for 36 hours, L-arabinose was added so as to have a final concentration of 0.2% (v/v), followed by incubation for an additional 36 hours. The cells were harvested and collected from 2 mL of the culture medium and washed with physiological saline, and then a carotenoid fraction was extracted with the addition of 1 mL of acetone. FIG. 18 shows the cell pellets and the acetone extracts. Further, FIGS. 19A and 19B show the absorption spectra of the respective extracts.

Next, *E. coli* (XL1-Blue) was transformed with pUC-pBAD-CrtI$_{N304P}$-CrtY-CrtX-CrtZ$_{BD}$ or pUC-pBAD-CrtI$_{N304P}$-CrtY-CrtG-CrtZ$_{BD}$ and pAC-CrtM$_{F26A,W38A,F233S}$-FDS$_{Y81A,V157A}$. The cell colonies were inoculated into 2 mL of an LB liquid medium and cultured for 16 hours. After that, the culture medium was inoculated into 30 mL of a TB liquid medium in a 1/100 volume with respect to the TB liquid medium. After incubation under rotation at 200 rpm at 30° C. for 36 hours, L-arabinose was added so as to have a final concentration of 0.2% (v/v), followed by incubation for an additional 36 hours. The cells were harvested by centrifuging the culture medium and washed with physiological saline. 10 mL of acetone were added to the cell pellet to extract a carotenoid fraction. 1 mL of chloroform and 35 mL of 10% NaCl were added to the acetone extract to extract the carotenoid fraction into a chloroform phase. All the chloroform extracts were collected and dehydrated with the addition of MgSO$_4$. The chloroform solvent was eliminated by nitrogen, and the carotenoid fraction was finally concentrated into 100 μL of methanol/THF (1:1, v/v). Thus, a carotenoid extract was obtained. 10 μL (10% of the total volume, corresponding to 3 mL of the medium) of the obtained carotenoid extract were injected into an HPLC-photodiodearray system. HPLC analysis was performed in accordance with the conditions of Nishida, Y. et al, Appl Environ Microbiol, 71, 4286-4296 (2005) (column: TSK gel ODS-80 Ts column (4.6-mm inner diameter by 150 mm; Tosoh Co.), eluent: Eluent A (methanol/water, 95:5) for 5 minutes, Eluent A to Eluent B (methanol/tetrahydrofuran, 7:3) for 5 minutes, Eluent B for 15 minutes, 1 mL/min, detector: photodiode array (190 to 800 nm)).

Figure 20:
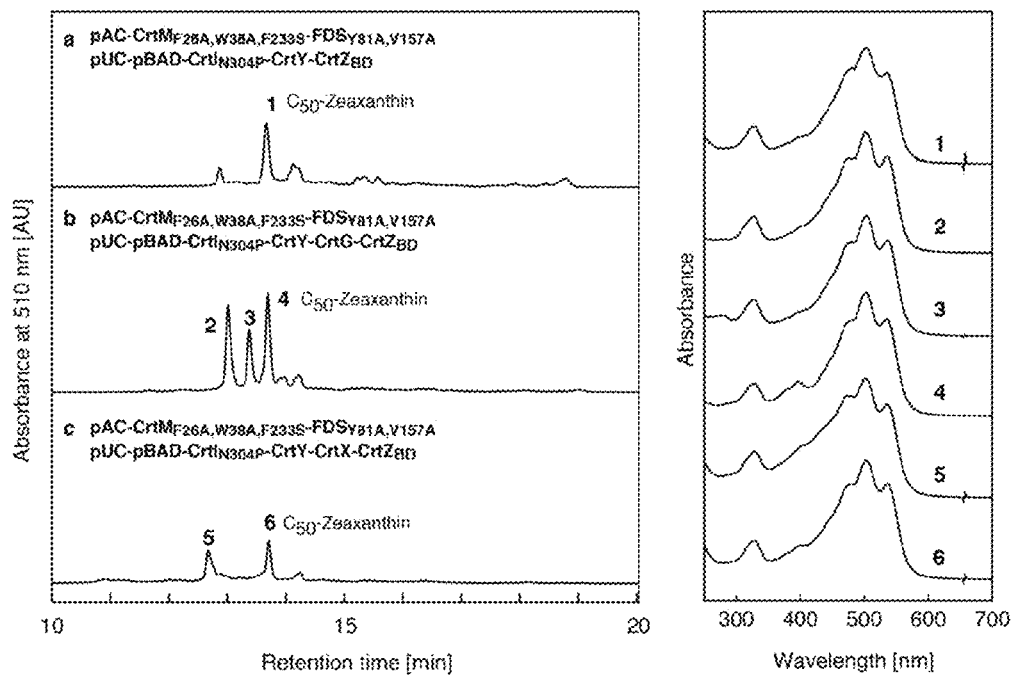
FIG. 20 show the results of HPLC analysis of a carotenoid produced by the additional expression of CrtG or CrtX in an $E.$ $coli$ strain that specifically synthesizes C50-zeaxanthin (Example 11).

As a result, in the case of co-expression of CrtX with C50-zeaxanthin, one new peak appeared at a shorter elution time (peak in FIG. 20). A compound in the peak is estimated to be C50-zeaxanthin-β-D-diglucoside because of having the same absorption spectrum as that of C50-zeaxanthin and having higher polarity than that of C50-zeaxanthin.

Further, in the case of co-expression of CrtG with C50-zeaxanthin, two new peaks appeared (peaks 2 and 3 in FIG. 20). Compounds in the peaks are estimated to be C50-caloxanthin (peak 3 in FIG. 20) and C50-nostoxanthin (peak 2 in FIG. 20) because of, for example, having the same absorption spectrum as that of C50-zeaxanthin and having higher polarity.

(Example 12) Biosynthesis of $C_{55}$ and $C_{60}$ Carotenoids

A mutant FDS having introduced therein mutations I78G and Y81A ($FDS_{I78G,Y81A}$) synthesizes $C_{25}$PP and a prenyl diphosphate (e.g., $C_{30}$PP or $C_{35}$PP) which is a resultant of further addition of $C_5$ unit(s) to $C_{25}$PP (Ohnuma S et al., J Biol Chem 273, 26705-26713, 1998). Further, a $C_{30}$PP synthase (HexPS) derived from *Micrococcus luteus* synthesizes $C_{30}$PP (Shimizu N et al, J Bacteriol 180, 1578-1581, 1998). The biosynthesis of a larger carotenoid backbone than a $C_{50}$ backbone was attempted by co-expressing $FDS_{I78G,Y81A}$ or HexPS with a CrtM variant.

Figure 21A:
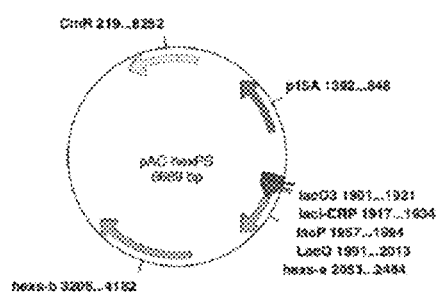
FIGS. 21A-21C illustrate plasmid maps used in Example 12.
Figure 21B:
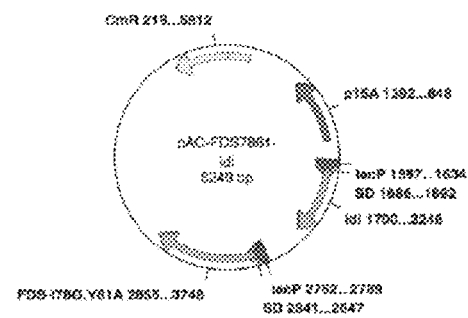
Figure 21C:
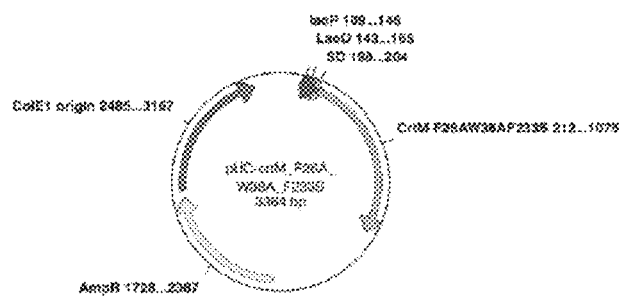

First, pAC-hexPS, $pAC-FDS_{I78G,Y81A}$-idi, and $pUC-CrtM_{F26A,W38A,F233S}$ were prepared. The plasmid maps of pAC-hexPS, $pAC-FDS_{I78G,Y81A}$-idi, and $pUC-CrtM_{F26A,W38A,F233S}$ are illustrated in FIGS. 21A, 21B, and 21C, respectively, and the nucleotide sequences thereof are set forth in SEQ ID NOS: 24, 25, and 26, respectively.

*E. coli* (XL1-Blue) was transformed with $pAC-FDS_{I78G,Y81A}$-idi or pAC-hexPS together with $pUC-CrtM_{F26A,W38A}$ or $pUC-CrtM_{F26A,W38A,F233S}$. The culturing of the cells and the analysis of the produced carotenoid were performed in the same manner as in Reference Example 1.

Figure 22:
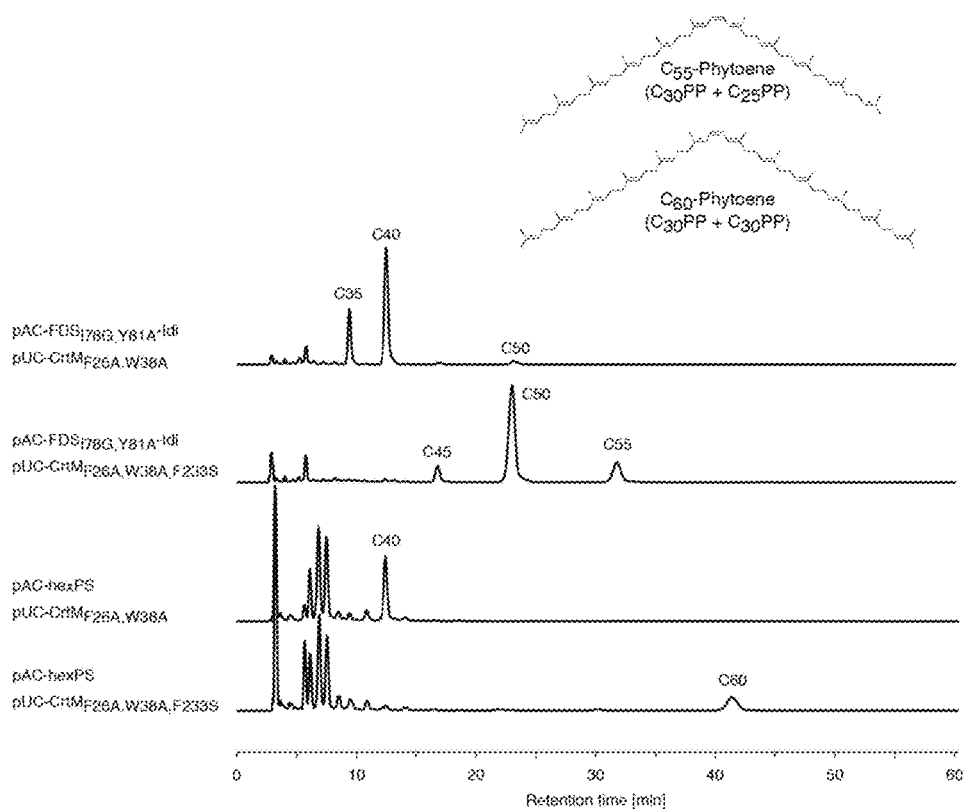
FIG. 22 shows the results of biosynthesis of a $C_{55}$ carotenoid and a $C_{60}$ carotenoid (Example 12). When co-expressing $CrtM_{F26A,W38A,F233S}$ with pAC-$FDS_{I78G,Y81A}$-idi, the $C_{55}$ carotenoid was produced in addition to $C_{45}$ and $C_{50}$ carotenoids. Further, when co-expressing $CrtM_{F26A,W38A,F233S}$ with hexPS, the $C_{60}$ carotenoid was specifically synthesized. On the other hand, when using $CrtM_{F26A,W38A}$, it was impossible to confirm the production of any of the $C_{55}$ carotenoid and the $C_{60}$ carotenoid.

FIG. 22 shows the results. In the case of using $CrtM_{F26A,W38A,F233S}$, a $C_{55}$ carotenoid was produced in addition to $C_{45}$ and $C_{50}$ carotenoids under co-expression of $pAC-FDS_{I78G,Y81A}$-idi therewith. Further, a $C_{60}$ carotenoid was specifically synthesized under co-expression of hexPS therewith. On the other hand, in the case of using $CrtM_{F26A,W38A}$, it was impossible to confirm the production of any of the $C_{55}$ carotenoid and the $C_{60}$ carotenoid. Accordingly, the F233S mutation of CrtM is essential for the production of the $C_{55}$ carotenoid and the $C_{60}$ carotenoid.

Figure 23:
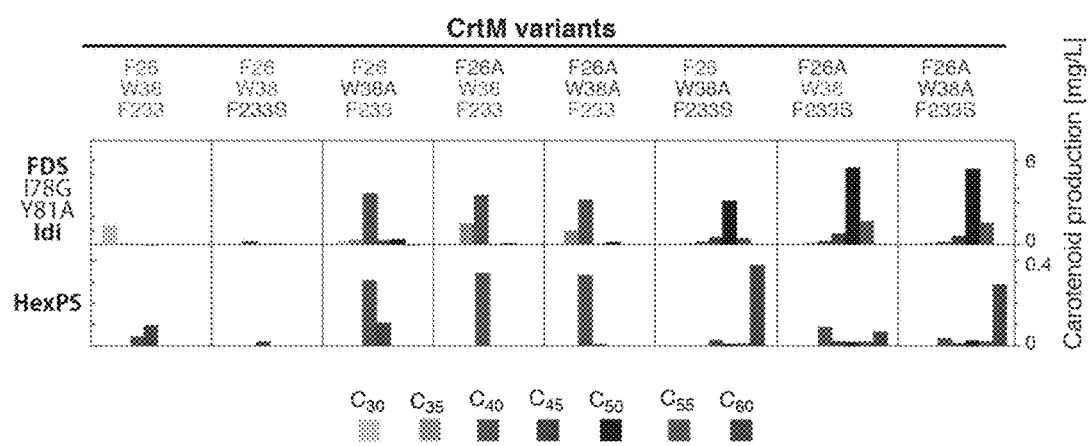
FIG. 23 shows the results of measurement of carotenoid synthesis amounts when co-expressing AC-$FDS_{I78G,Y81A}$-idi or pAC-hexPS with 8 kinds of CrtM variants (pUC-CrtM variants) (Example 12). A larger amount of a $C_{55}$ carotenoid was synthesized in cells co-expressing $FDS_{I78G,Y81A}$-idi with $CrtM_{F26A,F233S}$ or $CrtM_{F26A,W38A,F233S}$. Further, a larger amount of a $C_{60}$ carotenoid was synthesized in cells co-expressing HexPS with $CrtM_{W38A,F233S}$ or $CrtM_{F26A,W38A,F233S}$.

Next, $pAC-FDS_{I78G,Y81A}$-idi or pAC-hexPS was co-expressed with 8 kinds of CrtM variants (pUC-CrtM variants), and carotenoid synthesis amounts thereof were investigated by a similar method. FIG. 23 shows the results. The $C_{55}$ backbone was synthesized in a larger amount in the cells co-expressing $FDS_{I78G,Y81A}$-idi with $CrtM_{F26A,F233S}$ or $CrtM_{F26A,W38A,F233S}$. The $C_{60}$ backbone was efficiently synthesized in the cells co-expressing HexPS with $CrtM_{W38A,F233S}$ or $CrtM_{F26A,W38A,F233S}$.

INDUSTRIAL APPLICABILITY

As described above, the production method of the present invention can synthesize the desaturated $C_{50}$ carotenoid in an extremely efficient manner, and allows various $C_H$ carotenoids to be synthesized. The $C_{50}$ carotenoid is rarely found in nature, and it is not too much to say that there is no synthesis example thereof. Carotenoids are known to have physiological activities such as an antioxidant action. Of those, the $C_{50}$ carotenoid is expected to exhibit unprecedented novel actions and to have remarkably enhanced activities as compared to conventional carotenoids. For example, the $C_{50}$ carotenoid is expected to have the potentiality of having a high antioxidant activity, an application as a novel seed for a physiologically active substance having an antitumor activity or the like, and a use as a functional pigment molecule. Further, the production method of the present invention may be utilized in the highly efficient synthesis of the desaturated $C_{55}$ carotenoid, the desaturated $C_{60}$ carotenoid, and the like. In addition, the production method of the present invention is considered to drastically increase variety of synthesizable carotenoids, by being used in combination with related art such as cells having an enhanced isoprenoid synthetic pathway (Klein-Marcuschamer D et al.: Trends Biotechnol 25, 417-424 (2007), Kirby J et al.: Nat Prod Rep 25, 656-661 (2008)).

What is claimed is:

1. A method of producing a carotenoid having 55 carbon atoms, comprising: culturing, in a medium, a cell transformed with a mutant diapophytoene synthase gene and a mutant farnesyl diphosphate synthase gene; and
    obtaining the carotenoid having 55 carbon atoms from a culture after the culturing,
    wherein the transformation is performed by a plasmid having the nucleotide sequence of SEQ ID NO: 26 that contains the mutant diapophytoene synthase gene and a plasmid having the nucleotide sequence of SEQ ID NO: 25 that contains the mutant farnesyl diphosphate synthase gene.

2. A method of producing a carotenoid having 60 carbon atoms, comprising: culturing, in a medium, a cell transformed with a mutant diapophytoene synthase gene and a mutant hexaprenyl diphosphate synthase gene; and
    obtaining the carotenoid having 60 carbon atoms from a culture after the culturing,
    wherein the transformation is performed by a plasmid having the nucleotide sequence of SEQ ID NO: 26 that contains the mutant diapophytoene synthase gene and a plasmid having the nucleotide sequence of SEQ ID NO: 24 that contains the mutant farnesyl diphosphate synthase gene.

* * * * *